US009272035B2

(12) United States Patent
Schafer et al.

(10) Patent No.: US 9,272,035 B2
(45) Date of Patent: Mar. 1, 2016

(54) METHODS AND COMPOSITIONS USING PDE4 INHIBITORS FOR THE TREATMENT AND MANAGEMENT OF AUTOIMMUNE AND INFLAMMATORY DISEASES

(75) Inventors: Peter H. Schafer, Somerset, NJ (US); Anita Gandhi, Bernardsville, NJ (US); Lori Capone, Edison, NJ (US)

(73) Assignee: Celgene Corporation, Summit, NJ (US)

( * ) Notice: Subject to any disclaimer, the term of this patent is extended or adjusted under 35 U.S.C. 154(b) by 302 days.

(21) Appl. No.: 13/458,896

(22) Filed: Apr. 27, 2012

(65) Prior Publication Data

US 2012/0276087 A1    Nov. 1, 2012

Related U.S. Application Data

(60) Provisional application No. 61/480,263, filed on Apr. 28, 2011.

(51) Int. Cl.
| | |
|---|---|
| *A61K 31/10* | (2006.01) |
| *A61K 31/165* | (2006.01) |
| *A61K 31/40* | (2006.01) |
| *A61K 31/4015* | (2006.01) |
| *A61K 45/06* | (2006.01) |
| *A61K 31/4035* | (2006.01) |
| *A61K 31/519* | (2006.01) |
| *A61K 38/13* | (2006.01) |
| *A61K 38/17* | (2006.01) |
| *A61K 39/395* | (2006.01) |

(52) U.S. Cl.
CPC ............... *A61K 45/06* (2013.01); *A61K 31/10* (2013.01); *A61K 31/165* (2013.01); *A61K 31/40* (2013.01); *A61K 31/4015* (2013.01); *A61K 31/4035* (2013.01); *A61K 31/519* (2013.01); *A61K 38/13* (2013.01); *A61K 38/177* (2013.01); *A61K 39/395* (2013.01)

(58) Field of Classification Search
CPC ..... A61K 31/10; A61K 31/165; A61K 31/40; A61K 31/4015
USPC ........................................................ 514/415
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 5,059,595 A | 10/1991 | Le Grazie | |
| 5,073,543 A | 12/1991 | Marshall et al. | |
| 5,120,548 A | 6/1992 | McClelland et al. | |
| 5,156,960 A * | 10/1992 | Jekkel nee Bokany et al. ........................... | 435/71.1 |
| 5,354,556 A | 10/1994 | Sparks et al. | |
| 5,591,767 A | 1/1997 | Mohr et al. | |
| 5,639,476 A | 6/1997 | Oshlack et al. | |
| 5,674,533 A | 10/1997 | Santus et al. | |
| 5,733,566 A | 3/1998 | Lewis | |
| 6,020,358 A | 2/2000 | Muller et al. | |
| 6,962,940 B2 * | 11/2005 | Muller et al. .................. | 514/417 |
| 7,208,516 B2 | 4/2007 | Muller et al. | |
| 7,276,529 B2 | 10/2007 | Muller et al. | |
| 7,358,272 B2 | 4/2008 | Muller et al. | |
| 7,427,638 B2 | 9/2008 | Muller et al. | |
| 7,507,759 B2 | 3/2009 | Muller et al. | |
| 7,659,302 B2 | 2/2010 | Muller et al. | |
| 7,659,303 B2 | 2/2010 | Muller et al. | |
| 7,893,101 B2 | 2/2011 | Muller et al. | |
| 8,093,283 B2 | 1/2012 | Muller et al. | |
| 8,455,536 B2 | 6/2013 | Muller et al. | |
| 8,629,173 B2 | 1/2014 | Muller et al. | |
| 2006/0148882 A1 | 7/2006 | Zeldis et al. | |
| 2006/0183787 A1 | 8/2006 | Muller et al. | |
| 2008/0234359 A1 | 9/2008 | Muller et al. | |
| 2009/0239926 A1 | 9/2009 | Schafer et al. | |
| 2010/0168475 A1 | 7/2010 | Saindane et al. | |
| 2014/0024695 A1 | 1/2014 | Muller et al. | |
| 2014/0100259 A1 | 4/2014 | Muller et al. | |

FOREIGN PATENT DOCUMENTS

| | | | |
|---|---|---|---|
| WO | 03/080049 A1 | 10/2003 | |
| WO | 2006/065814 A1 | 6/2006 | |

OTHER PUBLICATIONS

U.S. Appl. No. 60/366,515, filed Mar. 20, 2002, Schafer et al.
U.S. Appl. No. 60/438,450, filed Jan. 7, 2003, Schafer et al.
U.S. Appl. No. 60/634,982, filed Dec. 13, 2004, Zeldis et al.
Beavo and Reitsnyder, "Primary sequence of cyclic nucleotide phosphodiesterase isozymes and the design of selective inhibitors," Trends Pharmcol. Sci., 11(4):150-155 (1990).
Carstensen, Drug Stability: Principles & Practices, Second Edition, Marcel Dekker, New York, NY, pp. 379-380 (1995).
Dong et al., "Inhibition of PDE3, PDE4 and PDE7 potentiates glucocorticoid-induced apoptosis and overcomes glucocorticoid resistance in CEM T leukemic cells," Biochem. Pharmacol., 79(3):321-329 (2010).
Fox et al., "Combined oral cyclosporin and methotrexate therapy in patients with rheumatoid arthritis elevates methotrexate levels and reduces 7-hydroxymethotrexate levels when compared with methotrexate alone," Rheumatology (Oxford), 42(8):989-994 (2003).

(Continued)

*Primary Examiner* — Yong Chong
(74) *Attorney, Agent, or Firm* — Jones Day

(57) ABSTRACT

Methods of treating, preventing, or managing autoimmune inflammatory diseases and disorders including but not limited to spondylitis, juvenile rheumatoid arthritis, psoriasis, psoriatic arthritis, osteoarthritis, ankylosing spondylitis, and rheumatoid arthritis by the administration of phosphodiesterase 4 (PDE4) inhibitors in combination with other therapeutics are disclosed. Pharmaceutical compositions, dosage forms, and kits suitable for use in methods of the invention are also disclosed.

10 Claims, 27 Drawing Sheets

(56) References Cited

OTHER PUBLICATIONS

Figure 1:
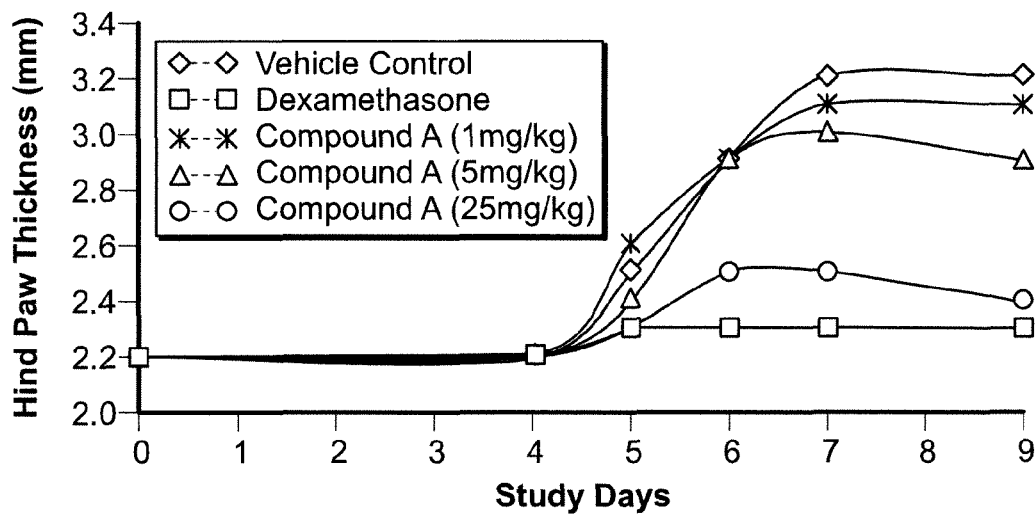

Gladman et al., Kelley's Textbook of Rheumatology, 2 Vols. 6th Edition, W. B. Saunders Company, Chapter 71, pp. 1071-1077 (2001).

Gladman, "Current concepts in psoriatic arthritis," Curr. Opin. Rheumatol., 14(4):361-366 (2002).

Kowalczyk et al., "Effect of phosphodiesterase antagonists on glucocorticoid mediated growth inhibition in murine skin cell lines," Eur. J. Pharmacol., 610(1-3):29-36 (2009).

Long et al., "Human articular chondrocytes produce IL-7 and respond to IL-7 with increased production of matrix metalloproteinase-13," Arthritis Res. Ther., 10(1):R23 (2008).

Lowe et al., "Patent evaluation: novel dioxolanes as cholesterol lowering agents," Exp. Opin. Ther. Patents, 2 (8):1309-1310 (1992).

Lowe et al., Drugs of the Future, 17(9):799-807 (1992).

McCann et al., "Apremilast, a novel PDE4 inhibitor, inhibits spontaneous production of tumour necrosis factor-alpha from human rheumatoid synovial cells and ameliorates experimental arthritis," Arthritis Res. Ther., 12(3):R107 (2010).

Meyers et al., "Phosphodiesterase 4 inhibitors augment levels of glucocorticoid receptor in B cell chronic lymphocytic leukemia but not in normal circulating hematopoietic cells," Clin. Cancer Res., 13(16):4920-4927 (2007).

Patel et al., "Psoriatic arthritis—emerging concepts," Rheumatology (Oxford), 40(3):243-246 (2001).

Rihl et al., "Identification of interleukin-7 as a candidate disease mediator in spondylarthritis," Arthritis Rheum., 58 (11):3430-3435 (2008).

The Merck Manual, 17th Edition, Merck & Company, West Point, PA, pp. 448, 944-952 (1999).

Tierney et al. (eds), Current Medical Diagnosis & Treatment 1998, 37th Edition, Appleton & Lange, Stamford, CT, p. 793 (1998).

Verghese et al., "Differential regulation of human monocyte-derived TNF alpha and IL-1 beta by type IV cAMP-phosphodiesterase (cAMP-PDE) inhibitors," J. Pharmacol. Exp. Ther., 272(3), 1313-1320 (1995).

Wilen et al., "Strategies in optical resolutions," Tetrahedron, 33:2725-2736 (1977).

Wilen, Tables of Resolving Agents and Optical Resolutions, (E.L. Eliel, Ed.), University of Notre Dame Press, Notre Dame, IN, p. 268 (1972).

Wolff ed., Burger's Medicinal Chemistry and Drug Discovery, 5th Edition, John Wiley & Sons, Inc., pp. 172-178, 949-982 (1995).

Choy et al., "Cytokine pathways and joint inflammation in rheumatoid arthritis," N. Eng. J. Med., 344:907-916 (2001), abstract only.

Feldmann et al., "Role of cytokines in rheumatoid arthritis," Ann. Rev. Immunol., 14:397-440 (1996), abstract only.

Isomaki et al., "The presence of interleukin-13 in rheumatoid synovium and its antiinflammatory effects on synovial fluid macrophages from patients with rheumatoid arthritis," Arthritis Rheum., 39(10):1693-1702 (1996), abstract only.

Pokorny et al., "Evidence for negative association of the chemokine receptor CCR5 d32 polymorphism with rheumatoid arthritis," Ann. Rheum. Dis., 64:487-490 (2005).

* cited by examiner

METHODS AND COMPOSITIONS USING PDE4 INHIBITORS FOR THE TREATMENT AND MANAGEMENT OF AUTOIMMUNE AND INFLAMMATORY DISEASES

The present application claims priority to U.S. Provisional Patent Application No. 61/480,263, filed Apr. 28, 2011, the entirety of which is incorporated herein by reference.

1. FIELD

Provided herein are methods of treating, preventing, or managing autoimmune and inflammatory diseases and disorders including but not limited to spondylitis, juvenile rheumatoid arthritis, psoriasis, psoriatic arthritis, osteoarthritis, ankylosing spondylitis, and rheumatoid arthritis by the administration of phosphodiesterase 4 (PDE4) inhibitors in combination with other therapeutics. Specifically, provided herein are methods of treating, preventing, or managing arthritis, psoriasis, psoriatic arthritis and rheumatoid arthritis, using (S)-N-(2-(1-(3-ethoxy-4-methoxyphenyl)-2-(methylsulfonyl)ethyl)-1,3-dioxoisoindolin-4-yl)acetamide in combination with either cyclosporine A or other calnineurin inhibitors, etanercept or other TNF inhibitors, or methotrexate or other anti-metabolites, and/or using (S)-N-(2-(1-(3-ethoxy-4-methoxyphenyl)-2-(methylsulfonyl)ethyl)-3-oxoisoindolin-4-yl)cyclopropanecarboxamide in combination with either cyclosporine A, etanercept, or methotrexate or similar drugs.

2. BACKGROUND

Inflammation plays a fundamental role in host defenses and the progression of immune-mediated diseases. The inflammatory response is initiated in response to injury (e.g., trauma, ischemia, and foreign particles) and infection (e.g., bacterial or viral infection) by a complex cascade of events, including chemical mediators (e.g., cytokines and prostaglandins) and inflammatory cells (e.g., leukocytes). The inflammatory response is characterized by increased blood flow, increased capillary permeability, and the influx of phagocytic cells. These events result in swelling, redness, warmth (altered heat patterns), and pus formation at the site of injury or infection.

Cytokines and prostaglandins control the inflammatory response, and are released in an ordered and self-limiting cascade into the blood or affected tissues. This release of cytokines and prostaglandins increases the blood flow to the area of injury or infection, and may result in redness and warmth. Some of these chemicals cause a leak of fluid into the tissues, resulting in swelling. This protective process may stimulate nerves and cause pain. These changes, when occurring for a limited period in the relevant area, work to the benefit of the body.

Tumor necrosis factor alpha (TNF-α) is a cytokine that is released primarily by mononuclear phagocytes in response to immunostimulators. TNF-α is capable of enhancing most cellular processes, such as differentiation, recruitment, proliferation, and proteolytic degradation. At low levels, TNF-α confers protection against infective agents, tumors, and tissue damage. But TNF-α also has a role in many diseases. When administered to mammals or humans, TNF-α causes or aggravates inflammation, fever, cardiovascular effects, hemorrhage, coagulation, and acute phase responses similar to those seen during acute infections and shock states. Enhanced or unregulated TNF-α production has been implicated in a number of diseases and medical conditions, for example, cancers, such as solid tumors and blood-borne tumors; heart disease, such as congestive heart failure; and viral, genetic, inflammatory, allergic, and autoimmune diseases.

Adenosine 3',5'-cyclic monophosphate (cAMP) also plays a role in many diseases and conditions, such as but not limited to asthma and inflammation, and other conditions (Lowe and Cheng, *Drugs of the Future,* 17(9), 799-807, 1992). It has been shown that the elevation of cAMP in inflammatory leukocytes inhibits their activation and the subsequent release of inflammatory mediators, including TNF-α and NF-κB. Increased levels of cAMP also leads to the relaxation of airway smooth muscle.

It is believed that the primary cellular mechanism for the inactivation of cAMP is the breakdown of cAMP by a family of isoenzymes referred to as cyclic nucleotide phosphodiesterases (PDE) (Beavo and Reitsnyder, *Trends in Pharm.,* 11, 150-155, 1990). There are eleven known PDE families. It is recognized, for example, that the inhibition of PDE type IV is particularly effective in both the inhibition of inflammatory mediator release and the relaxation of airway smooth muscle (Verghese, et al., *Journal of Pharmacology and Experimental Therapeutics,* 272(3), 1313-1320, 1995). Thus, compounds that inhibit PDE4 specifically, may inhibit inflammation and aid the relaxation of airway smooth muscle with a minimum of unwanted side effects, such as cardiovascular or anti-platelet effects. Currently used PDE4 inhibitors lack selective action at acceptable therapeutic doses.

Inflammatory diseases such as arthritis, related arthritic conditions (e.g., osteoarthritis, rheumatoid arthritis, and psoriatic arthritis), inflammatory bowel disease (e.g., Crohn's disease and ulcerative colitis), sepsis, psoriasis, atopic dermatitis, contact dermatitis, and chronic obstructive pulmonary disease, chronic inflammatory pulmonary diseases are also prevalent and problematic ailments. Enhanced or unregulated TNF-α production plays a central role in the inflammatory response and the administration of their antagonists block chronic and acute responses in animal models of inflammatory disease.

Arthritis is a systemic autoimmune disease that can refer to a group of conditions involving damage to the joints of the body. There are over 100 different forms of arthritis. The most common form is osteoarthritis (degenerative joint disease) and other arthritis forms are rheumatoid arthritis, psoriatic arthritis, and related autoimmune diseases such as lupus and gout. Rheumatoid arthritis is characterized by a chronic inflammation of the joints. Both synovial tissue and fluid are invaded by inflammatory cells which lead to cytokine production. T cells and monocytes infiltrating the joints display an increased activation of Type 1 and 2 immune response markers.

Psoriasis is a chronic systemic autoimmune disease that appears on the skin. There are five types of psoriasis: plaque, guttate, inverse, pustular and erythrodermic. The most common form, plaque psoriasis, is commonly seen as red and white hues of scaly patches appearing on the top first layer of the epidermis. Some patients, though, have no dermatological symptoms. In plaque psoriasis, skin rapidly accumulates at these sites, which gives it a silvery-white appearance. Plaques frequently occur on the skin of the elbows and knees, but can affect any area, including the scalp, palms of hands and soles of feet, and genitals. In contrast to eczema, psoriasis is more likely to be found on the outer side of the joint. The disorder is a chronic recurring condition that varies in severity from minor localized patches to complete body coverage. Fingernails and toenails are frequently affected (psoriatic nail dystrophy) and can be seen as an isolated symptom. Psoriasis can also cause inflammation of the joints, which is known as psoriatic arthritis. In psoriasis, one hypothesis is that T cells become active, migrate to the dermis and trigger the release of cytokines, TNF-α in particular, which causes inflammation and the rapid proliferation of keratinocytes.

Psoriatic arthritis is a chronic inflammatory arthritic condition affecting the skin, the joints, the insertion sites of tendons, ligaments, and fascia. Gladman, *Current Opinion in Rheumatology*, "Current concepts in psoriatic arthritis," 2002, 14:361-366, and Ruddy et al., *Rheumatology, vol. 2*, chapter 71, page 1071, 6th ed., 2001. Psoriatic arthritis is commonly associated with psoriasis. Id. Approximately 7% of patients with psoriasis develop psoriatic arthritis. *The Merck Manual*, 448 (17th ed., 1999).

Psoriatic arthritis may appear in a variety of clinical patterns. There are five general patterns of psoriatic arthritis: arthritis of the distal interphalangeal joints, destructive arthritis, symmetric polyarthritis indistinguishable from rheumatoid arthritis, asymmetric oligoarthritis, and spondyloarthropathy. Ruddy et al., page 1073. Psoriasis appears to precede the onset of psoriatic arthritis in 60-80% of patients. Occasionally, arthritis and psoriasis appear simultaneously. Cutaneous eruptions may be preceded by the arthropathy.

Symptoms of psoriatic arthritis include extra bone formation, joint stiffness, dactylitis, enthesopathy, tendonitis, and spondylitis. Gladman, page 362. Most patients have the classic psoriasis pattern of skin lesions. Ruddy et al., page 1075. Scaly, erythematous plaque, guttate lesions, lakes of pus, and erythroderma are psoriatic skin lesions that may be seen in patients with psoriatic arthritis. Nail lesions, including pitting, Beau lines, leukonychia, onycholysis, oil spots, subungual hyperkeratosis, splinter hemorrhages, spotted lunulae, and cracking, are clinical features significantly associated with the development of psoriatic arthritis. Ruddy et al., page 1076. Ocular symptoms in psoriatic arthritis include conjunctivitis, iritis, episcleritis, keratoconjunctivitis sicca and aortic insufficiency.

Although the exact cause of psoriatic arthritis is unknown, genetic, environmental, immunologic, and vascular factors contribute to one's predisposition. Ruddy et al., pages 1071-72, and Gladman, page 363. The disease is more likely to occur in first-degree relatives who are affected than in the general population. Ruddy et al., page 1071. Population studies have shown that multiple human leukocyte antigens (HLA) are associated. British Society for Rheumatology, Rheumatology, 2001; 40:243, and Gladman, page 362. Much evidence suggests that a T-cell-mediated process drives the pathophysiology of psoriatic arthritis. Ruddy et al., pages 1071 and 1077, and Gladman, page 363. Activated T cells may contribute to the enhanced production of cytokines found in synovial fluid. Th1 cytokines (e.g., tumor necrosis factor-alpha (TNF-alpha), interleukin (IL)-1-beta and IL-10) are more prevalent in psoriatic arthritis than in rheumatoid arthritis, suggesting that the two diseases may result from a different mechanism. Ruddy et al., page 1071. Monocytes also play a role in psoriatic arthritis and are responsible for the production of matrix metalloproteinases, which may mediate the destructive changes in the joints of patients with psoriatic arthritis. Gladman, page 364.

Internationally, the incidence of psoriatic arthritis is 1-40%. Psoriatic arthritis usually develops in the fourth to sixth decades of life, but it can occur at almost any age. Men and women are affected equally, but a male predominance occurs in the spondylitic form, while a female predominance occurs in the rheumatoid form. Ruddy et al., page 1077.

There is a significant need for safe and effective methods of treating, preventing and managing psoriatic arthritis, particularly for patients that are refractory to conventional treatments. In addition, there is a need to treat such disease while reducing or avoiding the toxicity and/or side effects associated with conventional therapies.

Thus, compounds and compositions that can block the activity or inhibit the production of PDE4 and certain cytokines, including TNF-α, may be beneficial therapeutics. Many small-molecule inhibitors have demonstrated an ability to treat or prevent inflammatory diseases implicated by PDE4 or TNF-α (for a review, see Lowe, 1998 *Exp. Opin. Ther. Patents* 8:1309-1332). One such class of molecules are the substituted phenethylsulfones described in U.S. Pat. Nos. 6,020,358; 6,962,940; 7,208,526; and 7,659,302, and U.S. Patent Publication No. 2008/0234359, all of which are hereby incorporated by reference in their entirety. For example, Apremilast is a novel oral pluripotent immunomodulator that specifically inhibits PDE4 and inhibits spontaneous production of TNF-α from human rheumatoid synovial cells and ameliorates experimental arthritis. (McCann et al., *Arthritis Res. Ther.* 2010, 12(3):R107). Additionally, Etanercept (Enbrel®) is a useful TNF-α inhibitor.

A delicate well-balanced interplay between the humoral and cellular immune elements in the inflammatory response enables the elimination of harmful agents and the initiation of the repair of damaged tissue. When this delicately balanced interplay is disrupted, the inflammatory response may result in considerable damage to normal tissue and may be more harmful than the original insult that initiated the reaction. In these cases of uncontrolled inflammatory responses, clinical intervention is needed to prevent tissue damage and organ dysfunction. Diseases such as psoriasis, rheumatoid arthritis, osteoarthritis, psoriatic arthritis, Crohn's disease, asthma, allergies or inflammatory bowel disease, are characterized by chronic inflammation.

Current treatments for inflammatory disorders involve symptomatic medications and immunosuppressive agents to control symptoms. For example, nonsteroidal anti-inflammatory drugs (NSAIDs) such as aspirin, ibuprofen, fenoprofen, naproxen, tolmetin, sulindac, meclofenamate sodium, piroxicam, flurbiprofen, diclofenac, oxaprozin, nabumetone, etodolac, and ketoprofen have analgesic and anti-inflammatory effects. However, NSAIDs are believed not to be capable of altering progression of the disease. (Tierney et al. (eds), *Current Medical Diagnosis & Treatment*, 37 ed., Appleton & Lange (1998), p 793). Moreover, NSAIDs frequently cause gastrointestinal side effects, affect the lower intestinal tract causing perforation or aggravating inflammatory bowel disease, produce renal toxicity, and prolong bleeding time. Corticosteroids are another class of drugs that are commonly used to control inflammatory symptoms. Corticosteroids, like NSAIDs, do not alter the natural progression of the disease, and thus, clinical manifestations of active disease commonly reappear when the drug is discontinued. The serious problem of untoward reactions resulting from prolonged corticosteroid therapy (e.g., osteoporosis, increased risk of infection, increased appetite, hypertension, edema, peptic ulcers, psychoses) greatly limits its long-term use.

Low doses of immunosuppressive agents such as cytotoxic agents may be used for the treatment of inflammatory disorders. For example, some treatments for psoriasis and arthritis are based on disease-modifying anti-rheumatic drugs (DMARDs such as cyclosporine A and methotrexate), anti-inflammatory agents (TNF-α inhibitors such as etanercept), and analgesics.

New treatments for inflammatory and autoimmune disorders are constantly being sought. In particular, any new treatment that reduces the dosage and/or frequency of administration of agents currently being used, or is capable of making a currently used treatment more effective is constantly being sought. While there have been reports of combinations between PDE4 inhibitors and corticosteroids in models of leukemia and skin cancer, the combination of PDE4 inhibitors with TNF-α inhibitors, calcineurin inhibitors, or antimetabolites for the treatment of inflammatory diseases has not yet been utilized. See, e.g., Dong, H. et al., *Biochem Pharmacol.*, 2010, 79(3): 321-329; Kowalczyk P. et al., *Eur J Pharmacol.*, 2009, 610(1-3): 29-36; Meyers, J. A., et al. *Clin Cancer Res.*, 2007, 13(16): 4920-4927.

3. SUMMARY

Provided herein are methods of treating diseases and disorders utilizing a PDE4 inhibitor or a pharmaceutically acceptable salt, hydrate, solvate, clathrate, prodrug, or polymorph thereof in combination with a second active agent. In certain embodiments, the second active agent or agents are TNF-α inhibitors, calcineurin inhibitors, or antimetabolites. In certain embodiments, the diseases or disorders include, but are not limited to inflammatory or autoimmune diseases such as spondylitis (e.g., ankylosing spondylitis), juvenile rheumatoid arthritis, psoriasis, psoriatic arthritis, rheumatoid arthritis, lupus, gout, Behcet's disease, and osteoarthritis.

In one embodiment, provided herein is a method of treating psoriasis or arthritis, which comprises administering to a patient in need of such treatment a therapeutically effective amount of (S)-N-(2-(1-(3-ethoxy-4-methoxyphenyl)-2-(methylsulfonyl)ethyl)-1,3-dioxoisoindolin-4-yl)acetamide, or a pharmaceutically acceptable prodrug, polymorph, salt, or solvate thereof, and a therapeutically effective amount of one or more additional active agents selected from the group consisting of an anti-inflammatory agent (e.g. NSAID), a disease-modifying anti-rheumatic drug (DMARD) such as cyclosporine A or methotrexate, mycophenolate mofetil, a biologic agent (e.g. etanercept), a TNF-α inhibitor (e.g. etanercept), a Cox-2 inhibitor, and an analgesic.

In another embodiment, provided herein is a method of treating psoriasis or arthritis, which comprises administering to a patient in need of such treatment a therapeutically effective amount of (S)-N-(2-(1-(3-ethoxy-4-methoxyphenyl)-2-(methylsulfonyl)ethyl)-3-oxoisoindolin-4-yl)cyclopropanecarboxamide, or a pharmaceutically acceptable prodrug, polymorph, salt, or solvate thereof, and a therapeutically effective amount of one or more additional active agents selected from the group consisting of an anti-inflammatory agent (e.g. NSAID), a disease-modifying anti-rheumatic drug (DMARD) such as cyclosporine A or methotrexate, mycophenolate mofetil, a biologic agent (e.g. etanercept), a TNF-α inhibitor (e.g. etanercept), a Cox-2 inhibitor, and an analgesic.

In certain embodiments, the form of arthritis is selected from the group consisting of rheumatoid arthritis, psoriatic arthritis, osteoarthritis, lupus, and gout.

In one embodiment, the first active agent is (S)-N-(2-(1-(3-ethoxy-4-methoxyphenyl)-2-(methylsulfonyl)ethyl)-1,3-dioxoisoindolin-4-yl)acetamide, or a pharmaceutically acceptable prodrug, polymorph, salt, or solvate thereof, and the additional active agent is cyclosporine A.

In one embodiment, the first active agent is (S)-N-(2-(1-(3-ethoxy-4-methoxyphenyl)-2-(methylsulfonyl)ethyl)-1,3-dioxoisoindolin-4-yl)acetamide, or a pharmaceutically acceptable prodrug, polymorph, salt, or solvate thereof, and the additional active agent is methotrexate.

In one embodiment, the first active agent is (S)-N-(2-(1-(3-ethoxy-4-methoxyphenyl)-2-(methylsulfonyl)ethyl)-1,3-dioxoisoindolin-4-yl)acetamide, or a pharmaceutically acceptable prodrug, polymorph, salt, or solvate thereof, and the additional active agent is etanercept.

In one embodiment, the first active agent is (S)-N-(2-(1-(3-ethoxy-4-methoxyphenyl)-2-(methylsulfonyl)ethyl)-3-oxoisoindolin-4-yl)cyclopropanecarboxamide, or a pharmaceutically acceptable prodrug, polymorph, salt, or solvate thereof, and the additional active agent is cyclosporine A.

In one embodiment, the first active agent is (S)-N-(2-(1-(3-ethoxy-4-methoxyphenyl)-2-(methylsulfonyl)ethyl)-3-oxoisoindolin-4-yl)cyclopropanecarboxamide, or a pharmaceutically acceptable prodrug, polymorph, salt, or solvate thereof, and the additional active agent is methotrexate.

In one embodiment, the first active agent is (S)-N-(2-(1-(3-ethoxy-4-methoxyphenyl)-2-(methylsulfonyl)ethyl)-3-oxoisoindolin-4-yl)cyclopropanecarboxamide, or a pharmaceutically acceptable prodrug, polymorph, salt, or solvate thereof, and the additional active agent is etanercept.

4. BRIEF DESCRIPTION OF THE FIGURES

FIG. 1. shows effects of (+)-2-[1-(3-ethoxy-4-methoxyphenyl)-2-methylsulfonylethyl]-4-acetylaminoisoindoline-1,3-dione (Compound A) and dexamethasone on hind paw thickness in mice.

Figure 2:
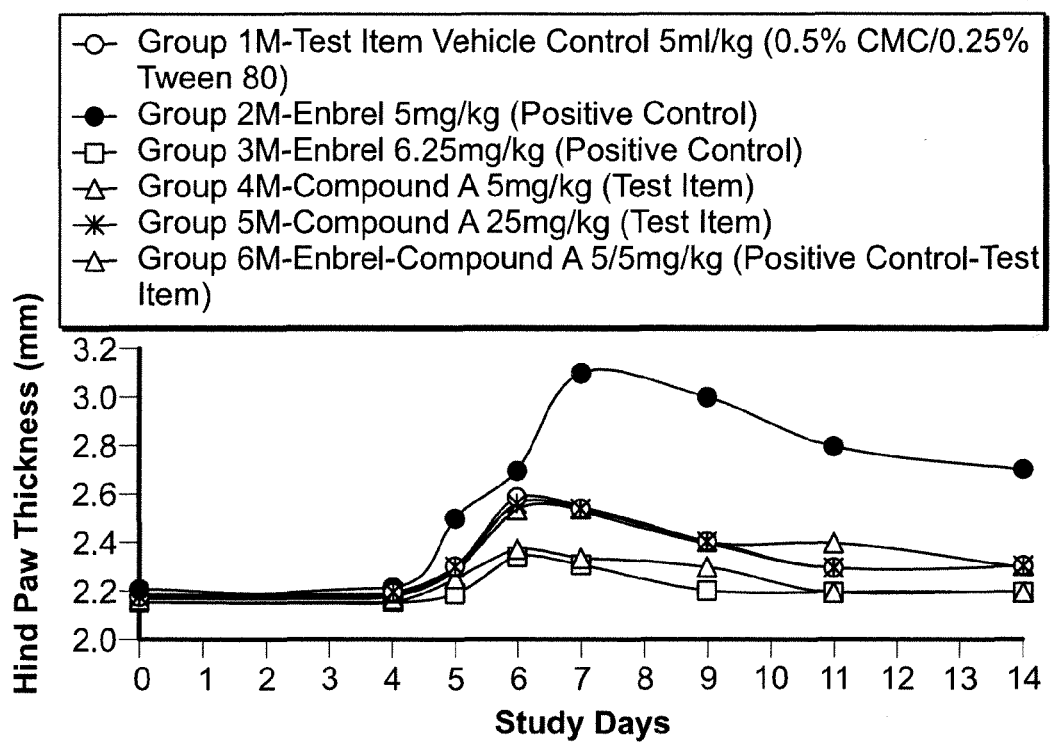

FIG. 2. shows effects of (+)-[1-(3-ethoxy-4-methoxyphenyl)-2-methylsulfonylethyl]-4-acetylaminoisoindoline-1,3-dione (Compound A) and Etanercept on hind paw thickness in mice.

Figure 3A:
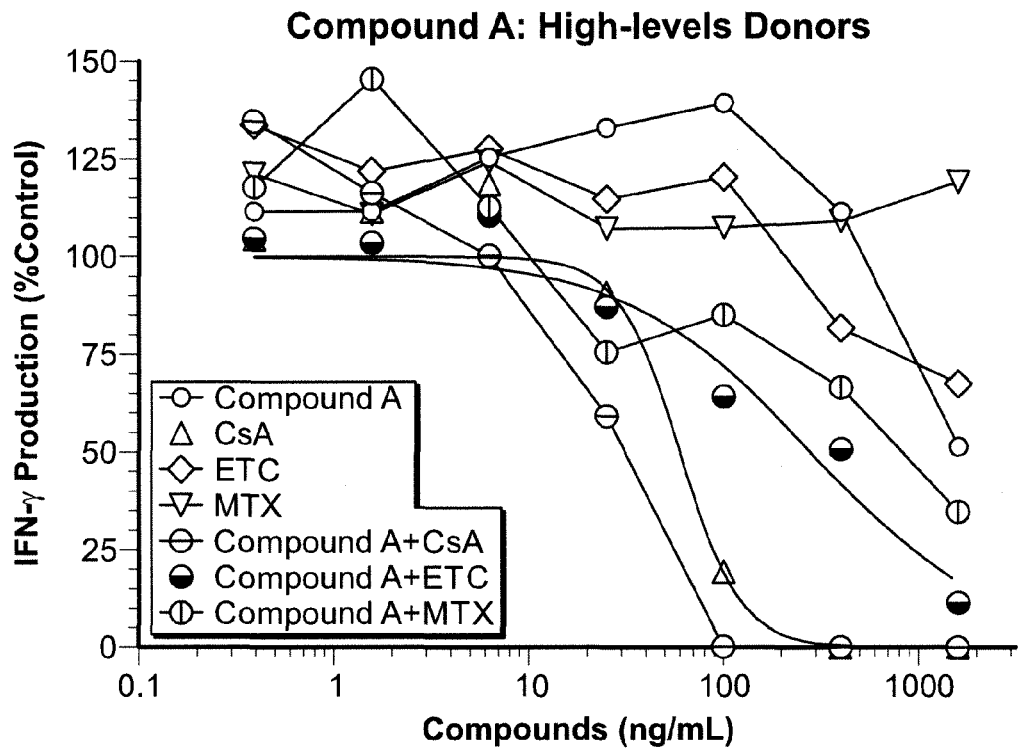
Figure 3B:
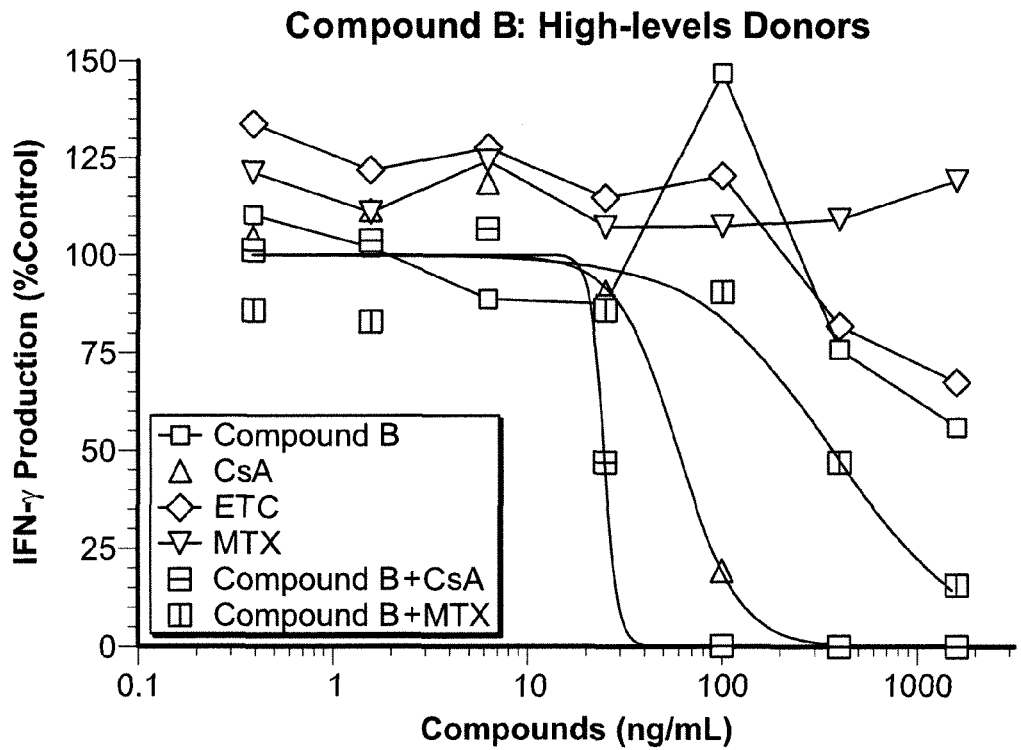

FIG. 3. shows interferon-gamma production in response to PDE4 inhibitors in combination with cyclosporine, Etanercept or methotrexate.

FIG. 4. shows interleukin-2 production in response to PDE4 inhibitors in combination with cyclosporine, Etanercept or methotrexate.

FIG. 5. shows interleukin-4 production in response to PDE4 inhibitors in combination with cyclosporine, Etanercept or methotrexate.

Figure 6A:
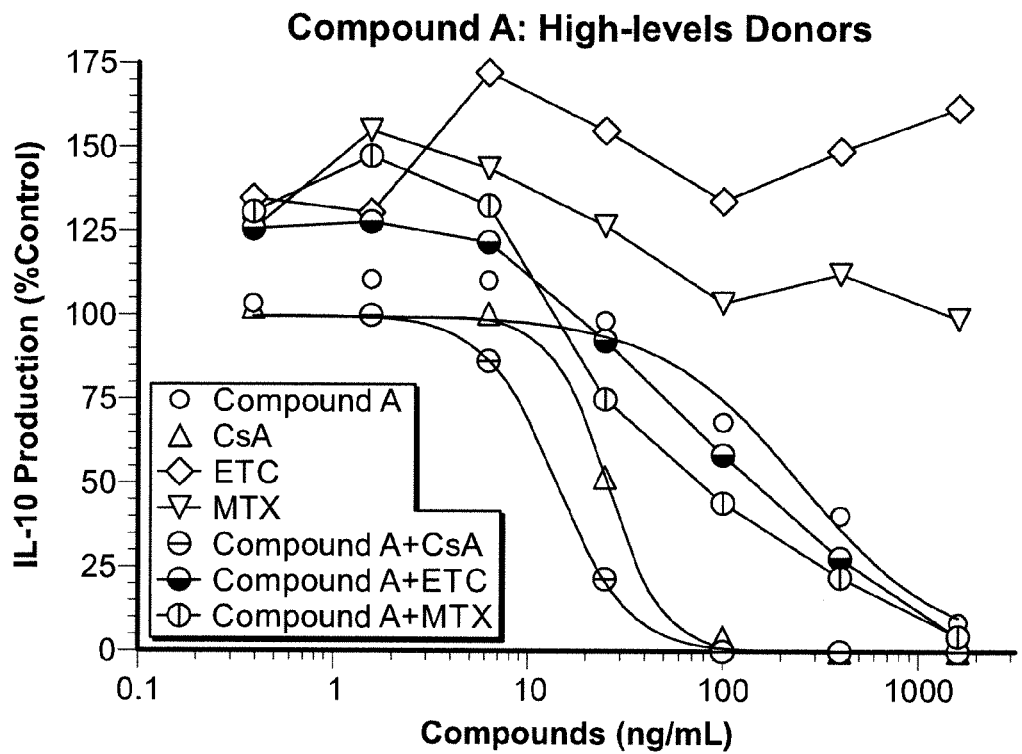
Figure 6B:
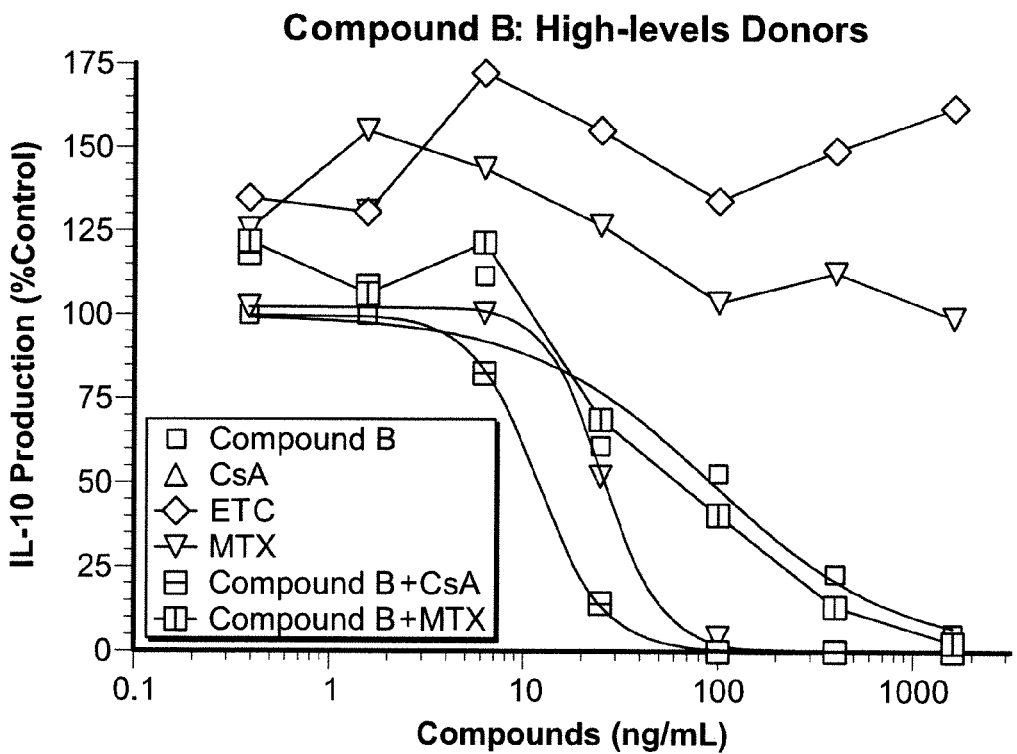

FIG. 6. shows interleukin-10 production in response to PDE4 inhibitors in combination with cyclosporine, Etanercept or methotrexate.

Figure 7A:
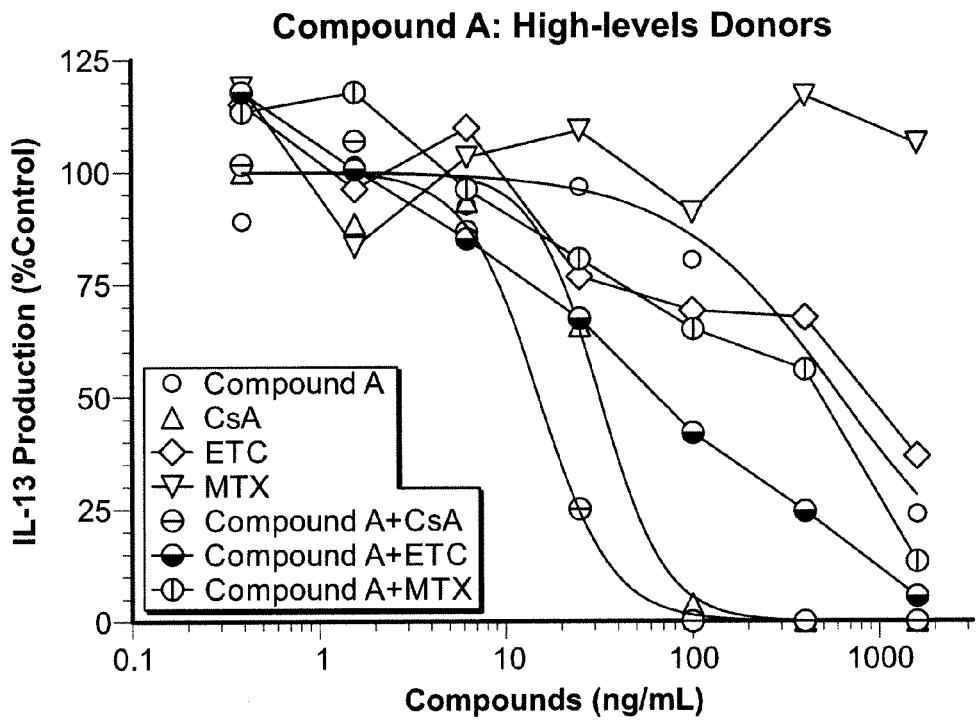
Figure 7B:
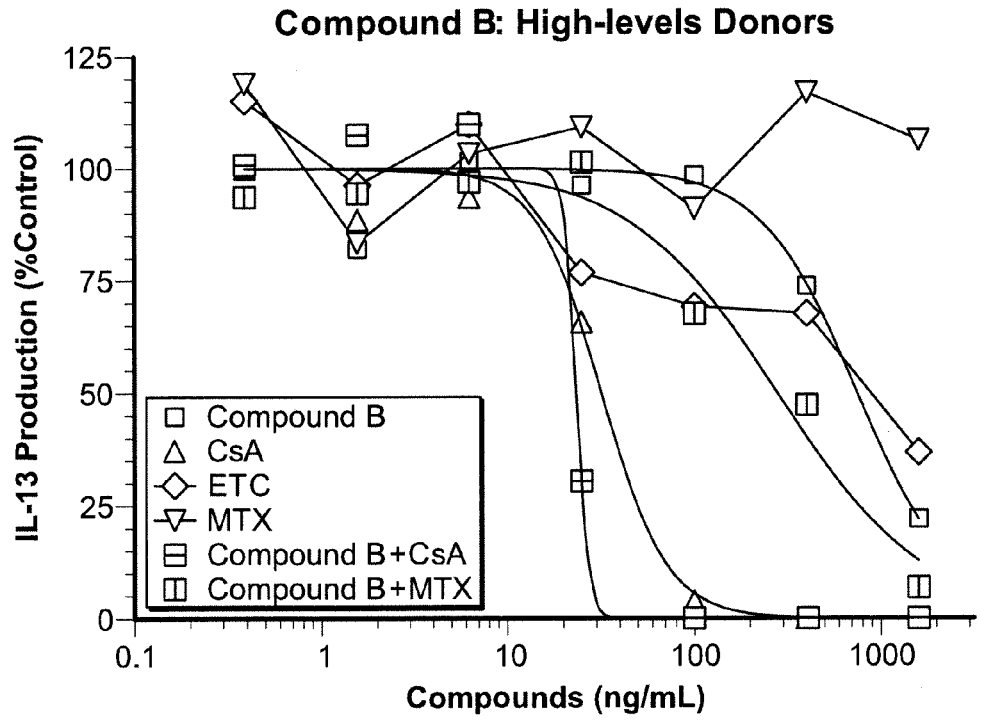

FIG. 7. shows interleukin-13 production in response to PDE4 inhibitors in combination with cyclosporine, Etanercept or methotrexate.

Figure 8A:
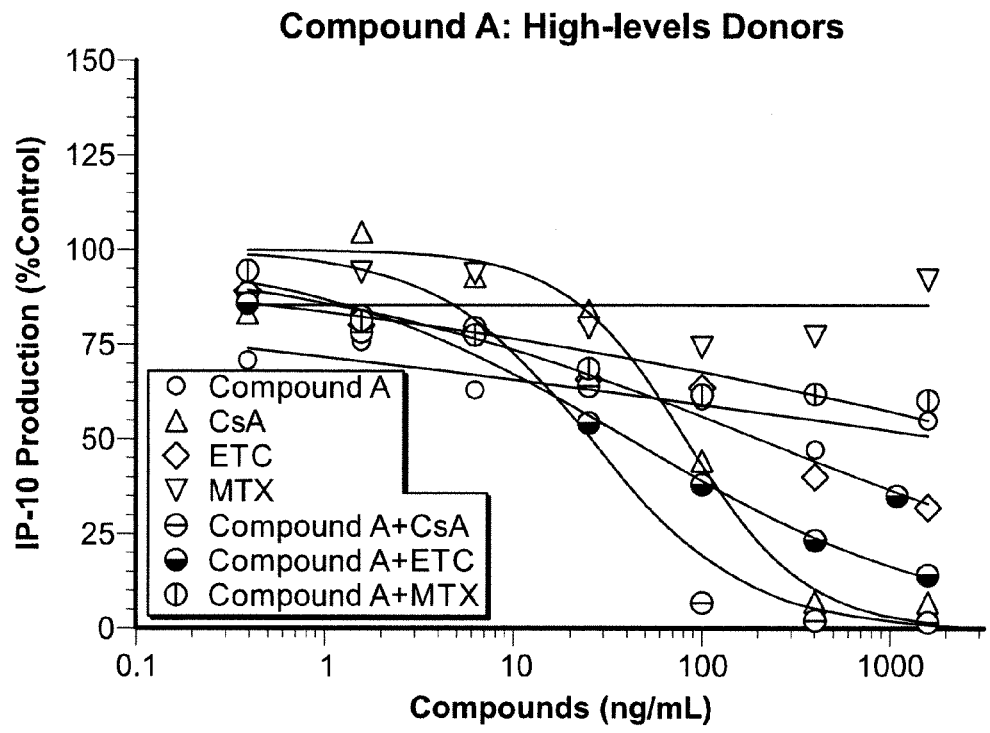
Figure 8B:
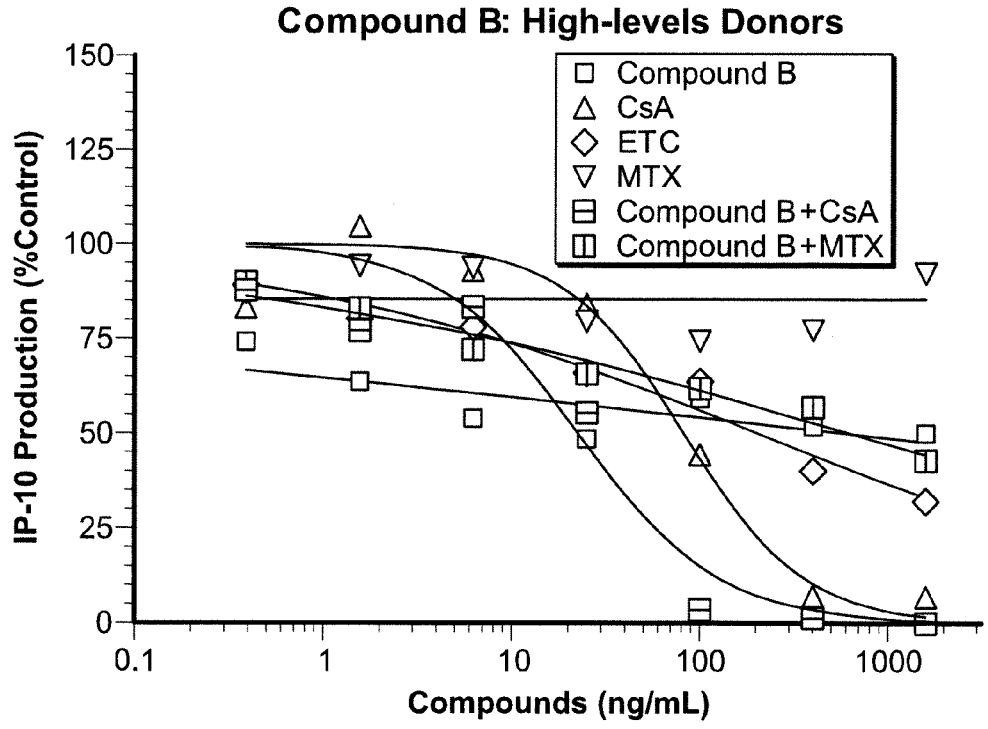

FIG. 8. shows interferon-inducible protein 10 production in response to PDE4 inhibitors in combination with cyclosporine, Etanercept or methotrexate.

Figure 9A:
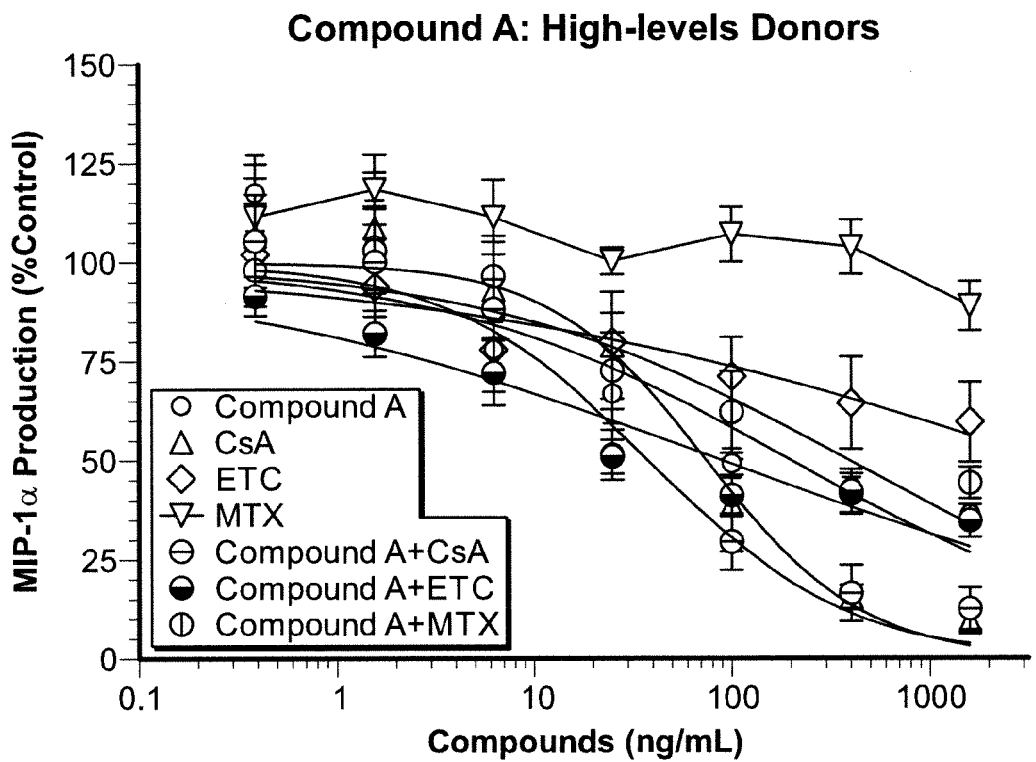

FIG. 9. shows macrophage inflammatory protein-1 alpha production in response to PDE4 Inhibitors in combination with cyclosporine, Etanercept or methotrexate.

Figure 10A:
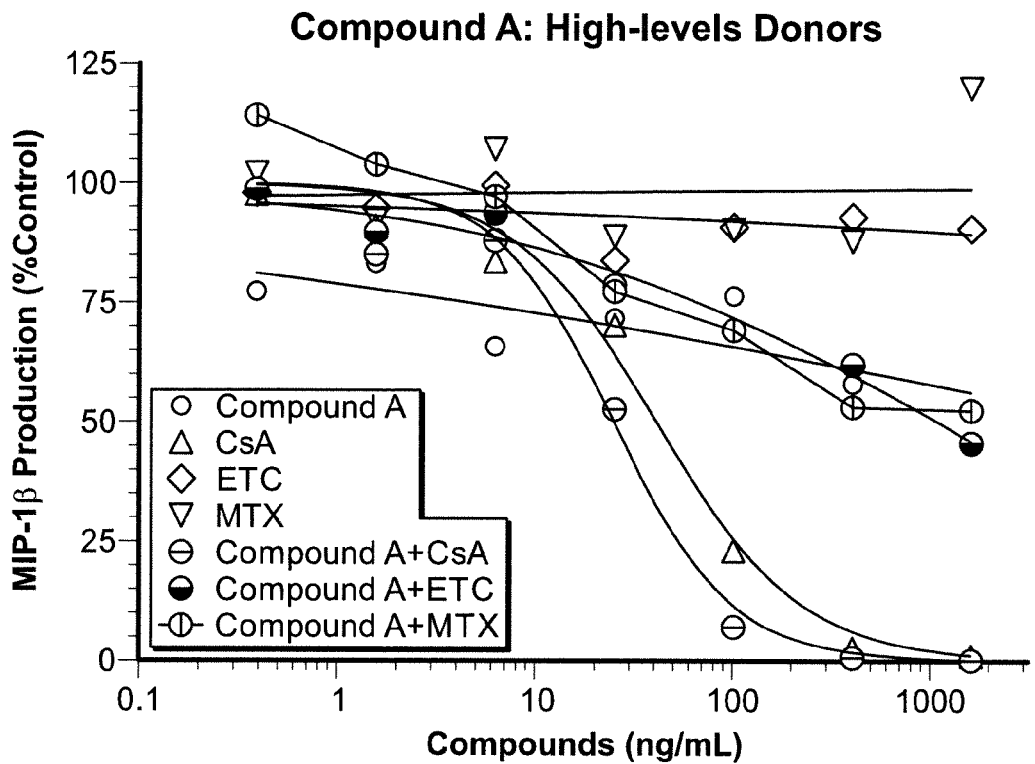
Figure 10B:
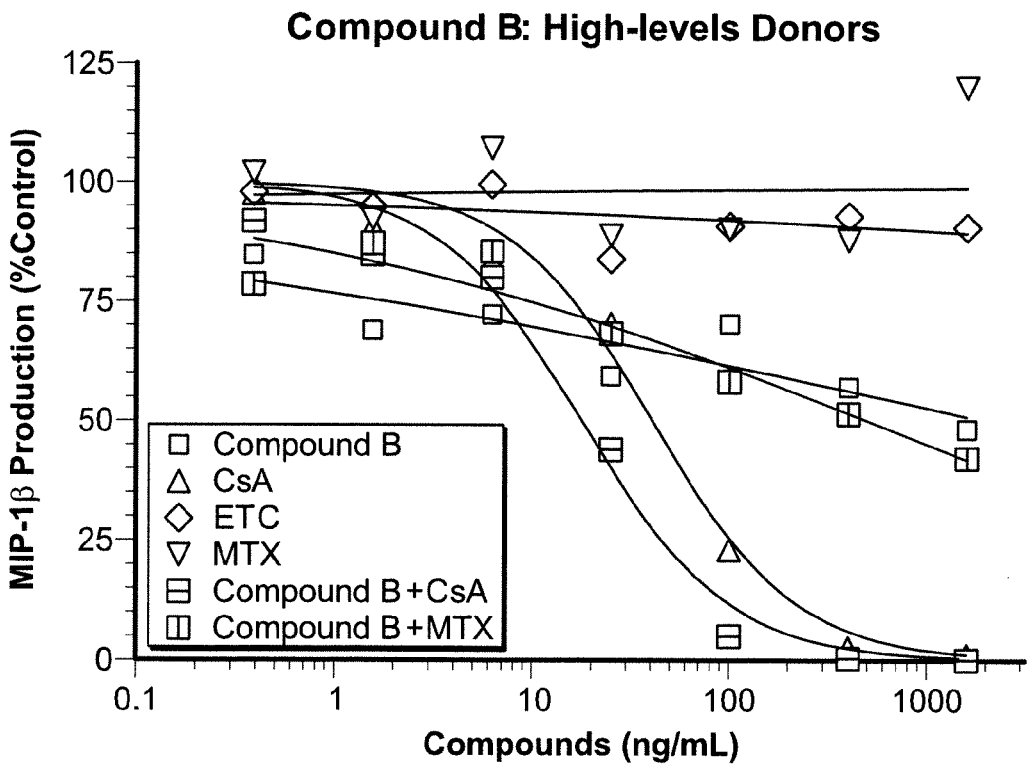

FIG. 10. shows macrophage inflammatory protein-1 beta production in response to PDE4 inhibitors in combination with cyclosporine, Etanercept or methotrexate.

Figure 11A:
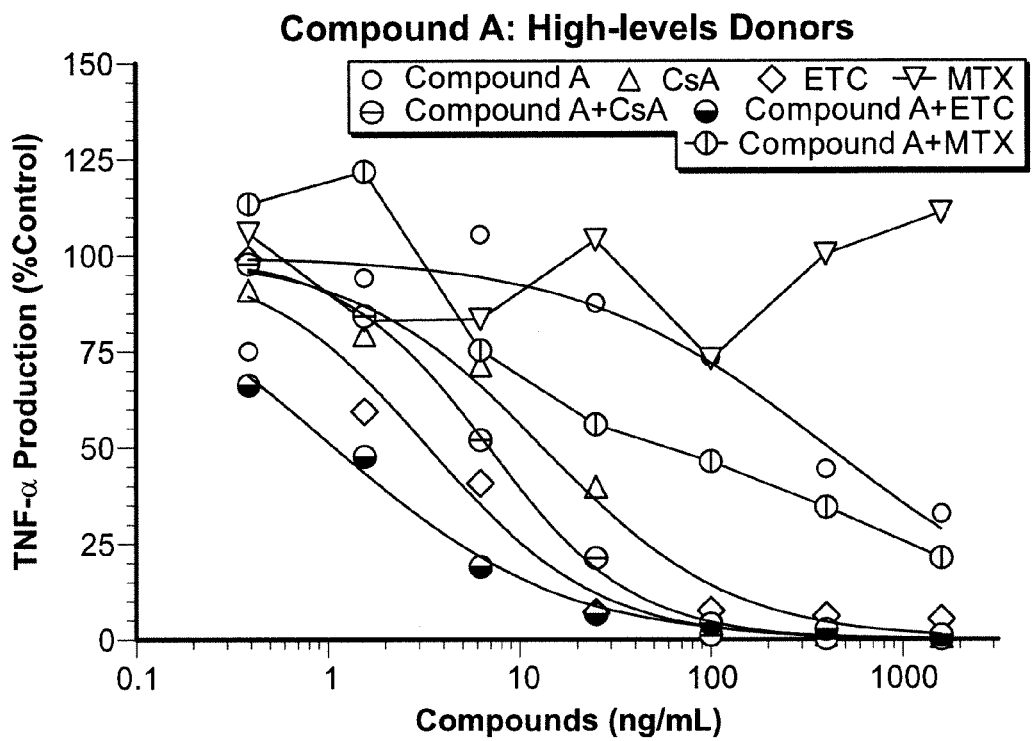
Figure 11B:
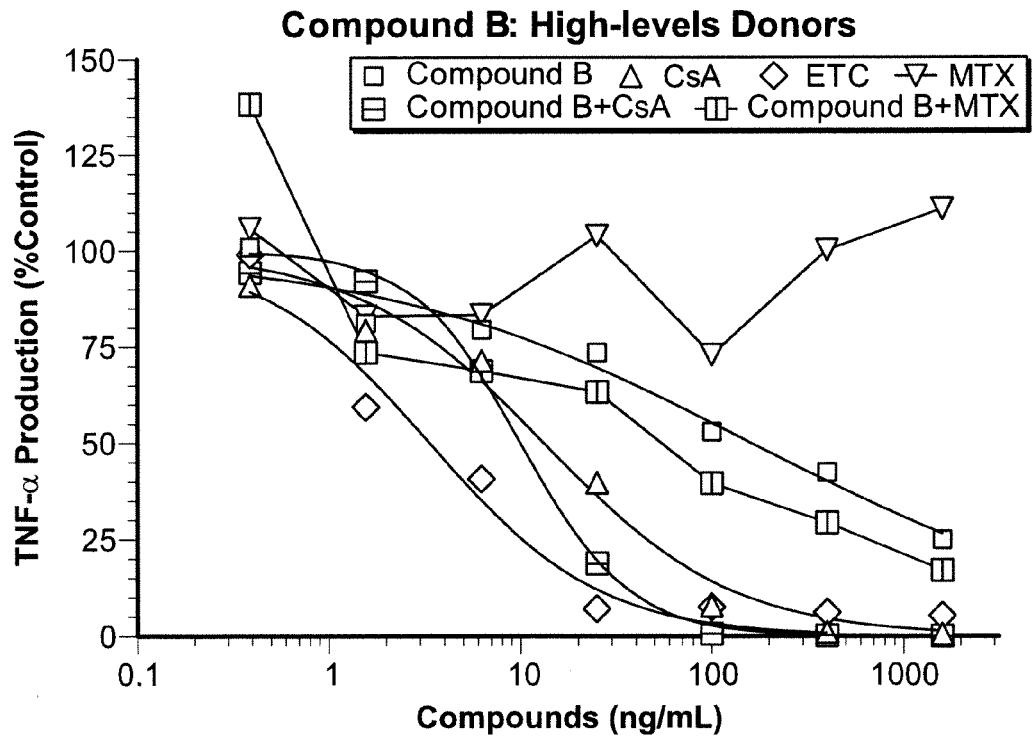

FIG. 11. shows TNF-α production in response to PDE4 inhibitors in combination with cyclosporine, Etanercept or methotrexate.

Figure 12A:
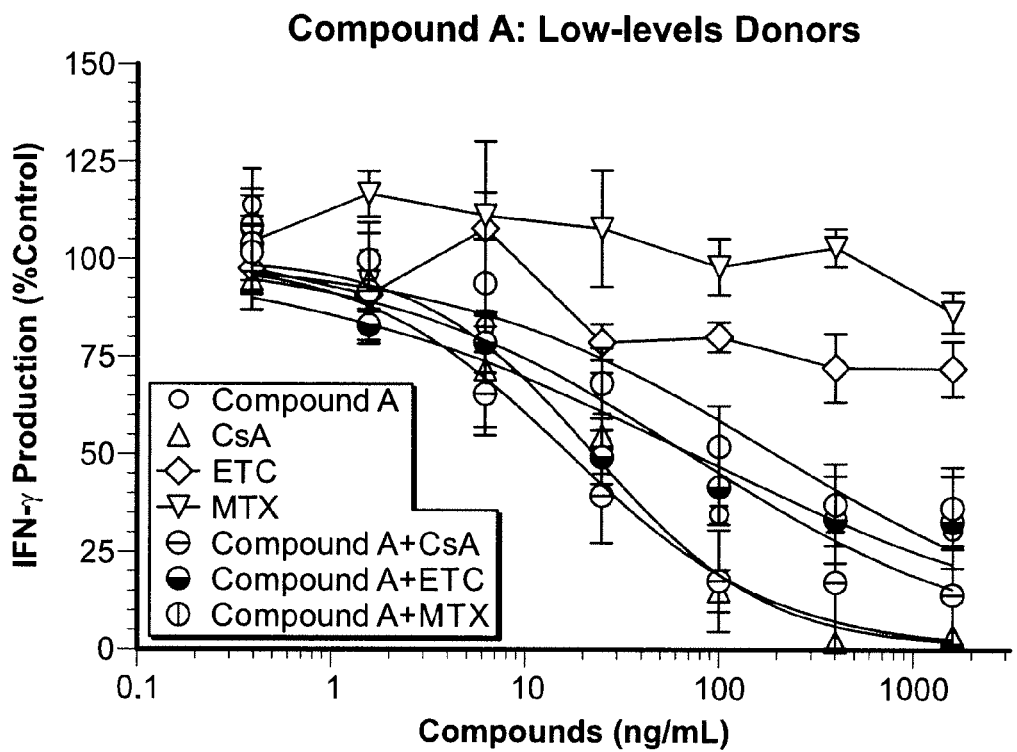
Figure 12B:
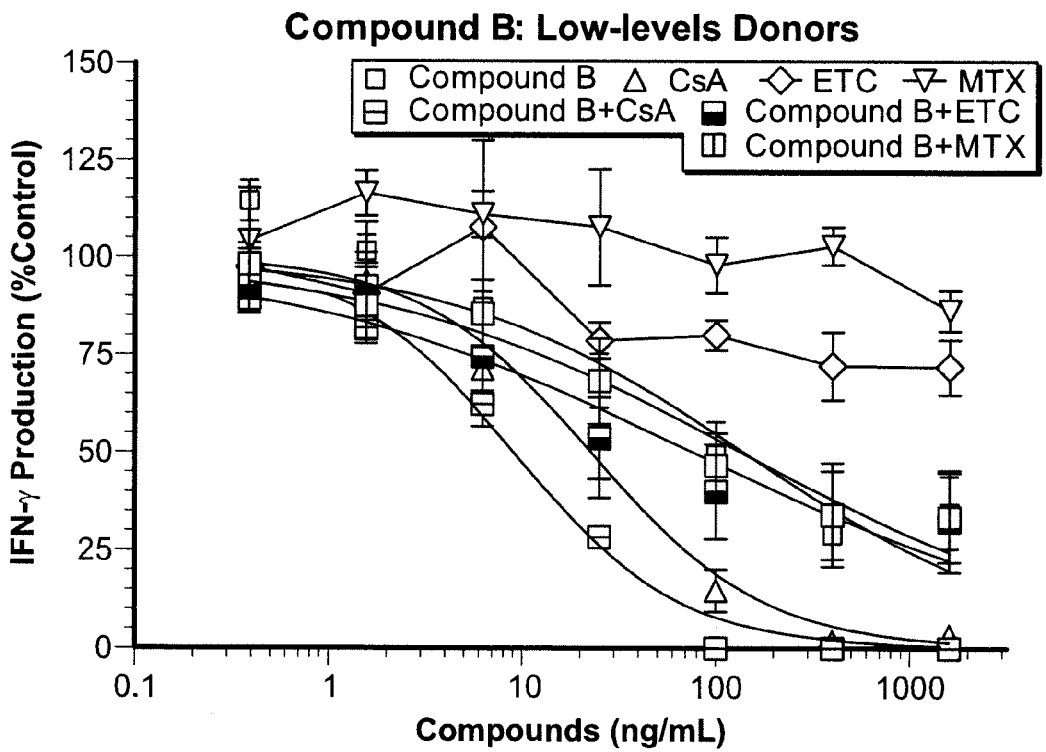

FIG. 12. shows interferon-gamma production in response to PDE4 inhibitors in combination with cyclosporine, Etanercept or methotrexate.

Figure 13A:
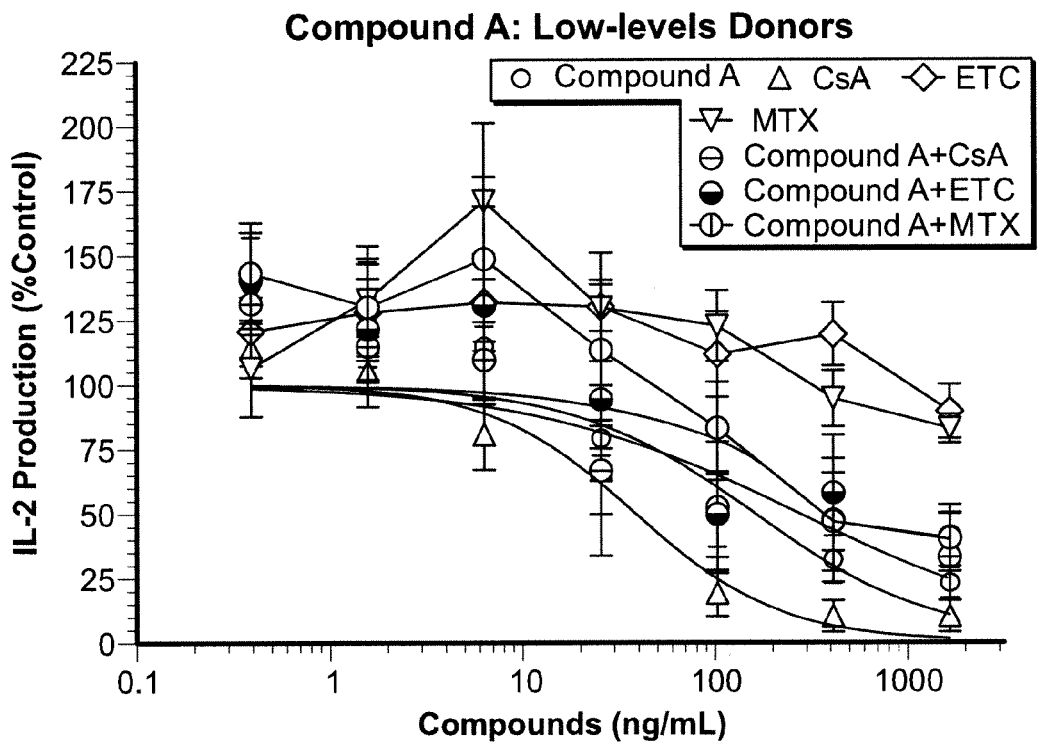
Figure 13B:
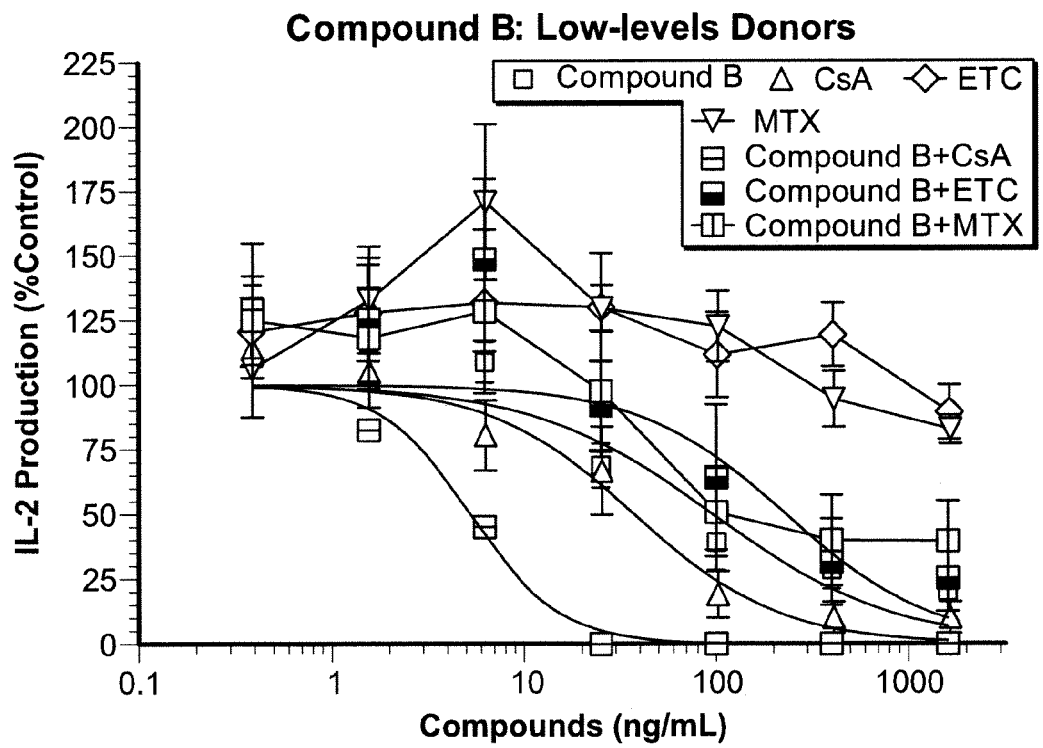

FIG. 13. shows interleukin-2 production in response to PDE4 inhibitors in combination with cyclosporine, Etanercept or methotrexate.

Figure 14A:
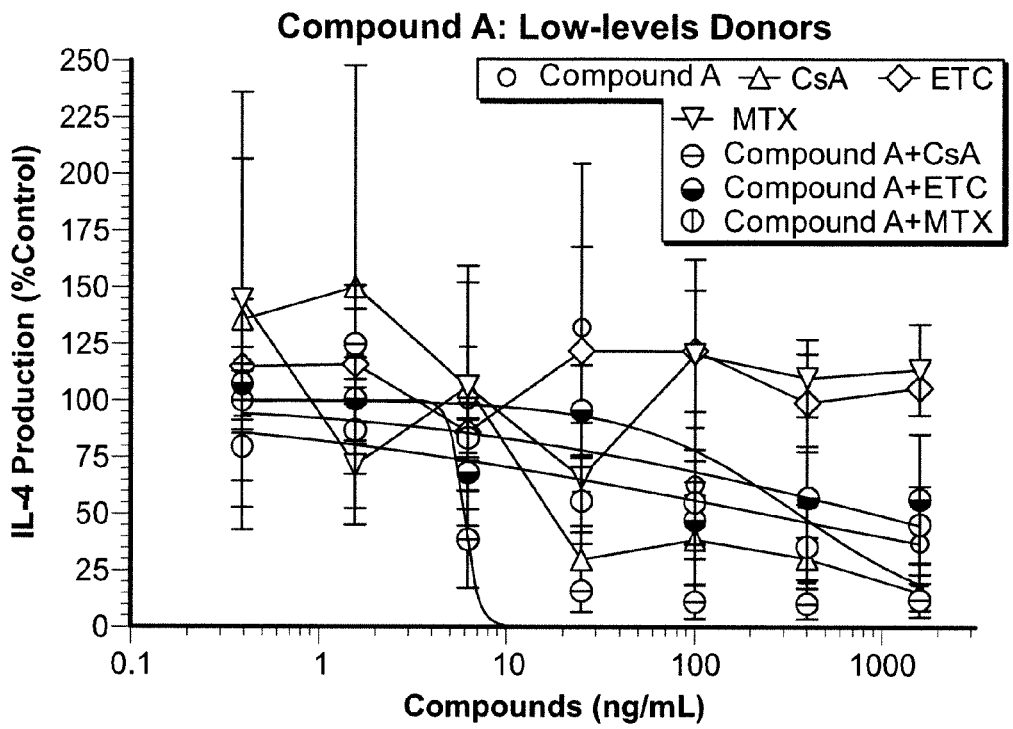
Figure 14B:
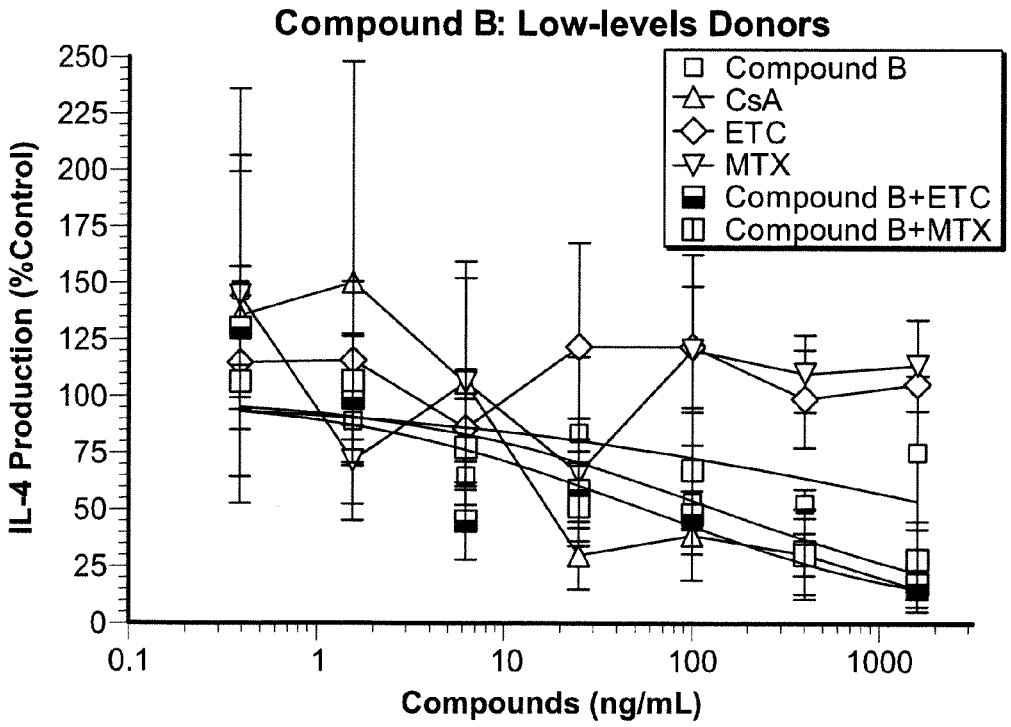

FIG. 14. shows interleukin 4 production in response to PDE4 inhibitors in combination with cyclosporine, Etanercept or methotrexate.

Figure 15A:
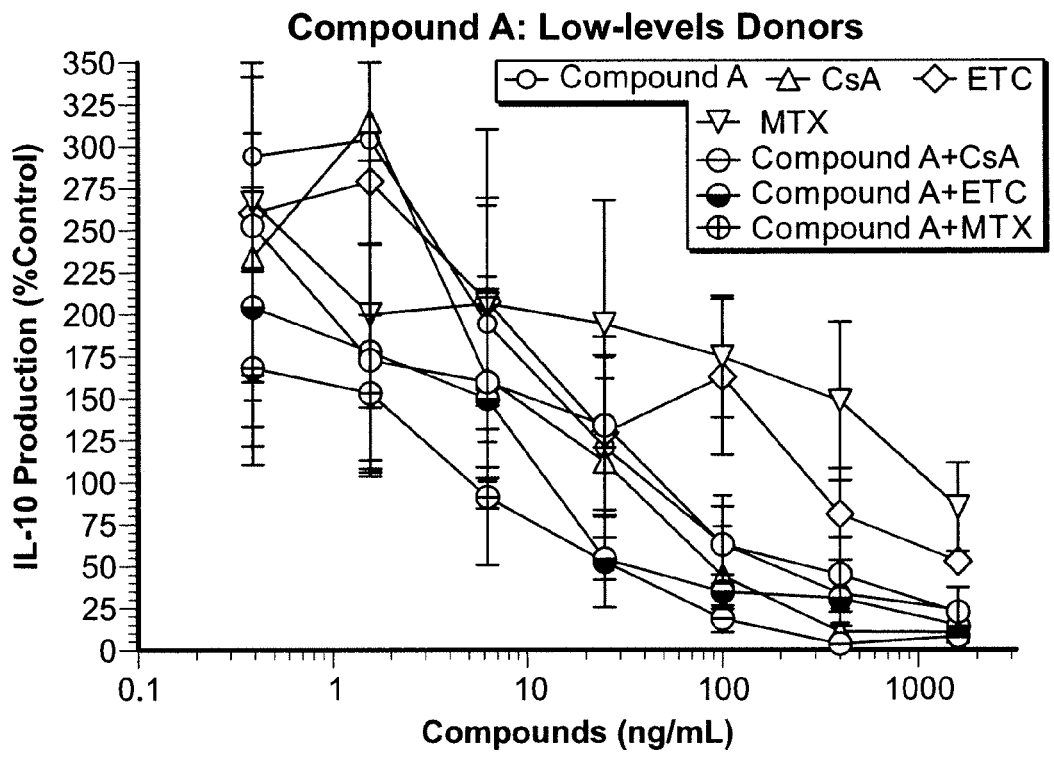
Figure 15B:
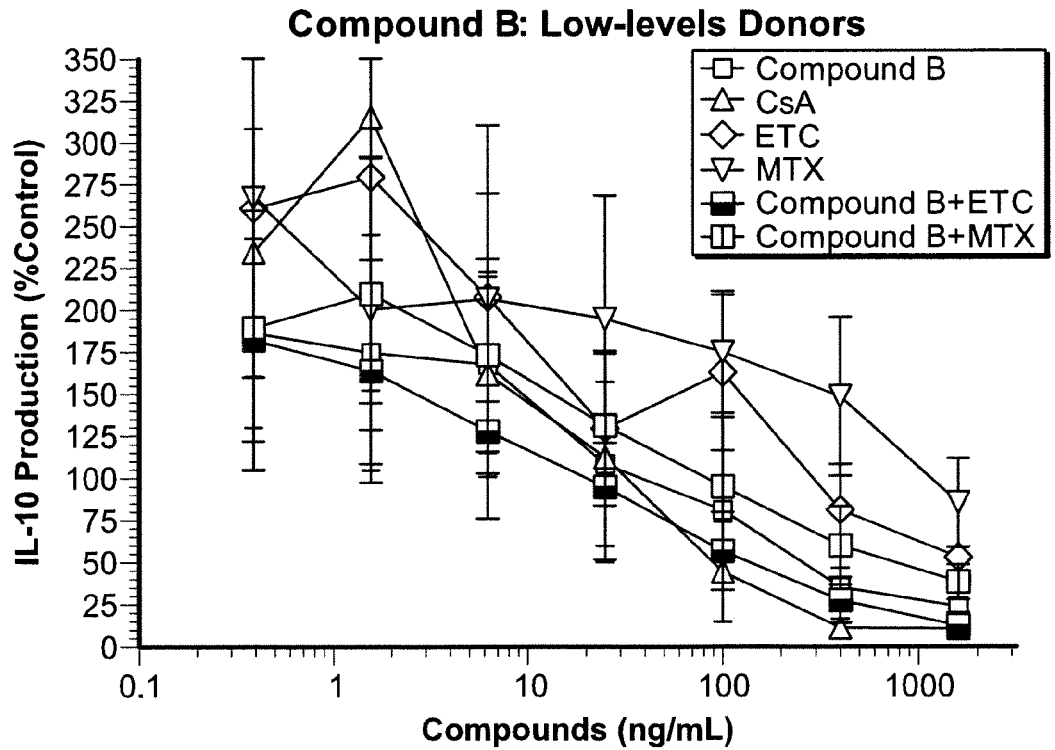

FIG. 15. shows Interleukin-10 production in response to PDE4 Inhibitors in combination with cyclosporine, Etanercept or methotrexate.

Figure 16A:
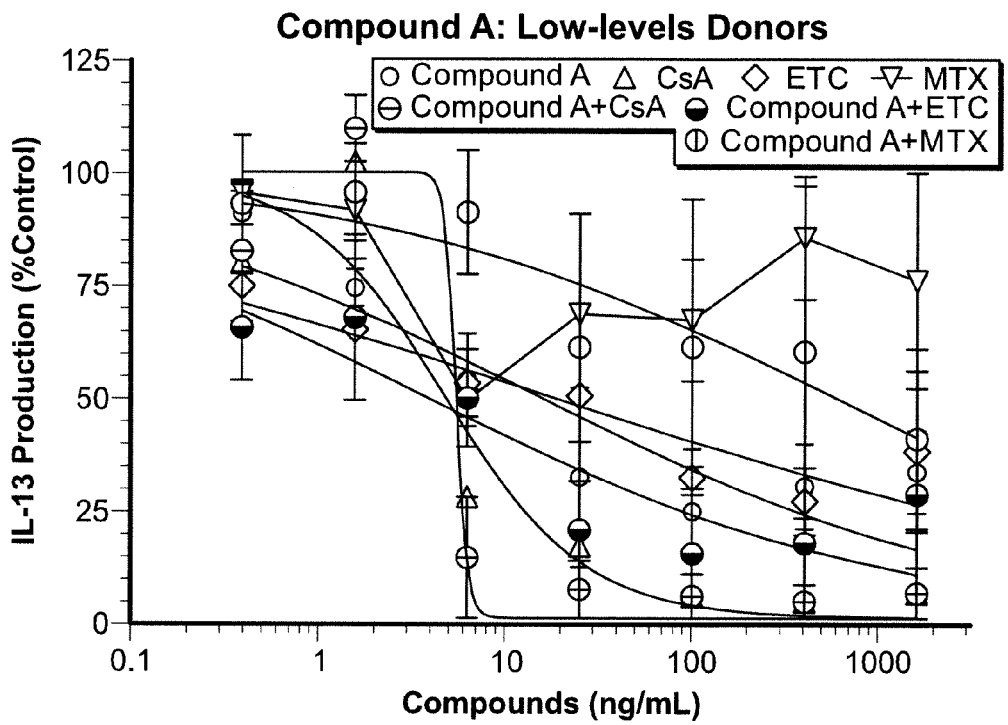
Figure 16B:
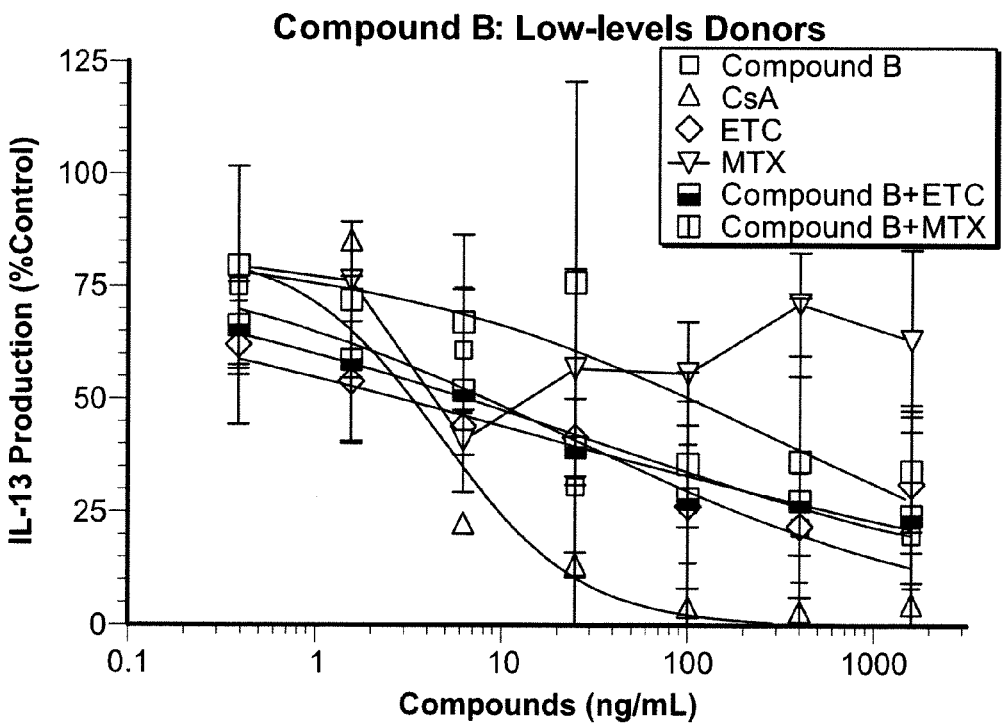

FIG. 16. shows interleukin-13 production in response to PDE4 inhibitors in combination with cyclosporine, Etanercept or methotrexate.

Figure 17A:
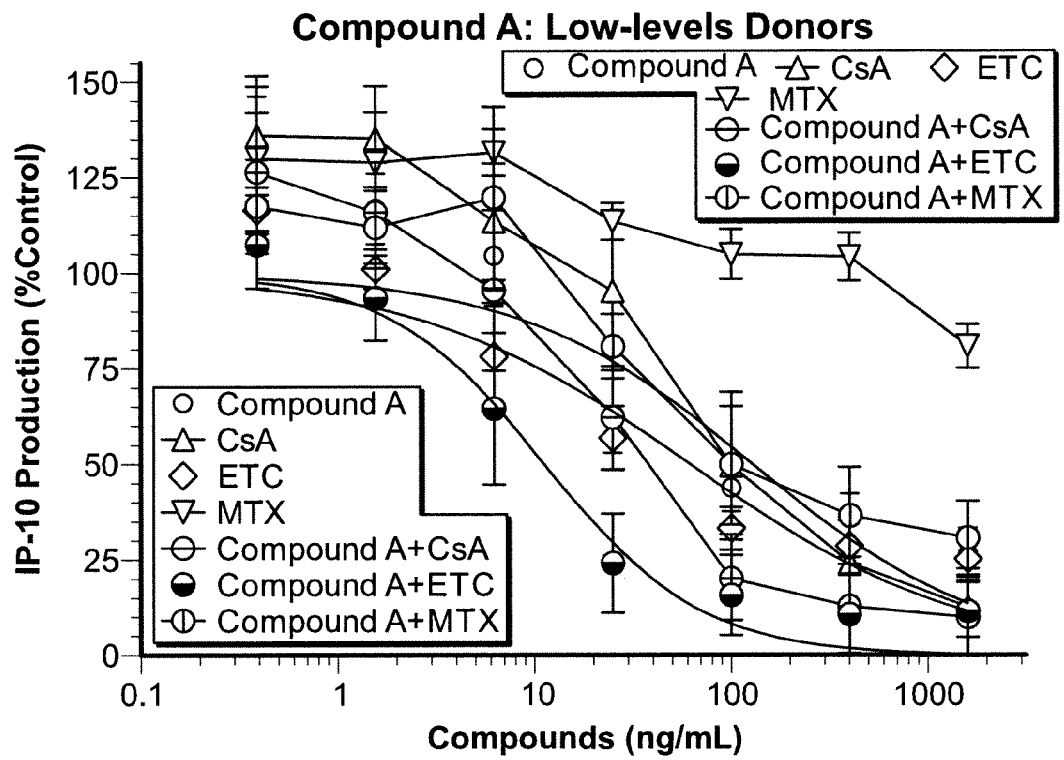
Figure 17B:
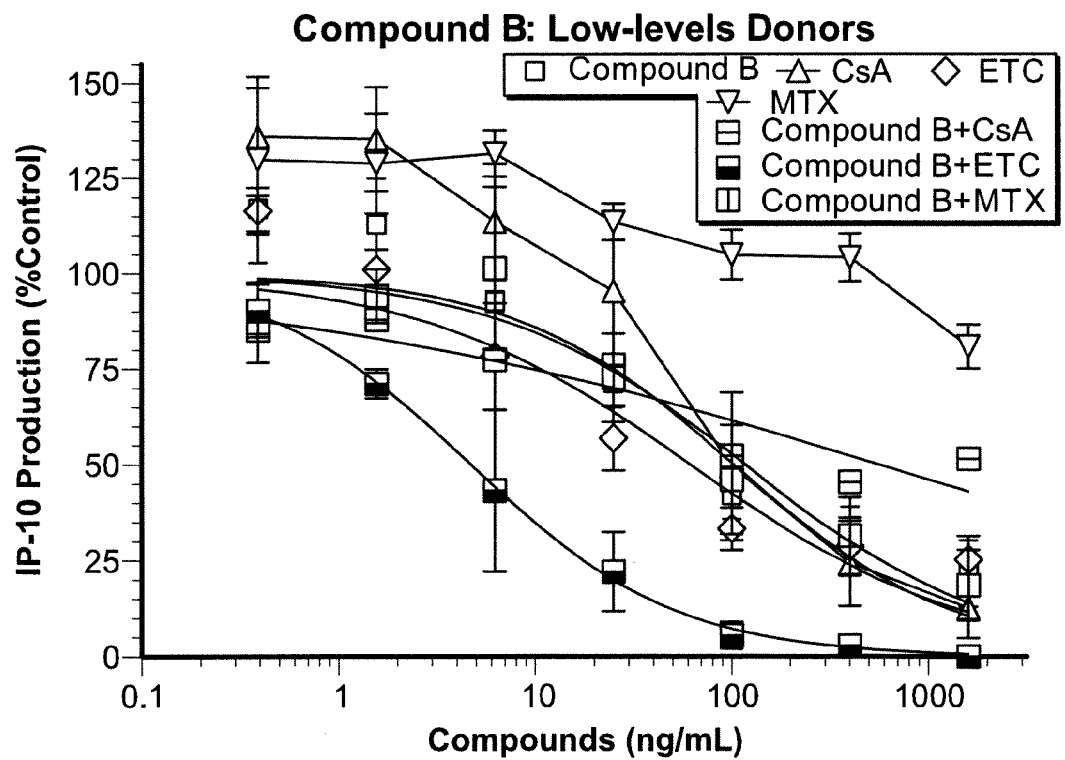

FIG. 17. shows interferon-inducible protein 10 production in response to PDE4 inhibitors in combination with cyclosporine, Etanercept or methotrexate.

Figure 18A:
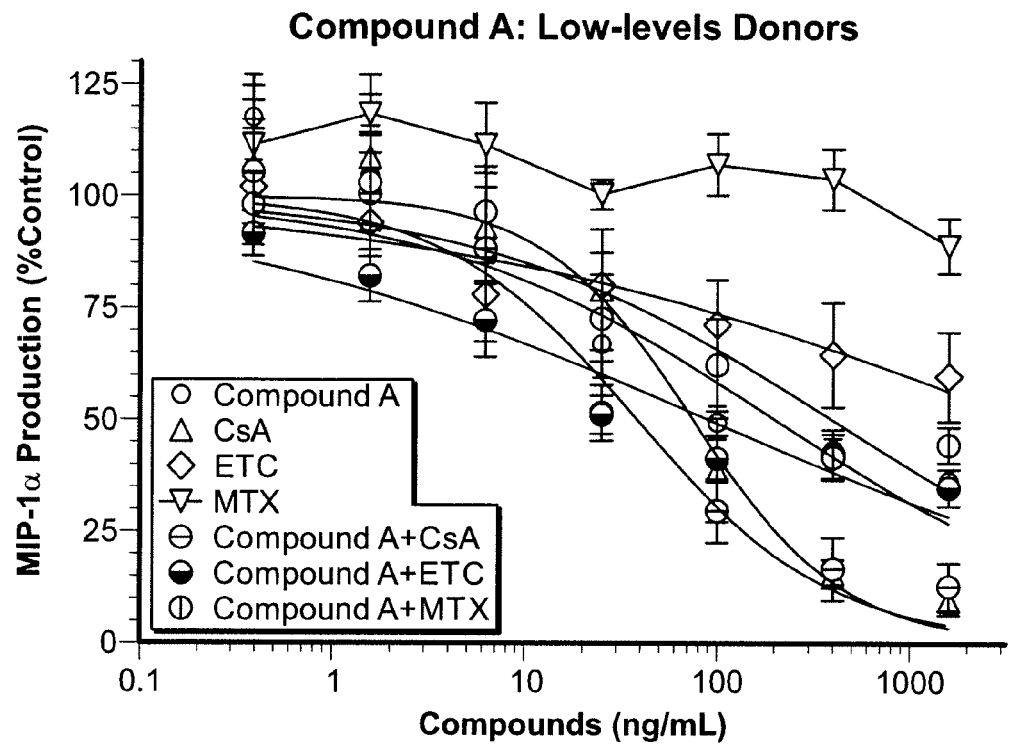
Figure 18B:
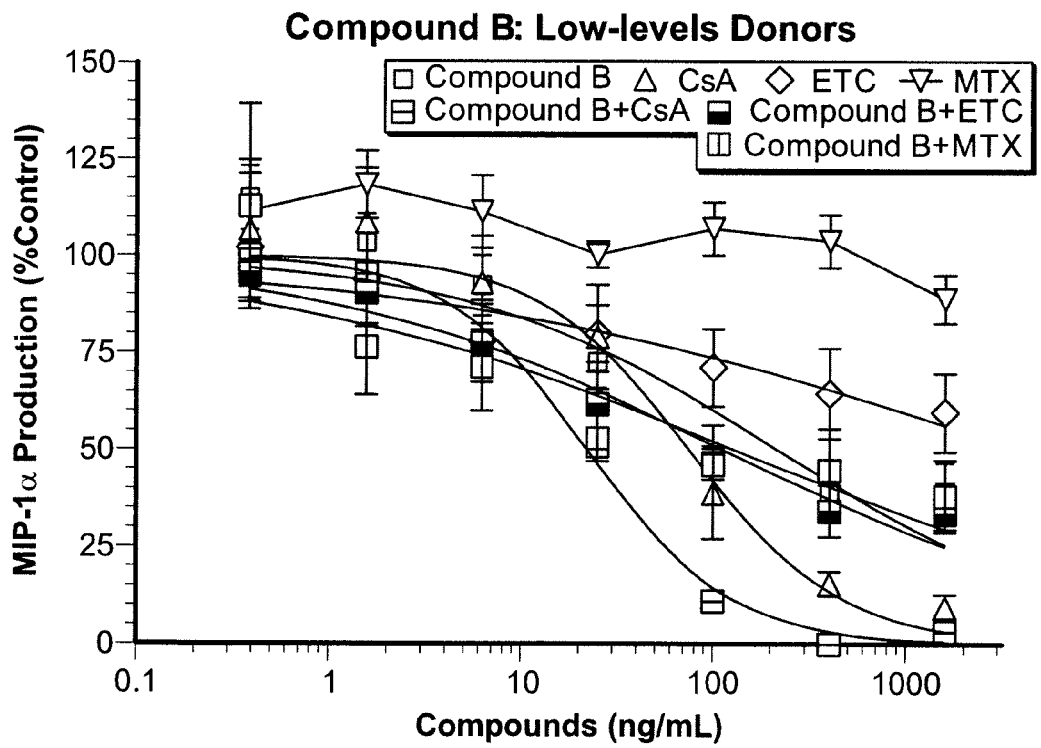

FIG. 18. shows macrophage inflammatory protein-1 alpha production in response to PDE4 inhibitors in combination with cyclosporine, Etanercept or methotrexate.

Figure 19A:
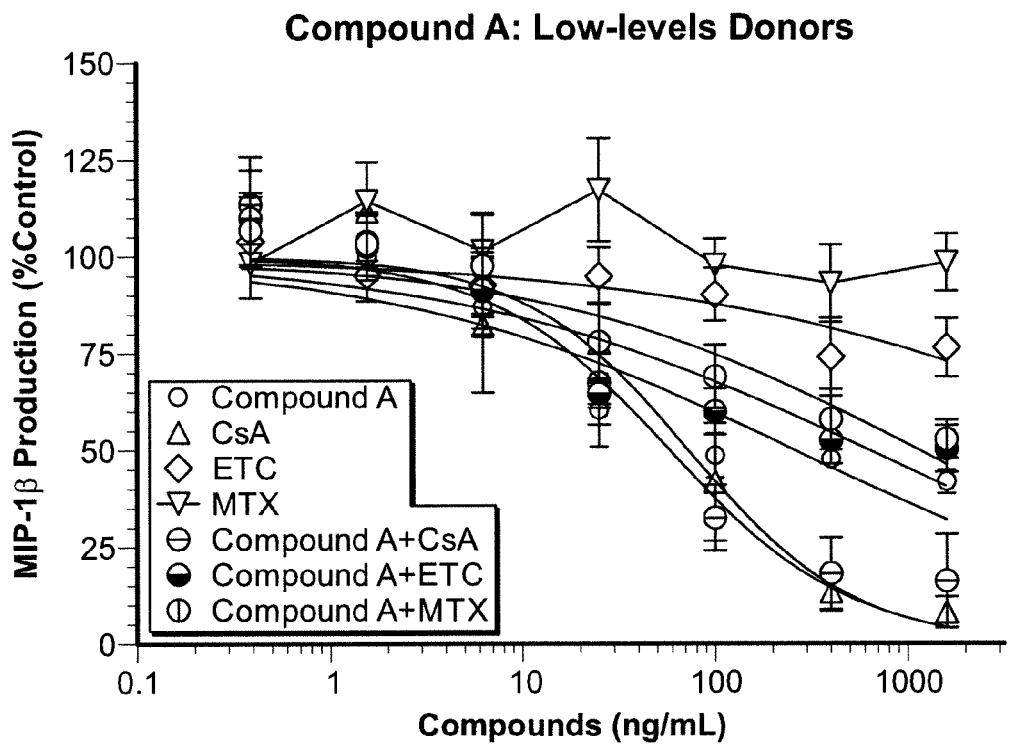
Figure 19B:
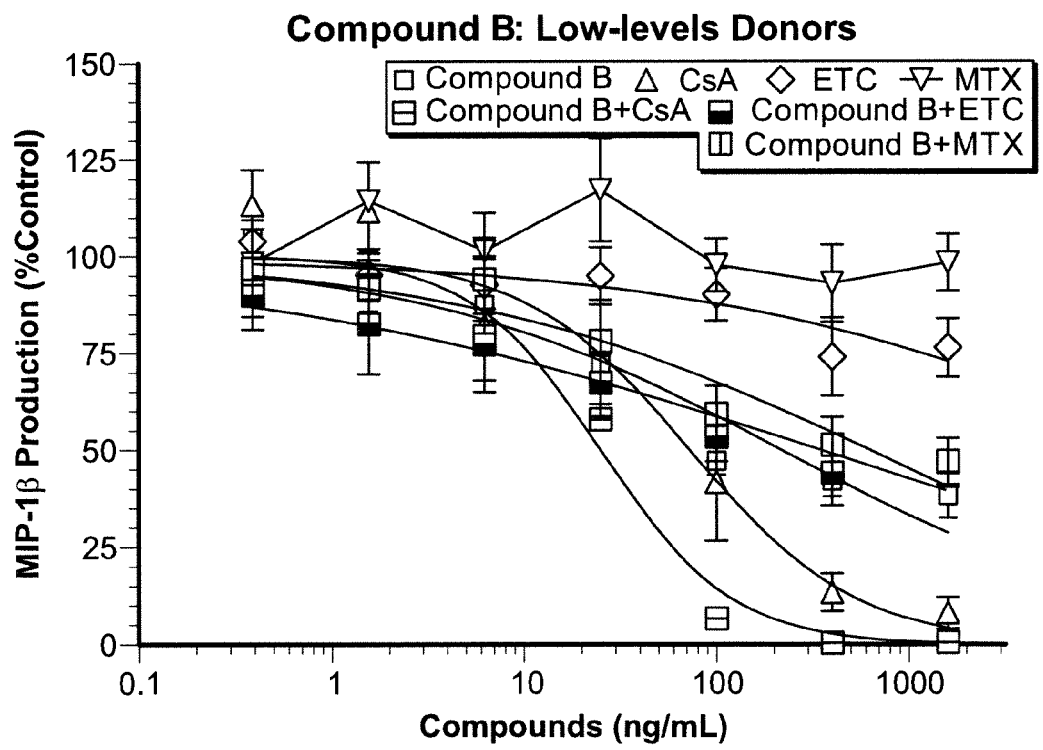

FIG. 19. shows macrophage inflammatory protein-1 beta production in response to PDE4 inhibitors in combination with cyclosporine, Etanercept or methotrexate.

Figure 20A:
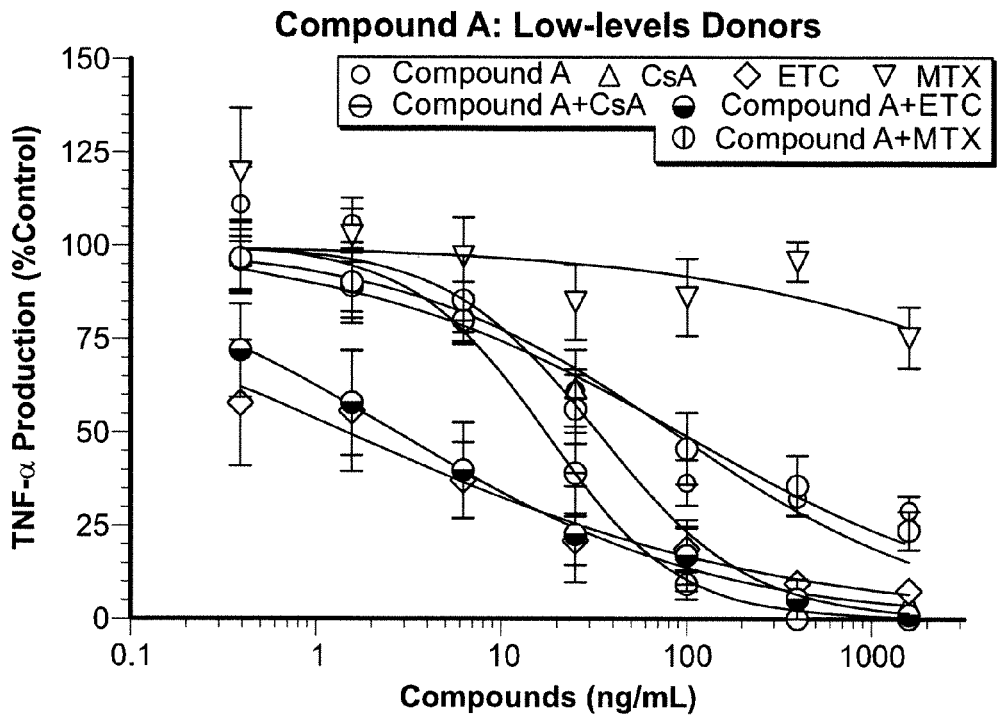
Figure 20B:
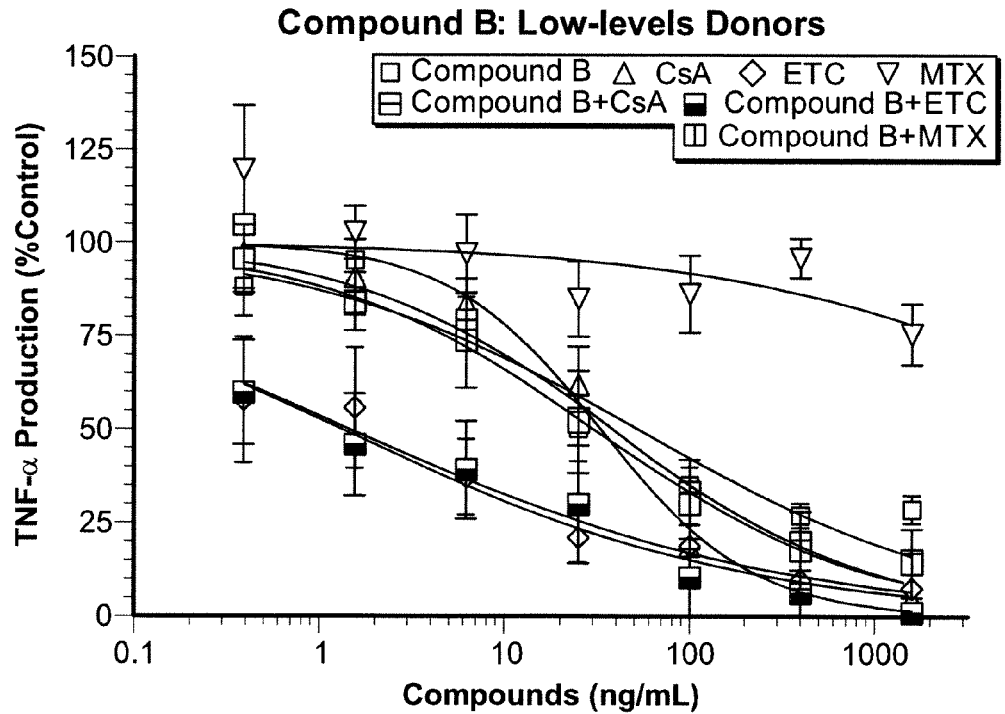

FIG. 20. shows TNF-α production in response to PDE4 inhibitors in combination with cyclosporine, Etanercept or methotrexate.

Figure 21A:
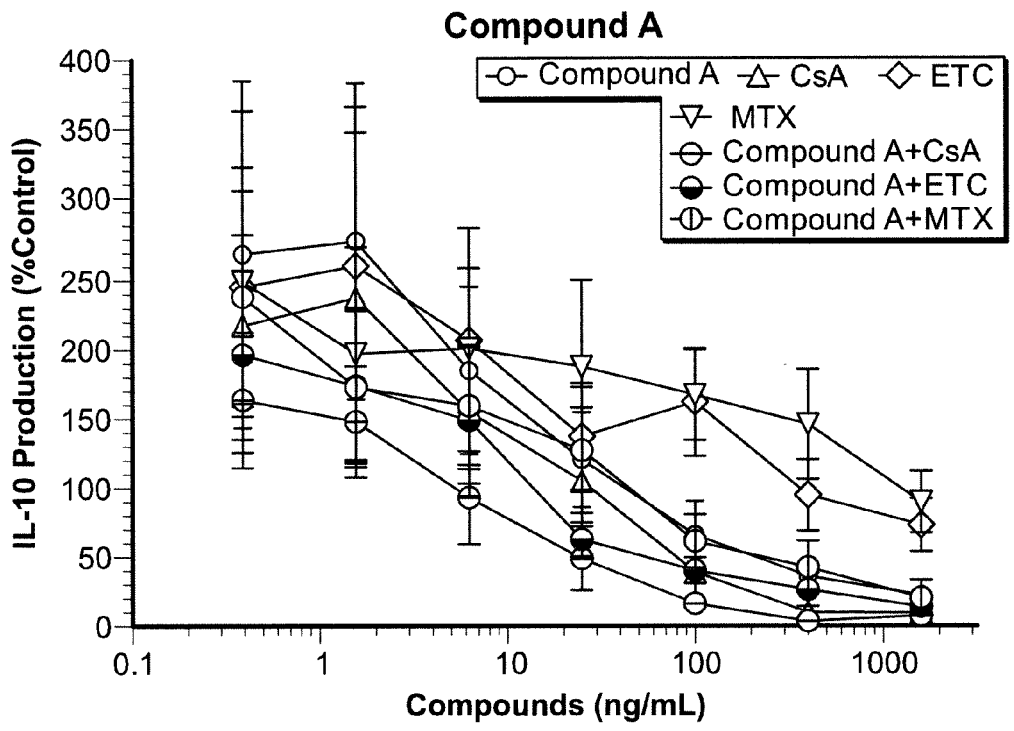
Figure 21B:
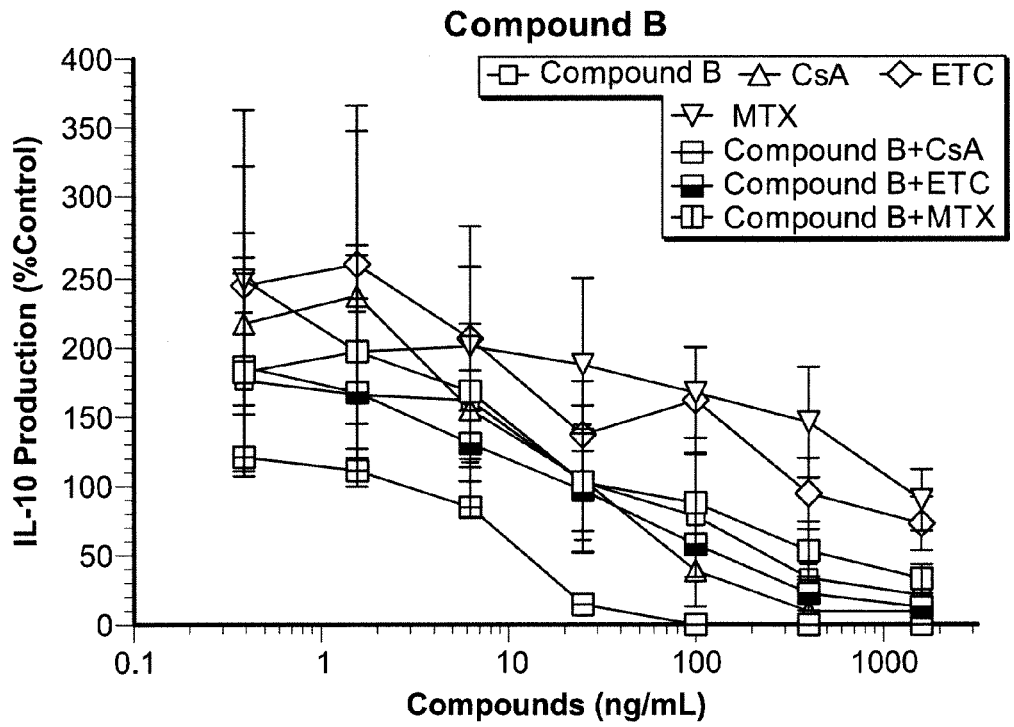

FIG. 21. shows interleukin-10 production in response to PDE4 inhibitors in combination with cyclosporine, Etanercept or methotrexate in staphylococcal enterotoxin B-treated perpherial blood mononuclear cells.

Figure 22A:
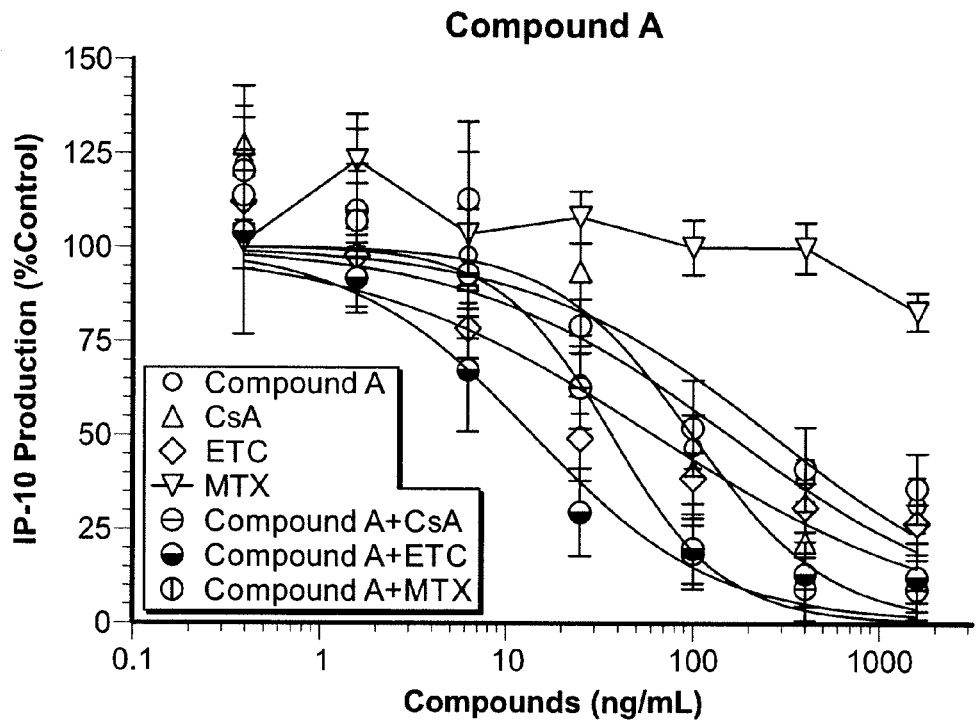
Figure 22B:
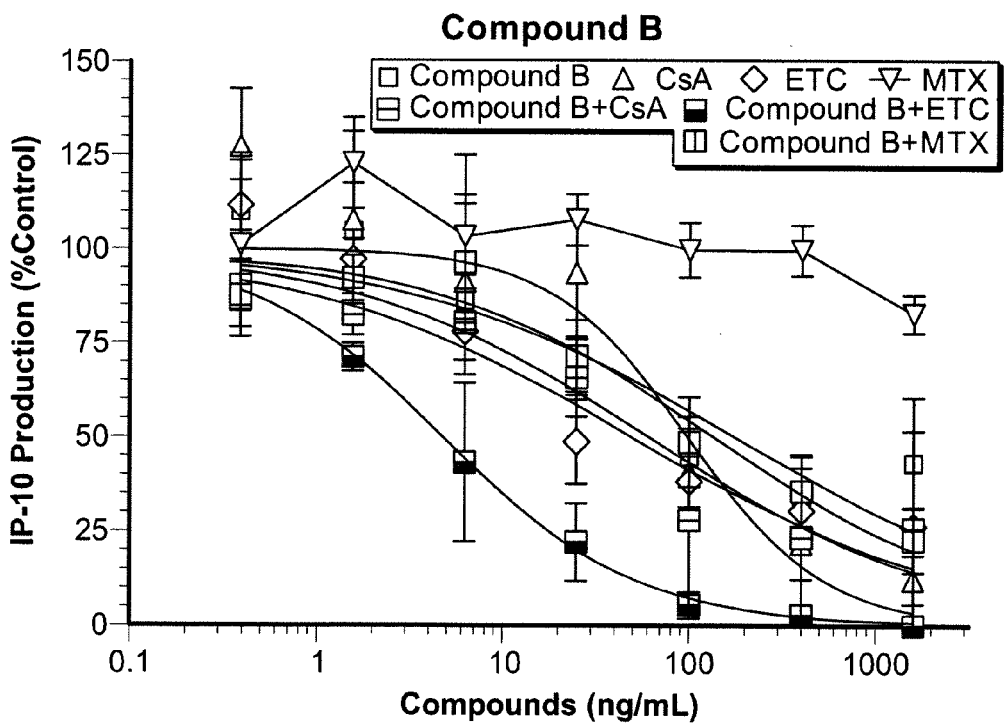

FIG. 22. shows interferon-inducible protein-10 production in response to PDE4 inhibitors in combination with cyclosporine, Etanercept or methotrexate in staphylococcal enterotoxin B-treated peripheral blood mononuclear cells.

Figure 23A:
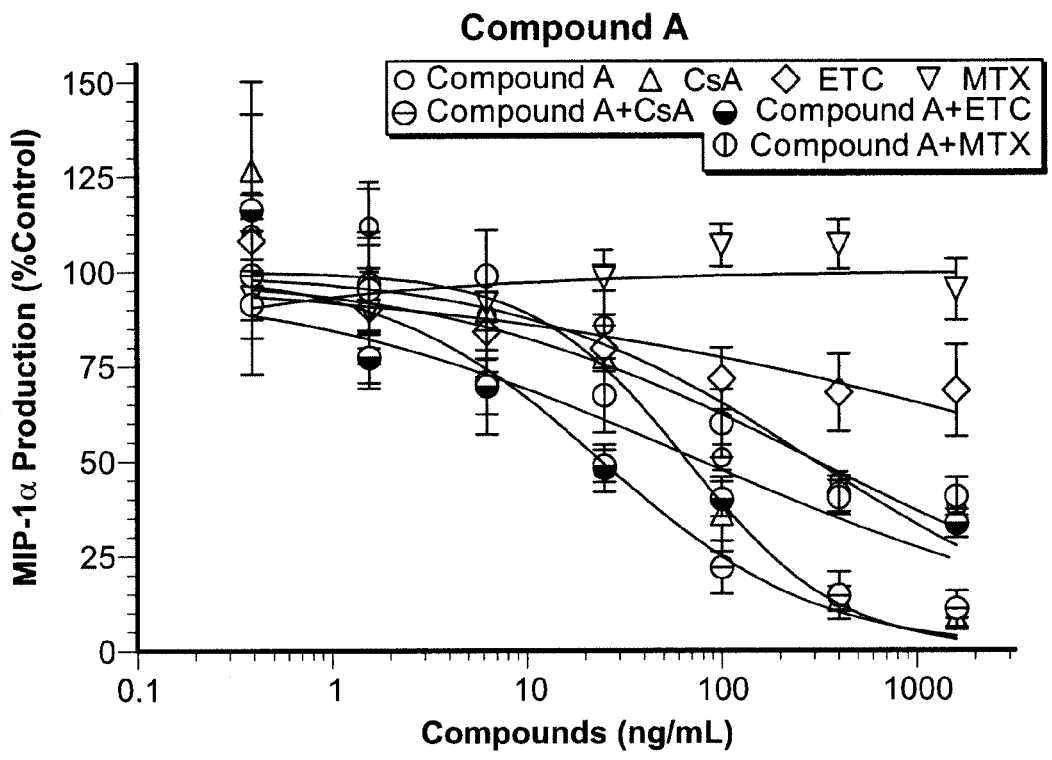
Figure 23B:
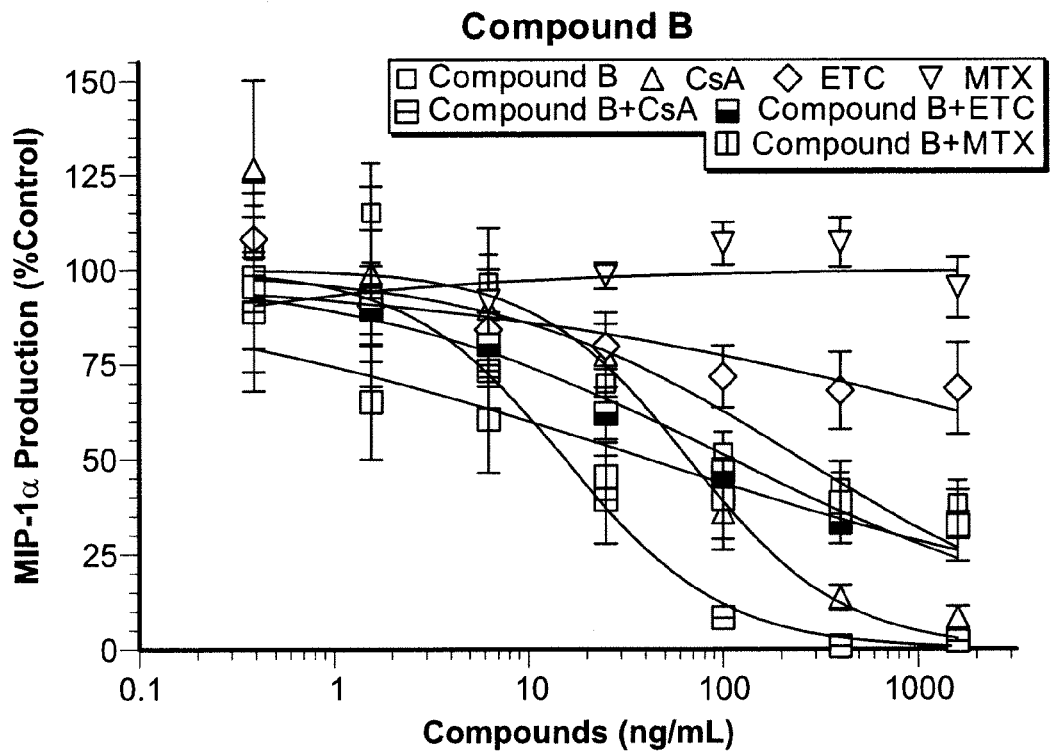

FIG. 23. shows macrophage inflammatory protein-1 alpha production in response to PDE4 inhibitors in combination with cyclosporine, Etanercept or methotrexate in staphylococcal enterotoxin B-treated peripheral blood mononuclear cells.

Figure 24A:
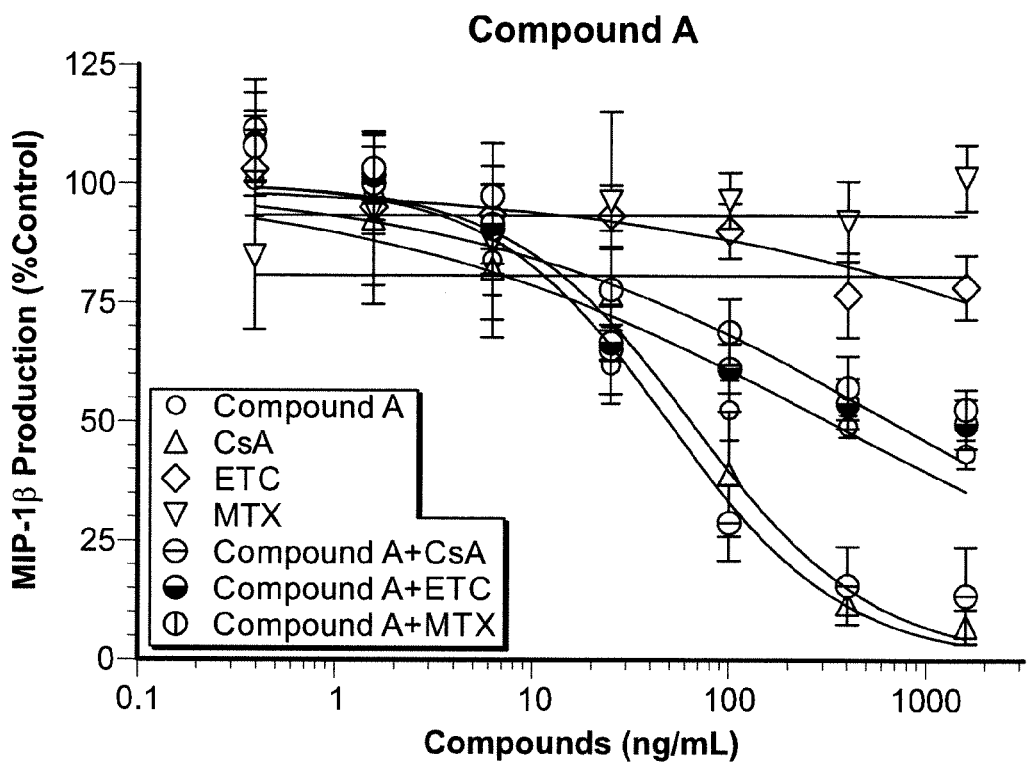
Figure 24B:
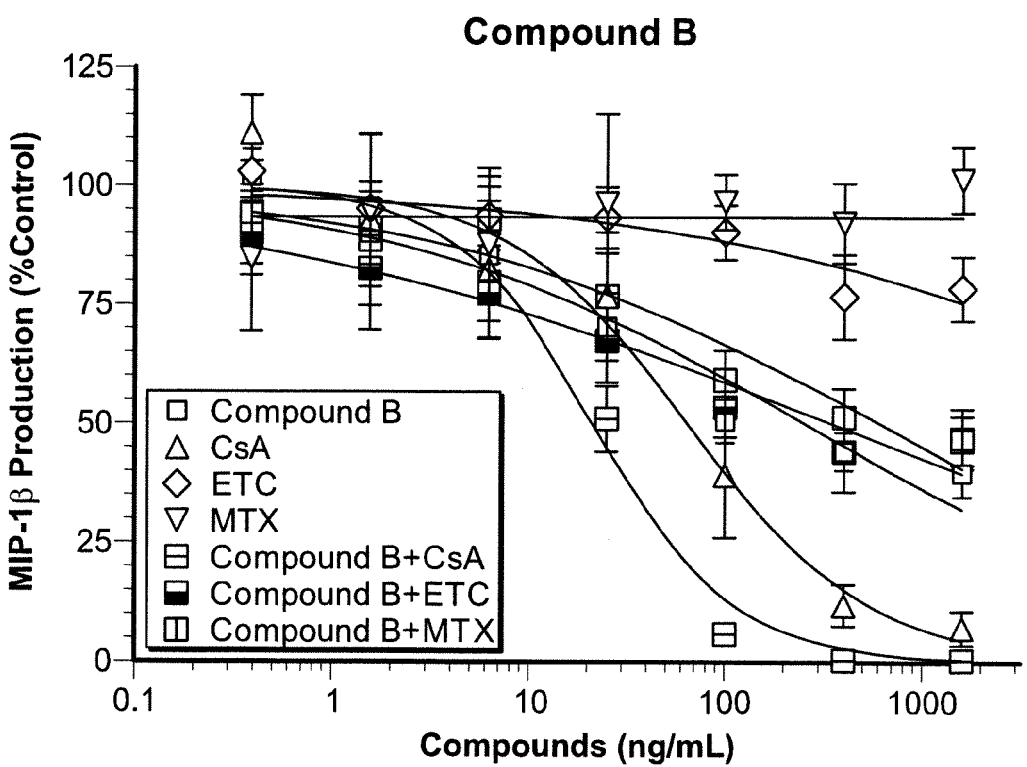

FIG. 24. shows macrophage inflammatory protein-1 beta production in response to PDE4 inhibitors in combination with cyclosporine, Etanercept or methotrexate in staphylococcal enterotoxin B-treated peripheral blood mononuclear cells.

Figure 25A:
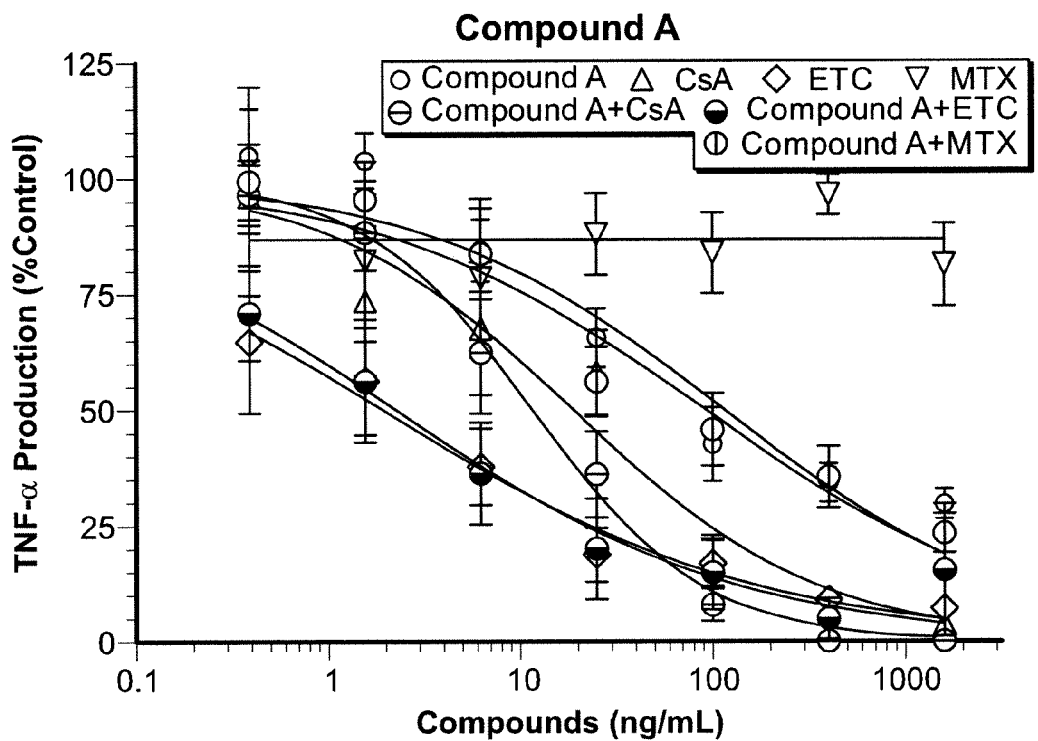

FIG. 25. shows TNF-α production in response to PDE4 inhibitors in combination with cyclosporine, Etanercept or methotrexate in staphylococcal enterotoxin B-treated peripheral blood mononuclear cells.

Figure 26:
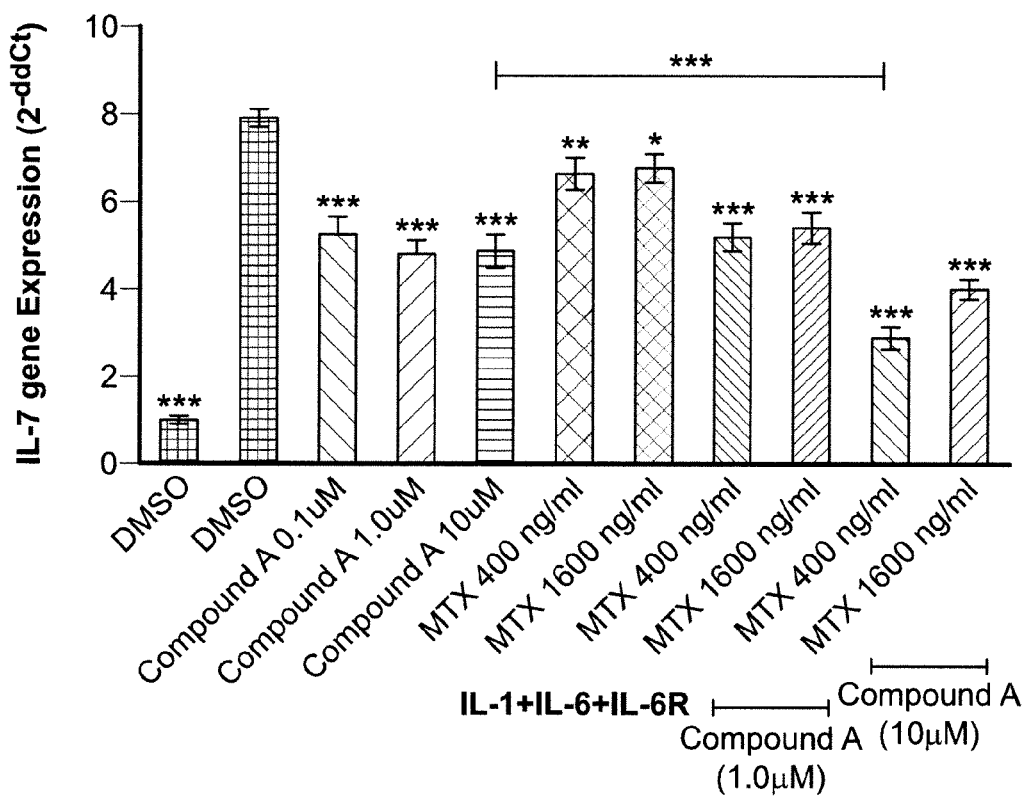

FIG. 26. shows IL-7 production in response to Compound A, alone and in combination with methotrexate.

Figure 27:
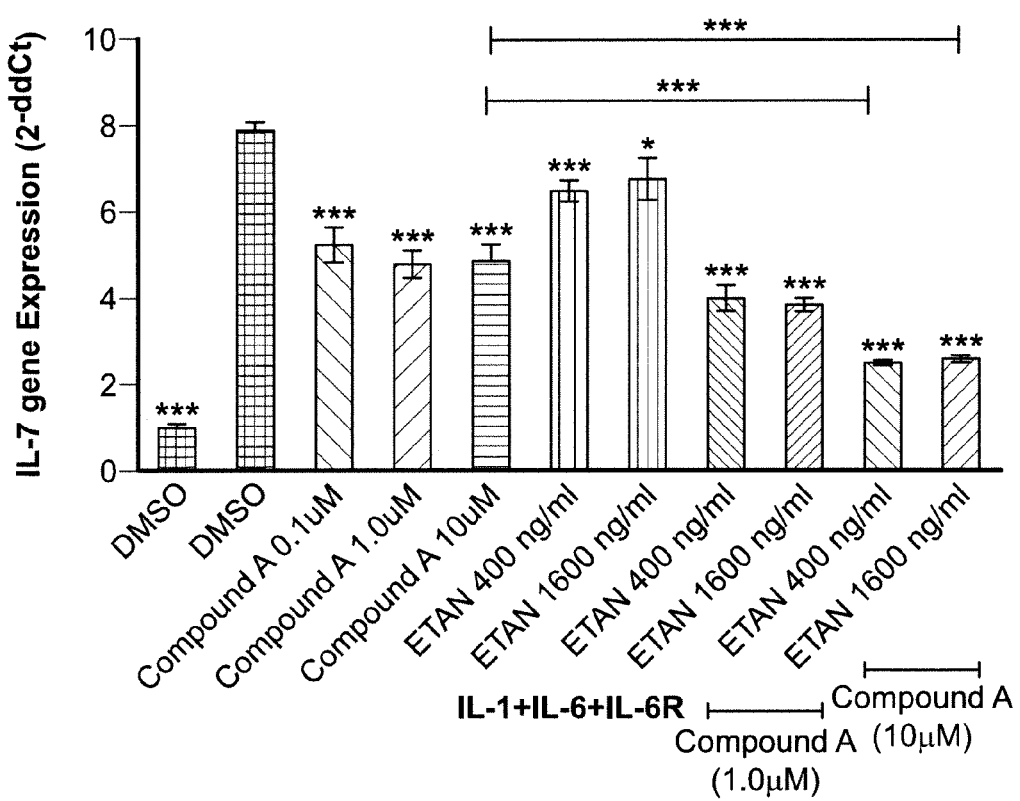

FIG. 27. shows IL-7 production in response to Compound A, alone and in combination with Etanercept.

Figure 28:
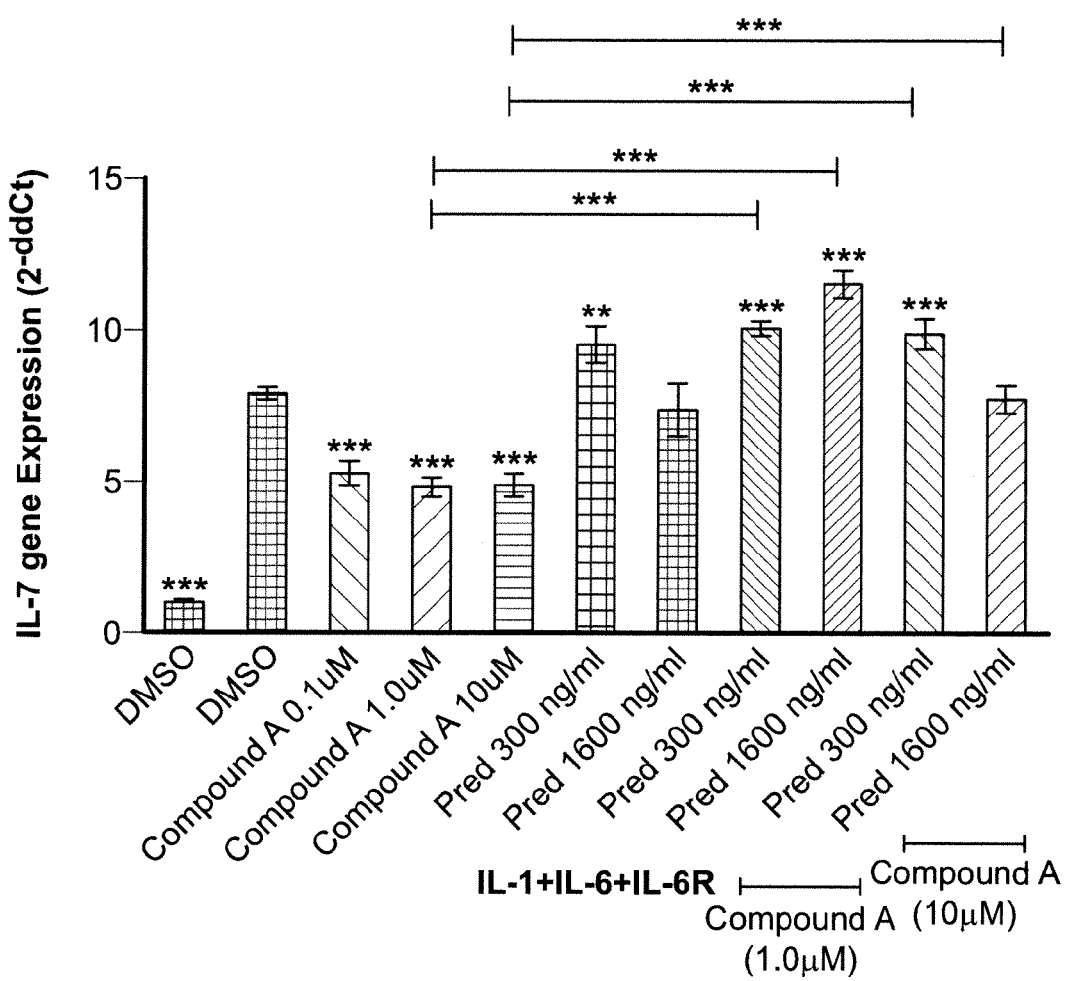

FIG. 28. shows IL-7 production in response to Compound A, alone and in combination with prednisone.

5. DETAILED DESCRIPTION

5.1. Combination Therapies Comprising PDE4 Inhibitors for Inflammation

Provided herein are methods of treating, managing or preventing psoriasis and/or arthritis, including but not limited to psoriatic arthritis and rheumatoid arthritis, which comprises administering to a patient in need of such treatment, management, or prevention, a therapeutically or prophylactically effective amount of Compound A, which is the (+) enantiomer of 2-[1-(3-ethoxy-4-methoxyphenyl)-2-methylsulfonylethyl]-4-acetylaminoisoindoline-1,3-dione, also known as Apremilast, or a pharmaceutically acceptable prodrug, metabolite, polymorph, salt, solvate or clathrate thereof, in combination with a second active agent. Without being limited by theory, the (+) enantiomer of 2-[1-(3-ethoxy-4-methoxyphenyl)-2-methylsulfonylethyl]-4-acetylaminoisoindoline-1,3-dione is believed to be (S)-N-(2-(1-(3-ethoxy-4-methoxyphenyl)-2-(methylsulfonyl)ethyl)-1,3-dioxoisoindolin-4-yl)acetamide, which has the following structure:

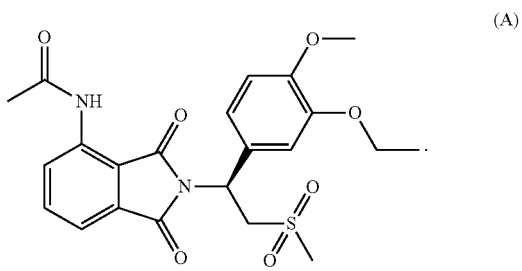 [SMILES: CCOc1cc([C@@H](CS(C)(=O)=O)N2C(=O)c3cccc(NC(C)=O)c3C2=O)ccc1OC ; "."]

(A)

Compound A can be prepared according to methods disclosed in U.S. Pat. No. 6,962,940, titled "(+)-2-[1-(3-Ethoxy-4-methoxyphenyl)-2-methylsulfonylethyl]-4-acetylaminoisoindoline-1,3-dione: Methods Of Using And Compositions Thereof," or U.S. Patent Publication No. 2010/0168475, each of which are incorporated herein by reference. Generally, racemic 2-[1-(3-ethoxy-4-methoxyphenyl)-2-methylsulfonylethyl]-4-acetylaminoisoindoline-1,3-dione can be readily prepared using the methods described in U.S. Pat. No. 6,020,358, which is incorporated herein by reference. The corresponding (+) enantiomer can be isolated from the racemic compound by techniques known in the art. Examples include, but are not limited to, the formation of chiral salts and the use of chiral or high performance liquid chromatography "HPLC" and the formation and crystallization of chiral salts. See, e.g., Jacques, J., et al., *Enantiomers, Racemates and Resolutions* (Wiley Interscience, New York, 1981); Wilen, S. H., et al., *Tetrahedron* 33:2725 (1977); Eliel, E. L., *Stereochemistry of Carbon Compounds* (McGraw Hill, N.Y., 1962); and Wilen, S. H., *Tables of Resolving Agents and Optical Resolutions* p. 268 (E. L. Eliel, Ed., Univ. of Notre Dame Press, Notre Dame, 1N, 1972).

In a specific method, the (+) enantiomer of 2-[1-(3-ethoxy-4-methoxyphenyl)-2-methylsulfonylethyl]-4-acetylaminoisoindoline-1,3-dione is synthesized from 3-acetamidophthalic anhydride and a chiral amino acid salt of (S)-2-(3-ethoxy-4-methoxyphenyl)-1-(methylsulphonyl)-eth-2-ylamine. Chiral amino acid salts of (S)-2-(3 ethoxy-4-methoxyphenyl)-1-(methylsulphonyl)-eth-2-ylamine include, but are not limited to salts formed with the L isomers of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, ornithine, 4-aminobutyric acid, 2-aminoisobutyric acid, 3-aminopropionic acid, ornithine, norleucine, norvaline, hydroxyproline, sarcosine, citrulline, cysteic acid, t-butylglycine, t-butylalanine, phenylglycine, cyclohexylalanine, and N-acetyl-L-leucine. A specific chiral amino acid salt is (S)-2-(3-ethoxy-4-methoxyphenyl)-1-(methylsulphonyl)-eth-2-ylamine N-acetyl-L-leucine salt, which is resolved from 2-(3-ethoxy-4-methoxyphenyl)-1-(methylsulphonyl)-eth-2-ylamine and N-acetyl-L-leucine in methanol.

Also provided herein are methods of treating, managing or preventing psoriasis and arthritis, including but not limited to psoriatic arthritis and rheumatoid arthritis, which comprises administering to a patient in need of such treatment, management, or prevention, a therapeutically or prophylactically effective amount of Compound B, which refers to enantiomerically pure cyclopropanecarboxylic acid {2-[(1S)-1-(3-ethoxy-4-methoxy-phenyl)-2-methanesulfonyl-ethyl]-3-oxo-2,3-dihydro-1H-isoindol-4-yl}-amide, in combination with a second active agent. Without being limited by theory, Compound B is believed to be (S)-N-(2-(1-(3-ethoxy-4- methoxyphenyl)-2-(methylsulfonyl)ethyl)-3-oxoisoindolin-4-yl)cyclopropanecarboxamide, which has the following structure:

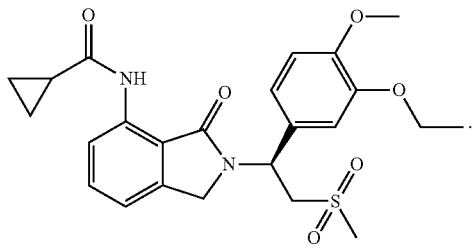

(B)

In some embodiments, either one of the PDE4 inhibitors (S)-N-(2-(1-(3-ethoxy-4-methoxyphenyl)-2-(methylsulfonyl)ethyl)-1,3-dioxoisoindolin-4-yl)acetamide ("Compound A") or (S)-N-(2-(1-(3-ethoxy-4-methoxyphenyl)-2-(methylsulfonyl)ethyl)-3-oxoisoindolin-4-yl)cyclopropanecarboxamide ("Compound B") is combined with a second active agent selected from anti-TNF biologics such as etanercept, infliximab, adalimumab, golimumab, or certolizumab; calcineurin inhibitors such as cyclosporine A, tacrolimus, and vaclosporin; corticosteroids such as prednisone, methylprednisone, dexamethasone, betamethasone, triamcinolone, beclometasone, fludrocortisones, deoxycorticosterone, and aldosterone; and/or antimetabolites such as methotrexate for the treatment of inflammatory and immune diseases involving T cells, chondrocytes, and synoviocytes. In certain embodiments, the inflammatory or immune diseases are selected from rheumatoid arthritis, spondyloarthritis (including psoriatic arthritis and ankylosing spondylitis), osteoarthritis, psoriasis, atopic dermatitis, Behcet's disease, inflammatory bowel disease, Crohn's disease, ulcerative colitis, cutaneous lupus erythematosus, and systemic lupus erythematosus. In one embodiment, the disease is rheumatoid arthritis or psoriasis.

In some embodiments, the combination of either one of the PDE4 inhibitors (S)-N-(2-(1-(3-ethoxy-4-methoxyphenyl)-2-(methylsulfonyl)ethyl)-1,3-dioxoisoindolin-4-yl)acetamide ("Compound A") or (S)-N-(2-(1-(3-ethoxy-4-methoxyphenyl)-2-(methylsulfonyl)ethyl)-3-oxoisoindolin-4-yl) cyclopropanecarboxamide ("Compound B") with at least one of either cyclosporine A ("CsA"), etanercept ("ETC" or "ETN"), or methotrexate ("MTX") provides synergistic effects for the inhibition of cytokines associated with rheumatoid arthritis and psoriasis. As provided herein, the determination of whether the addition of either one of Compound A or Compound B augmented the inhibition of cytokine production relative to that produced by CsA, MTX, or ETC alone was assessed in human anti-CD3 monoclonal antibody (mAb)-stimulated T cells and staphylococcal enterotoxin B (SEB)-treated PBMCs. The cytokines profiled include interferon-gamma (IFN-γ), interleukin (IL)-2, IL-4, IL-10, IL-13, interferon-inducible protein 10 (IP-10), macrophage inflammatory protein-1 alpha (MIP-1α) and macrophage inflammatory protein-1 beta (MIP-1β) and tumor necrosis factor-alpha (TNF-α).

5.2. Definitions

As used herein, the term "Compound A" refers to an enantiomerically pure form of 2-[1-(3-ethoxy-4-methoxyphenyl)-2-methylsulfonylethyl]-4-acetylaminoisoindoline-1,3-dione, also known as Apremilast, and which when dissolved in methanol rotates plane polarized light in the (+) direction. Without being limited by theory, Compound A is believed to be (S)-N-(2-(1-(3-ethoxy-4-methoxyphenyl)-2-(methylsulfonyl)ethyl)-1,3-dioxoisoindolin-4-yl)acetamide, which has the following structure:

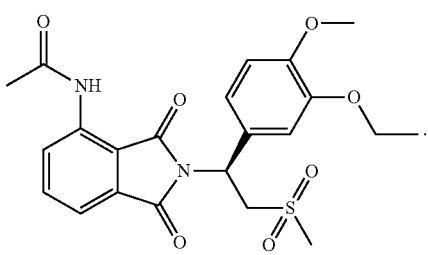

(A)

As used herein, the term "Compound B" refers to enantiomerically pure cyclopropanecarboxylic acid {2-[(1S)-1-(3-ethoxy-4-methoxy-phenyl)-2-methanesulfonyl-ethyl]-3-oxo-2,3-dihydro-1H-isoindol-4-yl}-amide. Without being limited by theory, Compound B is believed to be (S)-N-(2-(1-(3-ethoxy-4-methoxyphenyl)-2-(methylsulfonyl)ethyl)-3-oxoisoindolin-4-yl)cyclopropanecarboxamide, which has the following structure:

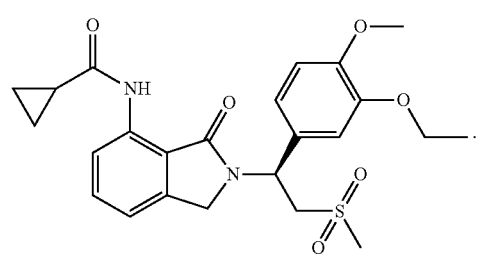

(B)

As used herein and unless otherwise indicated, the term "pharmaceutically acceptable salt" includes, but is not limited to, salts prepared from pharmaceutically acceptable non-toxic acids or bases including inorganic acids and bases and organic acids and bases. Suitable pharmaceutically acceptable base addition salts include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts.

As used herein and unless otherwise indicated, the term "hydrate" means a compound provided herein or a salt thereof, that further includes a stoichiometric or non-stoichiometric amount of water bound by non-covalent intermolecular forces.

As used herein and unless otherwise indicated, the term "solvate" means a solvate formed from the association of one or more solvent molecules to a compound provided herein. The term "solvate" includes hydrates (e.g., mono-hydrate, dihydrate, trihydrate, tetrahydrate and the like).

As used herein and unless otherwise indicated, the term "polymorph" means solid crystalline forms of a compound provided herein or complex thereof. Different polymorphs of the same compound can exhibit different physical, chemical and/or spectroscopic properties.

As used herein and unless otherwise specified, the term "prodrug" means a derivative of a compound that can hydrolyze, oxidize, or otherwise react under biological conditions (in vitro or in vivo) to provide the compound. Examples of prodrugs include, but are not limited to, derivatives and metabolites of (+)-2-[1-(3-ethoxy-4-methoxyphenyl)-2-methylsulfonylethyl]-4-acetylaminoisoindoline-1,3-dione that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Prodrugs can typically be prepared using well-known methods, such as those described by 1 *Burger's Medicinal Chemistry and Drug Discovery*, 172-178, 949-982 (Manfred E. Wolff ed., 5th ed. 1995).

As used herein, and unless otherwise specified, the term "enantiomer," "isomer" or "stereoisomer" encompasses all enantiomerically/stereomerically pure and enantiomerically/stereomerically enriched compounds provided herein.

As used herein, and unless otherwise indicated, the term "stereomerically pure" or "enantiomerically pure" means that a compound comprises one stereoisomer and is substantially free of its counter stereoisomer or enantiomer. For example, a compound is stereomerically or enantiomerically pure, when the compound contains greater than or equal to 80%, 90%, 95%, 98% or 99% of one stereoisomer, and 20%, 10%, 5%, 2%, 1% or less of the counter stereoisomer. "Substantially free of its (−) enantiomer" is encompassed by the term stereomerically pure or enantiomerically pure.

As used herein, term "adverse effect" includes, but is not limited to gastrointestinal, renal and hepatic toxicities, leukopenia, increases in bleeding times due to, e.g., thrombocytopenia, and prolongation of gestation, nausea, vomiting, somnolence, asthenia, dizziness, teratogenicity, extra-pyramidal symptoms, akathisia, cardiotoxicity including cardiovascular disturbances, inflammation, male sexual dysfunction, and elevated serum liver enzyme levels. The term "gastrointestinal toxicities" includes but is not limited to gastric and intestinal ulcerations and erosions. The term "renal toxicities" includes but is not limited to such conditions as papillary necrosis and chronic interstitial nephritis.

As used herein, the term "patient" refers to a mammal, particularly a human. In some embodiments, the patient is a female. In further embodiments, the patient is a male. In further embodiments, the patient is a child.

As used herein, and unless otherwise specified, the terms "treat," "treating" and "treatment" contemplate an action that occurs while a patient is suffering from the specified disease or disorder, which reduces the severity or symptoms of the disease or disorder, or retards or slows the progression or symptoms of the disease or disorder.

As used herein, unless otherwise specified, the terms "prevent," "preventing" and "prevention" contemplate an action that occurs before a patient begins to suffer from the specified disease or disorder, which inhibits or reduces the severity or symptoms of the disease or disorder.

As used herein, and unless otherwise indicated, the terms "manage," "managing" and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

5.3. Methods of Treatment

Provided herein are methods of treating, managing and/or preventing psoriasis and/or arthritis—including but not limited to rheumatoid arthritis and/or psoriatic arthritis—which comprises administering to a patient in need of such treatment, management or prevention a therapeutically or prophylactically effective amount of Compound A or Compound B, or a pharmaceutically acceptable prodrug, metabolite, polymorph, salt, solvate or clathrate thereof. In some embodiments, the salt or solvate of Compound A or Compound B, is used. In other embodiments, the free base of Compound A or Compound B is used.

Methods provided herein comprise administering either one of Compound A or Compound B, substantially free of its (−) enantiomer, or a pharmaceutically acceptable prodrug, metabolite, polymorph, salt, solvate or clathrate of thereof, after the onset of symptoms of psoriatic and/or rheumatoid arthritis.

Methods provided herein also include inhibiting or averting symptoms of psoriatic and/or rheumatoid arthritis as well as addressing the disease itself, prior to the onset of symptoms by administering Compound A or Compound B, or a pharmaceutically acceptable prodrug, metabolite, polymorph, salt, solvate or clathrate thereof. In some embodiments, patients treated by the methods provided herein have a history of psoriasis or arthritis. In certain embodiments, the methods comprise administering either one of Compound A or Compound B, or a pharmaceutically acceptable prodrug, metabolite, polymorph, salt, solvate or clathrate thereof, to a patient (e.g., a human) suffering or likely to suffer, from psoriasis and/or arthritis (including but not limited to psoriatic and/or rheumatoid arthritis).

PDE4 inhibitors (S)-N-(2-(1-(3-ethoxy-4-methoxyphenyl)-2-(methylsulfonyl)ethyl)-1,3-dioxoisoindolin-4-yl)acetamide and (S)-N-(2-(1-(3-ethoxy-4-methoxyphenyl)-2-(methylsulfonyl)ethyl)-3-oxoisoindolin-4-yl) cyclopropanecarboxamide may be used in the treatment, management or prevention of psoriasis and/or arthritis, including but not limited to rheumatoid arthritis and psoriatic arthritis. The magnitude of a prophylactic or therapeutic dose of a particular active ingredient in the acute or chronic management of arthritis will vary, however, with the nature and severity of the disease or condition, and the route by which the active ingredient is administered. The dose, and perhaps the dose frequency, will also vary according to the age, body weight, and response of the individual patient. Suitable dosing regimens can be readily selected by those skilled in the art with due consideration of such factors.

In general, the recommended daily dose range for the conditions described herein lie within the range of from about 0.1 mg to about 1,000 mg per day, given as a single once-a-day dose or as divided doses throughout a day. More specifically, the daily dose may be administered once, twice, three times, or four times daily in equally divided doses. Specifically, a daily dose range may be from about 1 mg to about 500 mg per day, more specifically, between about 10 mg and about 200 mg per day. Specifically, the daily dose may be administered in 1 mg, 5 mg, 6.25 mg, 10 mg, 15 mg, 20 mg, 25 mg, 30 mg, 50 mg, 100 mg, 200 mg, 300 mg, 400 mg or 500 mg dosage forms (Q.D. or B.I.D.). In managing the patient, the therapy may be initiated at a lower dose, perhaps about 1 mg to about 25 mg, and increased if necessary up to about 200 mg to about 1,000 mg per day as either a single dose or divided doses, depending on the patient's global response. In further embodiments, the daily dose of either Compound A or Compound B is from about 0.01 mg to about 100 mg per kg of a body weight of a patient. In some embodiments, the daily dose of the chosen compound is about 1 mg/kg, 5 mg/kg, 6.25 mg/kg, 10 mg/kg or 25 mg/kg. In certain embodiments, the therapeutically effective amount of the first active agent as provided herein is about 1, 5, or 25 mg per kg of a body weight of the patient per day and the therapeutically effective amount of the additional active agent as provided herein is about 1, 5, or 6.25 mg per kg of a body weight of the patient per day.

5.3.1. Combination Therapy

As provided herein, (S)-N-(2-(1-(3-ethoxy-4-methoxyphenyl)-2-(methylsulfonyl)ethyl)-1,3-dioxoisoindolin-4-yl)acetamide or (S)-N-(2-(1-(3-ethoxy-4-methoxyphenyl)-2-(methylsulfonyl)ethyl)-3-oxoisoindolin-4-yl) cyclopropanecarboxamide may be administered in combination with another drug (a "second active agent" or an "additional active agent") for treating, managing and/or preventing psoriasis and/or arthritis, including but not limited to rheumatoid arthritis and/or psoriatic arthritis.

Either one of Compound A or Compound B can be combined with one or more second active agents in the methods provided herein. In some embodiments, provided herein are synergistic combinations for the treatment, prevention and/or management of psoriasis and/or arthritis, including but not limited to rheumatoid arthritis and psoriatic arthritis. In some embodiments, either one of Compound A or Compound B may also be used to alleviate adverse effects associated with certain second active agents. Alternatively, in some embodiments, certain second active agents may be used to alleviate adverse effects associated with either one of Compound A or Compound B.

Second active agents which may be used in the methods provided herein in combination with Compound A or Compound B include, but are not limited to, disease-modifying anti-rheumatic drugs (DMARDs such as cyclosporine A and methotrexate), anti-inflammatory agents such as nonsteroidal anti-inflammatory drugs (NSAIDs), immunosuppressants, mycophenolate mofetil, biologic agents, TNF-α inhibitors (such as etanercept), Cox-2 inhibitors, and analgesics.

The second active agents can be administered before, after, or simultaneously with either one of Compound A or Compound B.

In some embodiments, the second active agents may include, but are not limited to, anti-inflammatories such as NSAIDs including, but not limited to, diclofenac (e.g., ARTHROTEC®), diflunisal (e.g., DOLOBID®), etodolac (e.g., LODINE®) fenoprofen (e.g., NALFON®), ibuprofen (e.g., ADVIL, CHILDREN'S ADVIL/MOTRIN, MEDIPREN, MOTRIN, NUPRIN or PEDIACARE FEVER®), indomethacin (e.g., ARTHREXIN®), ketoprofen (e.g., ORUVAIL®), ketorolac (e.g., TORADOL®), fosfomycin tromethamine (e.g., MONURAL®), meclofenamate (e.g., Meclomen®), nabumetone (e.g., RELAFEN®), naproxen (e.g., ANAPROX®, ANAPROX® DS, EC-NAPROSYN®, NAPRELAN® or NAPROSYN®), oxaprozin (e.g., DAYPRO®), piroxicam (e.g., FELDENE®), sulindac (e.g., CLINORIL®), and tolmetin (e.g., TOLECTIN® DS or TOLECTIN®).

In other embodiments, the second active agents may include, but are not limited to, disease-modifying antirheumatic drugs (DMARDs) or immunosuppressants such as, but not limited to, methotrexate (Rheumatrex®), sulfasalazine (Azulfidine®), and cyclosporine (Sandimmune® or Neroal®; cyclosporine A).

In other embodiments, the second active agents may include, but are not limited to, mycophenolate mofetil (CellCept®), an immunosuppressive agent widely used in organ transplantation and gaining favor in treating autoimmune and inflammatory skin disorders.

In further embodiments, the second active agents may include, but are not limited to, biologic agents such as etanercept (Enbrel®), infliximab (Remicade®) and adalimumab (Humira®).

In further embodiments of interest, the second active agents may include, but are not limited to, Cox-2 inhibitors such as celecoxib (Celebrex®), valdecoxib (Bextra®) and meloxicam (Mobic®).

In some embodiments, either one of Compound A or Compound B is administered with one of a second active agent selected from the group consisting etanercept, cyclosporine A, and methotrexate.

In some embodiments, the administration of a combination of Compound A and etanercept results in a synergistic therapeutic effect for the treatment, management, and/or prevention of psoriasis and/or arthritis, including but not limited to rheumatoid arthritis and/or psoriatic arthritis.

In some embodiments, the administration of a combination of Compound A and cyclosporine A results in a synergistic therapeutic effect for the treatment, management, and/or prevention of psoriasis and/or arthritis, including but not limited to rheumatoid arthritis and/or psoriatic arthritis.

In some embodiments, the administration of a combination of Compound A and methotrexate results in a synergistic therapeutic effect for the treatment, management, and/or prevention of psoriasis and/or arthritis, including but not limited to rheumatoid arthritis and/or psoriatic arthritis.

In some embodiments, the administration of a combination of Compound B and etanercept results in a synergistic therapeutic effect for the treatment, management, and/or prevention of psoriasis and/or arthritis, including but not limited to rheumatoid arthritis and/or psoriatic arthritis.

In some embodiments, the administration of a combination of Compound B and cyclosporine A results in a synergistic therapeutic effect for the treatment, management, and/or prevention of psoriasis and/or arthritis, including but not limited to rheumatoid arthritis and/or psoriatic arthritis.

In some embodiments, the administration of a combination of Compound B and methotrexate results in a synergistic therapeutic effect for the treatment, management, and/or prevention of psoriasis and/or arthritis, including but not limited to rheumatoid arthritis and/or psoriatic arthritis.

Administration of either one of (S)-N-(2-(1-(3-ethoxy-4-methoxyphenyl)-2-(methylsulfonyl)ethyl)-1,3-dioxoisoindolin-4-yl)acetamide or (S)-N-(2-(1-(3-ethoxy-4-methoxyphenyl)-2-(methylsulfonyl)ethyl)-3-oxoisoindolin-4-yl) cyclopropanecarboxamide and a second active agent— including but not limited to etanercept, cyclosporine A, and/or methotrexate—to a patient can occur simultaneously or sequentially by the same or different routes of administration. The suitability of a particular route of administration employed for a particular second active agent will depend on the second active agent itself (e.g., whether it can be administered orally or topically without decomposition prior to entering the blood stream) and the subject being treated. A particular route of administration of the (+) enantiomer of 2-[1-(3-ethoxy-4-methoxyphenyl)-2-methylsulfonylethyl]-4-acetylaminoisoindoline-1,3-dione is oral administration in dosage forms of a tablet or a capsule. Particular routes of administration for the second active agents or ingredients provided herein are known to those of ordinary skill in the art. See, e.g., *The Merck Manual,* 448 (17th ed., 1999).

The amount of second active agent administered can be determined based on the specific agent used, the subject being treated, the severity and stage of disease and the amount(s) of the either one of Compound A or Compound B and any additional second active agents concurrently administered to the patient. Those of ordinary skill in the art can determine the specific amounts according to conventional procedures known in the art. In the beginning, one can start from the amount of the second active agent that is conventionally used in the therapies and adjust the amount according to the factors described above. See, e.g., *Physician's Desk Reference* (56th Ed., 2004).

It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with individual patient response.

The phrases "therapeutically effective amount," "prophylactically effective amount," and "therapeutically or prophylactically effective amount," as used herein encompasses the above described dosage amounts and dose frequency schedules. Different therapeutically effective amounts may be applicable for different diseases and conditions, as will be readily known by those of ordinary skill in the art. Similarly, amounts sufficient to treat or prevent such disorders, but insufficient to cause, or sufficient to reduce, adverse effects associated with racemic forms of either one of Compound A or Compound B are also encompassed by the dosage amounts described herein and dose frequency schedules.

5.4. Pharmaceutical Compositions and Dosage Forms

Pharmaceutical compositions can be used in the preparation of individual, single unit dosage forms. Pharmaceutical compositions and dosage forms provided herein may comprise a PDE4 inhibitor, including but not limited to Compound A or Compound B, or a pharmaceutically acceptable salt, solvate, hydrate, clathrate, or prodrug thereof and a second active agent, including but not limited to those anti-inflammatory agents described herein. Pharmaceutical compositions and dosage forms may further comprise one or more carriers, excipients, or diluents.

Single unit dosage forms provided herein are suitable for oral, mucosal (e.g., nasal, sublingual, vaginal, cystic, rectal, preputial, ocular, buccal or aural), parenteral (e.g., subcutaneous, intravenous, bolus injection, intramuscular or intraarterial), topical (e.g., eye drops or other ophthalmic preparations), transdermal or transcutaneous administration to a patient. Non-limiting examples of dosage forms include tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions or a water-in-oil liquid emulsions), solutions and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape and type of dosage forms provided herein will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms provided herein will vary from one another will be readily apparent to those skilled in the art. See, e.g., *Remington's Pharmaceutical Sciences,* 20th ed., Mack Publishing, Easton Pa. (2000).

Typical pharmaceutical compositions and dosage forms comprise one or more excipients. Suitable excipients are well known to those skilled in the art of pharmacy and non-limiting examples of suitable excipients are provided herein. Whether a particular excipient is suitable for incorporation into a pharmaceutical composition or dosage fowl depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients can be accelerated by some excipients such as lactose or when exposed to water. Active ingredients that comprise primary or secondary amines are particularly susceptible to such accelerated decomposition. Consequently, provided herein are pharmaceutical compositions and dosage forms that contain little, if any, lactose other mono- or di-saccharides. As used herein, the term "lactose-free" means that the amount of lactose present, if any, is insufficient to substantially increase the degradation rate of an active ingredient.

Lactose-free compositions provided herein may comprise excipients that are well known in the art and are listed, for example, in the *US. Pharmacopeia* (USP) 25-NF20 (2002). In general, lactose-free compositions comprise active ingredients, a binder/filler and a lubricant in pharmaceutically compatible and pharmaceutically acceptable amounts. Particular lactose-free dosage forms comprise active ingredients, microcrystalline cellulose, pre-gelatinized starch and magnesium stearate.

Also provided herein are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment and use of formulations.

Anhydrous pharmaceutical compositions and dosage forms provided herein may be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Non-limiting examples of suitable packaging include hermetically sealed foils, plastics, unit dose containers (e.g., vials), blister packs and strip packs.

Also provided herein are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers or salt buffers. Like the amounts and types of excipients, the amounts and specific types of active ingredients in a dosage form may differ depending on factors such as, but not limited to, the route by which it is to be administered to patients. However, typical dosage forms provided herein comprise either one of (S)-N-(2-(1-(3-ethoxy-4-methoxyphenyl)-2-(methylsulfonyl)ethyl)-1,3-dioxoisoindolin-4-yl)acetamide or (S)-N-(2-(1-(3-ethoxy-4-methoxyphenyl)-2-(methylsulfonyl)ethyl)-3-oxoisoindolin-4-yl)cyclopropanecarboxamide or a pharmaceutically acceptable salt or solvate thereof in an amount of from about 1 to about 1,000 mg. Typical dosage forms comprise either one of Compound A or Compound B or a pharmaceutically acceptable salt or solvate thereof in an amount of about 1, 2, 5, 7.5, 10, 12.5, 15, 17.5, 20, 25, 30, 50, 100, 150 or 200 mg. In a particular embodiment, a dosage form comprises either one of Compound A or Compound B in an amount of about 1, 5, 10, 15, 20, 25, 30, 50, 100 or 200 mg.

Of course, the specific amount of anti-arthritic drug will depend on the specific agent used, the type of arthritis being treated or managed, and the amount(s) of a PDE4 inhibitor provided herein and any additional active agents concurrently administered to the patient.

5.4.1. Oral Dosage Forms

Pharmaceutical compositions provided herein that are suitable for oral administration can be presented as discrete dosage forms, such as, but not limited to, tablets (e.g., chewable tablets), caplets, capsules and liquids (e.g., flavored syrups). Such dosage forms contain predetermined amounts of active ingredients and can be prepared by methods of pharmacy well known to those skilled in the art. See generally, *Remington's Pharmaceutical Sciences,* 20th ed., Mack Publishing, Easton Pa. (2000).

Typical oral dosage forms provided herein are prepared by combining the active ingredients in an intimate admixture with at least one excipient according to conventional pharmaceutical compounding techniques. Excipients can take a wide variety of forms depending on the form of preparation desired for administration. Non-limiting examples of excipients suitable for use in oral liquid or aerosol dosage forms include water, glycols, oils, alcohols, flavoring agents, preservatives and coloring agents. Non-limiting examples of excipients suitable for use in solid oral dosage forms (e.g., powders, tablets, capsules and caplets) include starches, sugars, microcrystalline cellulose, diluents, granulating agents, lubricants, binders and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers or both and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Non-limiting examples of excipients that can be used in oral dosage forms provided herein include binders, fillers, disintegrants and lubricants. Non-limiting examples of binders suitable for use in pharmaceutical compositions and dosage forms include corn starch, potato starch or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose and mixtures thereof.

Non-limiting examples of suitable forms of microcrystalline cellulose include the materials sold as AVICEL-PH-101, AVICEL-PH-103 AVICEL RC-581, AVICEL-PH-105 (available from FMC Corporation, American Viscose Division, Avicel Sales, Marcus Hook, Pa.) and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Non-limiting examples of fillers suitable for use in the pharmaceutical compositions and dosage forms disclosed herein include talc, calcium carbonate (e.g., granules or powder), microcrystalline cellulose, powdered cellulose, dextrates, kaolin, mannitol, silicic acid, sorbitol, starch, pre-gelatinized starch and mixtures thereof. The binder or filler in pharmaceutical compositions is typically present in from about 50 to about 99 weight percent of the pharmaceutical composition or dosage form.

Disintegrants may be used in the compositions provided herein to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms. The amount of disintegrant used varies based upon the type of formulation and is readily discernible to those of ordinary skill in the art. Typical pharmaceutical compositions comprise from about 0.5 to about 15 weight percent of disintegrant, preferably from about 1 to about 5 weight percent of disintegrant.

Non-limiting examples of disintegrants that can be used in pharmaceutical compositions and dosage forms provided herein include agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums and mixtures thereof.

Non-limiting examples of lubricants that can be used in pharmaceutical compositions and dosage forms provided herein include calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil and soybean oil), zinc stearate, ethyl oleate, ethyl laureate, agar and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.) and mixtures thereof. If used at all, lubricants are typically used in an amount of less than about 1 weight percent of the pharmaceutical compositions or dosage forms into which they are incorporated.

In one embodiment, a solid oral dosage form provided herein comprises either one of Compound A or Compound B, anhydrous lactose, microcrystalline cellulose, polyvinylpyrrolidone, stearic acid, colloidal anhydrous silica and gelatin.

5.4.2. Delayed Release Dosage Forms

Active ingredients can be administered by controlled release means or by delivery devices that are well known to those of ordinary skill in the art. Non-limiting examples of controlled release means or delivery devices include those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556 and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres or a combination thereof to provide the desired release profile in varying proportions. Suitable controlled-release formulations known to those of ordinary skill in the art, including those described herein, can be readily selected for use with the active ingredients provided herein. Thus, in some embodiments, provided herein are single unit dosage forms suitable for oral administration such as, but not limited to, tablets, capsules, gelcaps and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency and increased patient compliance. In addition, controlled-release formulations can be used to affect the time of onset of action or other characteristics, such as blood levels of the drug and can thus affect the occurrence of side (e.g., adverse) effects.

Most controlled-release formulations are designed to initially release an amount of drug (active ingredient) that promptly produces the desired therapeutic effect and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water or other physiological conditions or compounds.

5.4.3. Parenteral Dosage Forms

Parenteral dosage forms can be administered to patients by various routes including, but not limited to, subcutaneous, intravenous (including bolus injection), intramuscular and intraarterial. Because their administration typically bypasses patients' natural defenses against contaminants, parenteral dosage forms are preferably sterile or capable of being sterilized prior to administration to a patient. Non-limiting examples of parenteral dosage forms include solutions ready for injection, dry products ready to be dissolved or suspended in a pharmaceutically acceptable vehicle for injection, suspensions ready for injection and emulsions.

Suitable vehicles that can be used to provide parenteral dosage forms are well known to those skilled in the art. Non-limiting examples of suitable vehicles include Water for Injection USP; aqueous vehicles such as, but not limited to, Sodium Chloride Injection, Ringer's Injection, Dextrose Injection, Dextrose and Sodium Chloride Injection and Lactated Ringer's Injection; water-miscible vehicles such as, but not limited to, ethyl alcohol, polyethylene glycol and polypropylene glycol; and non-aqueous vehicles such as, but not limited to, corn oil, cottonseed oil, peanut oil, sesame oil, ethyl oleate, isopropyl myristate and benzyl benzoate.

Compounds that increase the solubility of one or more of the active ingredients disclosed herein can also be incorporated into the parenteral dosage forms provided herein. For example, cyclodextrin and its derivatives can be used to increase the solubility of either one of (S)-N-(2-(1-(3-ethoxy-4-methoxyphenyl)-2-(methylsulfonyl)ethyl)-1,3-dioxoisoindolin-4-yl)acetamide or (S)-N-(2-(1-(3-ethoxy-4-methoxyphenyl)-2-(methylsulfonyl)ethyl)-3-oxoisoindolin-4-yl)cyclopropanecarboxamide and their derivatives.

5.4.4. Topical and Mucosal Dosage Forms

Drugs can be applied locally to the skin and its adnexa or to a variety of mucous membranes. The routes that can be used include nasal, sublingual, vaginal, cystic, rectal, preputial, ocular, buccal or aural. Many dosage forms have been developed to deliver active principles to the site of application to produce local effects. Non-limiting examples of topical and mucosal dosage forms provided herein include sprays, inhalers, aerosols, ointments, creams, gels, pastes, dusting powders, lotions, liniments, poultices, solutions, emulsions, suspensions, eye drops or other ophthalmic preparations or other forms known to one of skill in the art. See, e.g., *Remington's Pharmaceutical Sciences*, 20$^{th}$ ed., Mack Publishing, Easton Pa. (2000); and *Introduction to Pharmaceutical Dosage Forms*, 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms are well known to those skilled in the pharmaceutical arts and depend on the particular tissue to which a given pharmaceutical composition or dosage form will be applied. Non-limiting examples of typical excipients include water, acetone, ethanol, ethylene glycol, propylene glycol, butane-1,3-diol, isopropyl myristate, isopropyl palmitate, mineral oil and mixtures thereof to form solutions, emulsions or gels, which are non-toxic and pharmaceutically acceptable.

Moisturizers such as occlusives, humectants, emollients and protein rejuvenators can also be added to pharmaceutical compositions and dosage forms if desired. Examples of such additional ingredients are well known in the art. See, e.g., *Remington's Pharmaceutical Sciences*, 20th ed., Mack Publishing, Easton Pa. (2000).

Occlusives are substances that physically block water loss in the stratum corneum. Non-limiting examples of occlusives include petrolatum, lanolin, mineral oil, silicones such as dimethicone, zinc oxide and combinations thereof. Preferably, the occlusives are petrolatum and lanolin, more preferably petrolatum in a minimum concentration of 5%.

Humectants are substances that attract water when applied to the skin and theoretically improve hydration of the stratum corneum. However, the water that is drawn to the skin is water from other cells, not atmospheric water. With this type of moisturizer, evaporation from the skin can continue and actually can make the dryness worse. Non-limiting examples of humectants include glycerin, sorbitol, urea, alpha hydroxy acids, sugars and combinations thereof. Preferably, the humectants are alpha hydroxy acids, such as glycolic acid, lactic acid, malic acid, citric acid and tartaric acid.

Emollients are substances that smooth skin by filling spaces between skin flakes with droplets of oil, and are not usually occlusive unless applied heavily. When combined with an emulsifier, they may help hold oil and water in the stratum corneum. Vitamin E is a common additive, which appears to have no effect, except as an emollient. Likewise, other vitamins, for example, A and D, are also added, but their effect is questionable. Non-limiting examples of emollients include mineral oil, lanolin, fatty acids, cholesterol, squalene, structural lipids and combinations thereof.

Protein rejuvenators are substances that rejuvenate the skin by replenishing essential proteins. Non-limiting examples of protein rejuvenators include collagen, keratin, elastin and combinations thereof.

The pH of a pharmaceutical composition or dosage form may also be adjusted to improve delivery of one or more active ingredients. Similarly, the polarity of a solvent carrier, its ionic strength or tonicity can be adjusted to improve delivery. For example, absorption through the skin can also be enhanced by occlusive dressings, inunction or the use of dimethyl sulfoxide as a carrier. Compounds such as metal stearates (e.g., calcium stearate, zinc stearate, magnesium stearate, sodium stearate, lithium stearate, potassium stearate, etc.) can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant and as a delivery-enhancing or penetration-enhancing agent. Different salts, hydrates or solvates of the active ingredients can be used to further adjust the properties of the resulting composition.

In certain embodiments, one or both of the active agents as provided herein are administered parenterally, transdermally, mucosally, nasally, buccally, sublingualy, topically, or orally. In certain embodiments, the first active agent is administered orally in a tablet or capsule form. In certain embodiments, one or more of the active agents are administered topically (e.g. in the dosage form of a lotion or a liquid).

5.4.5 Kits

Active ingredients are often not administered to a patient at the same time or by the same route of administration. In some embodiments, provided herein are kits which, when used by the medical practitioner, can simplify the administration of appropriate amounts of active ingredients to a patient.

A typical kit comprises a unit dosage form of Compound A or Compound B, or a pharmaceutically acceptable salt, solvate, hydrate, clathrate, polymorph or prodrug of Compound A or Compound B, and a unit dosage form of a second active ingredient. Examples of second active ingredients include, but are not limited to, those listed herein, for example etanercept, methotrexate, and cyclosporine A.

Kits can further comprise devices that are used to administer the active ingredient(s). Examples of such devices include, but are not limited to, syringes, drip bags, patches, and inhalers.

Kits can further comprise pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

6. EXAMPLES

Some embodiments provided herein are illustrated by the following non-limiting examples. The examples should not be construed as a limitation in the scope thereof.

6.1. Example 1

Synthesis of 2-[1-(3-ethoxy-4-methoxyphenyl)-2-methylsulfonylethyl]-4-acetylaminoisoindoline-1,3-dione A stirred solution of 1-(3-ethoxy-4-methoxyphenyl)-methylsulfonylethylamine (1.0 g, 3.7 mmol) and 3-acetamidophthalic anhydride (751 mg, 3.66 mmol) in acetic acid (20 mL) was heated at reflux for 15 h. The solvent was removed in vacuo to yield an oil. Chromatography of the resulting oil yielded the product as a yellow solid (1.0 g, 59% yield): mp, 144° C.; $^1$H NMR (CDCl$_3$) δ1.47 (t, J=7.0 Hz, 3H, CH$_3$), 2.26 (s, 3H, CH$_3$), 2.88 (s, 3H, CH$_3$), 3.75 (dd, J=4.4, 14.3 Hz, 1H, CHH), 3.85 (s, 3H, CH3), 4.11 (q, J=7 Hz, 2H, CH2), 5.87 (dd, J=4.3, 10.5 Hz, 11-1, NCH), 6.82-6.86 (m, 1H, Ar), 7.09-7.11 (m, 2H, Ar), 7.47 (d, J=7 Hz, 1H, Ar), 7.64 (t, J=8 Hz, 1H, Ar), 8.74 (d, J=8 Hz, 1H, Ar), 9.49 (br s, 1H, NH); $^{13}$C NMR (CDCl$_3$) δ14.61, 24.85, 41.54, 48.44, 54.34, 55.85, 64.43, 111.37, 112.34, 115.04, 118.11, 120.21, 124.85, 129.17, 130.96, 136.01, 137.52, 148.54, 149.65, 167.38, 169.09, 169.40; Anal Calc'd. for C$_{22}$H$_{24}$NO$_7$S: C, 57.38; H, 5.25; N, 6.08. Found: C, 57.31; H, 5.34; N, 5.83.

6.2. Example 2

Preparation of (+)-2-[1-(3-Ethoxy-4-methoxyphenyl)-2-methylsulfonylethyl]-4-acetylaminoisoindoline-1,3-dione ("Compound A")

6.2.1. Preparation of 3-Aminophthalic Acid

A mixture of 10% Pd/C (2.5 g), 3-nitrophthalic acid (75.0 g, 355 mmol) and ethanol (1.5 L) was charged to a 2.5 L Parr hydrogenator, under a nitrogen atmosphere. Hydrogen was charged to the reaction vessel for up to 55 psi. The mixture was shaken for 13 hours, maintaining hydrogen pressure between 50 and 55 psi. Hydrogen was released and the mixture was purged with nitrogen 3 times. The suspension was filtered through a celite bed and rinsed with methanol. The filtrate was concentrated in vacuo. The resulting solid was reslurried in ether and isolated by vacuum filtration. The solid was dried in vacuo to a constant weight, affording 54 g (84% yield) of 3-aminophthalic acid as a yellow product. $^1$H-NMR (DMSO-d6) δ: 3.17 (s, 2H), 6.67 (d, 1H), 6.82 (d, 1H), 7.17 (t, 1H), 8-10 (brs, 2H). $^{13}$C-NMR (DMSO-d6) δ: 112.00, 115.32, 118.20, 131.28, 135.86, 148.82, 169.15, 170.09.

6.2.2. Preparation of 3-Acetamidophthalic Anhydride

A 1 L 3-necked round bottom flask was equipped with a mechanical stirrer, thermometer, and condenser and charged with 3-aminophthalic acid (108 g, 596 mmol) and acetic anhydride (550 mL). The reaction mixture was heated to reflux for 3 hours and cooled to ambient temperature and further to 0-5° C. for another 1 hour. The crystalline solid was collected by vacuum filtration and washed with ether. The solid product was dried in vacuo at ambient temperature to a constant weight, giving 75 g (61% yield) of 3-acetamidopthalic anhydride as a white product. $^1$H-NMR (CDCl$_3$) δ: 2.21 (s, 3H), 7.76 (d, 1H), 7.94 (t, 1H), 8.42 (d, 1H), 9.84 (s, 1H).

6.2.3. Resolution of 2-(3-ethoxy-4-methoxyphenyl)-1-(methylsulphonyl)-eth-2-ylamine A 3 L 3-necked round bottom flask was equipped with a mechanical stirrer, thermometer, and condenser and charged with 2-(3-ethoxy-4-methoxyphenyl)-1-(methylsulphonyl)-eth-2-ylamine (137.0 g, 500 mmol), N-acetyl-L-leucine (52 g, 300 mmol), and methanol (1.0 L). The stirred slurry was heated to reflux for 1 hour. The stirred mixture was allowed to cool to ambient temperature and stirring was continued for another 3 hours at ambient temperature. The slurry was filtered and washed with methanol (250 L). The solid was air-dried and then dried in vacuo at ambient temperature to a constant weight, giving 109.5 g (98% yield) of the crude product (85.8% ee). The crude solid (55.0 g) and methanol (440 mL) were brought to reflux for 1 hour, cooled to room temperature and stirred for an additional 3 hours at ambient temperature. The slurry was filtered and the filter cake was washed with methanol (200 mL). The solid was air-dried and then dried in vacuo at 30° C. to a constant weight, yielding 49.6 g (90% recovery) of (S)-2-(3-ethoxy-4-methoxyphenyl)-1-(methylsulphonyl)-eth-2-ylamine-N-acetyl-L-leucine salt (98.4% ee). Chiral HPLC (1/99 EtOH/20 mM KH$_2$PO$_4$@pH 7.0, Ultron Chiral ES-OVS from Agilent Technologies, 150 mm×4.6 mm, 0.5 mL/min., @240 nm): 18.4 min (S-isomer, 99.2%), 25.5 min (R-isomer, 0.8%).

6.2.4. Preparation of (+)-2-[1-(3-Ethoxy-4-methoxyphenyl)-2-methylsulfonylethyl]-4-acetylaminoisoindoline-1,3-dione A 500 mL 3-necked round bottom flask was equipped with a mechanical stirrer, thermometer, and condenser. The reaction vessel was charged with (S)-2-(3-ethoxy-4-methoxyphenyl)-1-(methylsulphonyl)-eth-2-yl amine N-acetyl-L-leucine salt (25 g, 56 mmol, 98% ee), 3-acetamidophthalic anhydride (12.1 g 58.8 mmol), and glacial acetic acid (250 mL). The mixture was refluxed over night and then cooled to <50° C. The solvent was removed in vacuo, and the residue was dissolved in ethyl acetate. The resulting solution was washed with water (250 mL×2), saturated aqueous NaHCO$_3$ (250 mL×2), brine (250 mL×2), and dried over sodium sulphate. The solvent was evaporated in vacuo, and the residue recrystallized from a binary solvent containing ethanol (150 mL) and acetone (75 mL). The solid was isolated by vacuum filtration and washed with ethanol (100 mL×2). The product was dried in vacuo at 60° C. to a constant weight, affording 19.4 g (75% yield) of (S)-{2-[1-(3-ethoxy-4-methoxyphenyl)-2-methylsulfonylethyl]-4-inoisoindoline-1,3-dione with 98% ee. Chiral HPLC (15/85 EtOH/20 mM KH$_2$PO$_4$@pH 0.5, Ultron Chiral ES-OVS from Agilent Technology, 150 mm×4.6 mm, 0.4 mL/min., @240 nm): 25.4 mM (S-isomer, 98.7%), 29.5 min (R-isomer, 1.2%). $^1$H-NMR (CDCl$_3$) δ: 1.47 (t, 3H), 2.26 (s, 3H), 2.87 (s, 3H), 3.68-3.75 (dd, 1H), 3.85 (s, 3H), 4.07-4.15 (q, 2H), 4.51-4.61 (dd, 1H), 5.84-5.90 (dd, 1H), 6.82-8.77 (m, 6H), 9.46 (s, 1H). $^{13}$C-NMR (DMSO-d6) δ: 14.66, 24.92, 41.61, 48.53, 54.46, 55.91, 64.51, 111.44, 112.40, 115.10, 118.20, 120.28, 124.94, 129.22, 131.02, 136.09, 137.60, 148.62, 149.74, 167.46, 169.14, 169.48.

Specific crystalline faurs of Compound A may be prepared according to U.S. Pat. No. 7,893,101, the disclosure of which is hereby incorporated by reference in its entirety.

6.3. Example 3

Evaluation of Anti-Arthritic Activity in mAB/LPS-induced Experimental Murine Arthritogenic Model The anti-arthritic activity of (+)-2-[1-(3-ethoxy-4-methoxyphenyl)-2-methylsulfonylethyl]-4-acetylaminoisoindoline-1,3-dione ("(+) isomer"; Compound A) was assessed in the mAB/LPS-induced experimental murine arthritogenic model. The mice were administered with 1, 5 and 25 mg/kg once daily oral (PO) gavage throughout five successive treatment days. The treatment groups comprised n=8 BALB/c male mice per group. Two equally sized groups were treated with either dexamethasone (1 mg/kg) or a suspension of 0.5% CMC/0.25% Tween 80, served as Positive or Vehicle Controls, respectively.

Experimental arthritis was initially induced on Day 0 of the study by intravenous (IV) injection of a 4 monoclonal antibodies (mAB) cocktail at a dose of 100 mg/kg, followed about 72 hours later by the intraperitoneal (IP) injection of LPS 2.5 mg/kg.

Paw thickness was determined with an electronic digital caliper on six occasions (Day 0, 4, 5, 6, 7 & 9) and presented as mean group values of the average for both left and right hind paws. The result is shown in FIG. 1. Data clearly indicated highly statistically significant (p<0.01 vs. Vehicle Control) and constant suppression of paw swelling in the highest dose (25 mg/kg) of Compound A treatment group, equaling that of the Positive Control Dexamethasone group. A lesser extent (p<0.05 vs. Vehicle Control) was revealed in animals administered 5 mg/kg of (+) isomer (intermediate dose), but was limited to Day 9 measurement occasion.

In this study, Compound A, administered orally at a once daily dose of 25 mg/kg during five successive days, demonstrated comparable potential anti-arthritic activity, evident from a statistically significant reduction of paw swelling as achieved by dexamethasone (1 mg/kg) applied by an identical dosing regimen.

6.3.1. Histopathological Evaluation

To determine the potential anti-arthritic activity of (+)-2-[1-(3-ethoxy-4-methoxyphenyl)-2-methylsulfonylethyl]-4- acetylaminoisoindoline-1,3-dione ("(+) isomer"; Compound A), total 16 animals were tested with Vehicle Control or 25 mg/kg of (+) isomer for histopathological evaluation. Left hind limbs were fixed in 10% neutral buffered formalin for 1 week, then transferred into buffered inorganic acid (decalcification process for about 48 hours) and back into 10% formalin prior to storage. Each limb from the middle of the tibia and distally, to include the ankle joint, i.e., the joint between the leg and foot (tibial-tarsus joint), was trimmed mid-longitudinally, and both halves were embedded in paraffin and slides of 6 micron thickness were cut and stained by hematoxylin and eosin. Histopathological changes in the joints were described and scored, using semiquantitative grading of five grades (0-4), taking into consideration the severity of the changes (0=unremarkable, 1=minimal, 2=mild, 3=moderate, 4=marked). Individual findings are presented in Table 1. The results indicate successful induction of the arthritis model, achieving grade 3 (moderate) of severity. All typical ranges of changes characteristically seen in this arthritis were noted. All samples from animals treated with the test Compound A had practically no existing arthritis, indicating very potent capacity to inhibit arthritis development.

Experimental arthritis was initially induced on Day 0 of the study by a single intravenous injection of a 4 monoclonal antibodies (mAb) cocktail at a dose level of 100 mg/kg, followed about 72 hours later by a single intraperitoneal (IP) injection of LPS 2.5 mg/kg.

No obvious treatment-related adverse reactions were noted among all Compound A-treated animals throughout the entire 14-day observation period, excluding the typical reactions to LPS injection, characterized by piloerection, decrease in the spontaneous motor activity and slight diarrhea.

Hind paw thickness was determined with an electronic digital caliper on eight occasions (on Days 0, 4, 5, 6, 7, 9, 11 & 14) and presented as mean group values of the average for both left and right hind paws. The result is shown in FIG. 2. Data clearly indicated highly significant decrease (P<0.01 vs. Vehicle Control) in animals subjected to repeated administrations of 5 or 25 mg/kg of Compound A, equaling that of the Positive Controls-treated animals (5 or 6.25 mg/kg Enbrel) or the combined Enbrel-Compound A treatment on study days 5, 7, 9, 11 and 14.

The mean group arthritogenic scoring value of both hind paws (left & right average value/animal) in animals subjected

TABLE 1

Histopathological features observed in the tibiotarsal joint of arthritic mice treated with vehicle (control) or Compound A

| Animal No./ Histopathology | Control | | | | | | | | Compound A | | | | | | | |
|---|---|---|---|---|---|---|---|---|---|---|---|---|---|---|---|---|
| | 1 | 2 | 3 | 4 | 5 | 6 | 7 | 8 | 25 | 26 | 27 | 28 | 29 | 30 | 31 | 32 |
| Synovial hyperplasia | 1 | 2 | 1 | 2 | 2 | 1 | 1 | 1 | 0 | 0 | 0 | 0 | 0 | 0 | 0 | 0 |
| Synovial villus formation | 1 | 2 | 1 | 2 | 2 | 1 | 1 | 1 | 0 | 0 | 0 | 0 | 0 | 0 | 0 | 0 |
| Fibrin deposition | 2 | 3 | 3 | 3 | 3 | 2 | 3 | 3 | 0 | 0 | 0 | 0 | 0 | 1 | 0 | 1 |
| Inflammatory infiltration in the synovial membrane | 3 | 3 | 3 | 3 | 3 | 3 | 3 | 3 | 0 | 0 | 0 | 0 | 0 | 0 | 0 | 0 |
| Pannus formation (reflected by proliferation of granulation tissue) | 3 | 3 | 3 | 3 | 3 | 3 | 3 | 3 | 0 | 0 | 0 | 0 | 0 | 0 | 0 | 0 |
| Cartilage disruption | 2 | 2 | 2 | 2 | 2 | 2 | 2 | 3 | 0 | 0 | 0 | 0 | 0 | 0 | 0 | 0 |
| Hyaline cartilage destruction (reflected by resorption/erosion in the cartilage) | 2 | 2 | 2 | 2 | 2 | 2 | 3 | 3 | 0 | 0 | 0 | 0 | 0 | 0 | 0 | 0 |
| Subchondral bone destruction (reflected by resorption/erosion by osteoclasts and loss of bone) | 3 | 3 | 2 | 3 | 2 | 2 | 2 | 3 | 0 | 0 | 0 | 0 | 0 | 0 | 0 | 0 |
| Overall assessment: "determined as arthritis" | 3 | 3 | 3 | 3 | 3 | 3 | 3 | 3 | 0 | 0 | 0 | 0 | 0 | 0 | 0 | 0 |

6.3.2. Antibody-Induced Arthritis in Mice

The potential anti-arthritic activity was assessed in the mAb/LPS-induced experimental murine arthritogenic model for (+)-2-[1-(3-ethoxy-4-methoxyphenyl)-2-methylsulfonylethyl]-4-acetylaminoisoindoline-1,3-dione ("(+) isomer"; Compound A), administered at 5 and 25 mg/kg once daily by repeated oral administrations during 11 successive treatment days. Test item-treated groups comprised n=8 BALB/c male mice per group. In addition, four equally sized groups treated with either Enbrel (5 or 6.25 mg/kg, Positive Control), a suspension of 0.5% CMC/0.25% Tween 80 (5 ml/kg, Vehicle Control), or with a combination of Enbrel and Compound A (each 5 mg/kg, Positive Control-Test Item group).

to the combination of Enbrel-Compound A and in those subjected to 6.25 mg/kg of Enbrel was highly to extremely statistically lower (p<0.01 & p<0.001, respectively) than those recorded in the Vehicle Control group on study days 7, 9, 11 and 14. In addition, in animals subjected to 25 mg/kg of Compound A, statistically to extremely significant reductions (p<0.05, p<0.01, p<0.001) vs. the Vehicle Control group were revealed on Days 9, 11 and 14, respectively.

Mean group percentage change in hind paw thickness vs. arthritis induction initiation (employed on Day 0 of the study) was found to be highly significantly lower (P<0.01) in animals subjected to repeated administrations of 5 or 25 mg/kg of (+) isomer, 5 or 6.25 mg/kg of Enbrel or in the combined Enbrel-Compound A-treated group, compared with the Vehicle Control group throughout the entire swelling period on Days 7, 9, 11, & 14.

In this study, Compound A, orally administered at 5 and 25 mg/kg once daily during 11 successive treatment days, revealed comparable potential anti-arthritic activity, evident from a statistically significant reduction in paw swelling as achieved by both Enbrel 5 or 6.25 mg/kg, applied by an identical dosing regimen.

6.4. Example 4

Anti-Inflammatory Activity of Compound A against T Cells In Vitro and in the Mouse Model of Collagen Antibody-Induced Arthritis Alone and in Combination The anti-inflammatory activity of Compound A in T cells was measured alone and in combination with other anti-rheumatic agents including etanercept (ETN), cyclosporine A (CsA), and methotrexate (MTX). Compound A was tested alone and in combination in the mouse model of collagen antibody-induced arthritis (CAIA).

6.4.1. Methods

Human peripheral blood total T cells from healthy donors (n=5) were isolated by negative selection on magnetic beads and stimulated at 1.25×. 10e6 cells/mL with anti-CD3 antibody for 2 days. Cytokine and chemokine protein levels were analyzed by cytometric bead array on a Luminex 100. CAIA model: Male BALB/c mice (n=10 per group) were intravenously injected with a 4 monoclonal antibodies cocktail at a dose of 100 mg/kg, and 3 days later injected intraperitoneally (IP) with LPS at 2.5 mg/kg. Compound A and ETN were administered once daily on days 3-13. Compound A was dosed orally as a suspension of 1, 5, or mg/kg qd. ETN was injected IP at 5 or 6.25 mg/kg. Both hind paws (left and right) of each animal were examined for signs of arthritogenic responses in blinded fashion. Arthritic reactions were scored and recorded according to a 0-4 scale in ascending order of severity. Hind paw thickness was measured in mm using a Mitutoyo Electronic Digital Caliper. Both hind paws were dissected free just above the ankle, fixed in 10% neutral buffered formalin, and analyzed for histopathology.

6.4.2. Results

Compound A inhibited production of all T cell cytokines and chemokines measured (IL-2, IL-4, IL-13, IFN-γ, TNF-α, CXCL10, CCL3, and CCL4) with 50% inhibitory concentrations ($IC_{50}$s) of 15-360 ng/mL CsA also inhibited all analytes, with $IC_{50}$s of 4.7-140 ng/mL. By contrast, ETN potently inhibited TNF-α ($IC_{50}$=1.5 ng/mL), and to a lesser degree IL-13 and IP-10 (16-62 ng/mL), but $IC_{50}$s for all other analytes were >1600 ng/mL. MTX $IC_{50}$s were all >1600 ng/mL. Synergistic inhibition was observed for the combinations of Compound A+ETN and Compound A+CsA. In the CAIA model, hind-paw arthritic reaction scores and thickness were significantly reduced (p<0.01) by Compound A at 5 and 25 mg/kg, and by ETN at both doses tested. At the high dose, Compound A inhibited synovial hyperplasia, synovial villus formation, fibrin deposition, inflammatory infiltration in the synovial membrane, pannus formation, cartilage disruption, and subchondral bone destruction (reflected by resorption/erosion by osteoclasts and loss of bone). The combination of Compound A+etanercept at 5 mg/kg each was additive-to-synergistic in the arthritis model.

Treatment of human T cells with Compound A resulted in inhibition of IL-2, IL-4, IL-13, IFN-γ, TNF-α, CXCL10, CCL3, and CCL4. In combination with ETN or CsA, Compound A synergistically inhibited several of the cytokines and chemokines. In the CAIA model, Compound A reduced paw swelling and arthritic reaction scores, and at 25 mg/kg had practically no existing arthritis by histopathological analysis. Compound A and etanercept combined favorably in this model of arthritis.

6.5 Example 5

Preparation of Cyclopropanecarboxylic Acid {2-[(1S)-1-(3-ethoxy-4-methoxy-phenyl)-2-methane-sulfonyl-ethyl]-3-oxo-2,3-dihydro-1H-isoindol-4-yl}-amide ("Compound B")

6.5.1. Preparation of Methyl 2-methyl-6-nitrobenzoate

A mixture of 2-methyl-6-nitrobenzoic acid (300.0 g, 1.66 moles, from Acros Organics, Morris Plains, N.J.) and trimethyl orthoacetate (298.3 g, 2.48 moles, from Aldrich Chemicals, Milwaukee, Wis.) was charged into a 3-L 3-necked flask at about 20-25° C. under nitrogen. The reaction mixture was gradually heated and the low-boiling point components generated during the reaction were distilled off to an internal temperature of 95-100° C. After 2 hours, the reaction mixture was cooled to 20-25° C. over 1-2 hours. After heptane (1.50 L, from Aldrich Chemicals) was charged into the reaction mixture over 1.0-1.5 hours, the reaction mixture was seeded with methyl 2-methyl-6-nitrobenzoate (0.5 g) when it became turbid. The suspension was cooled to 0-5° C. over 0.5-1 hour and kept at 0-5° C. for another 1.5-2 hours. The solid was collected by filtration under vacuum, washed with heptane (3×300 mL), and dried to a constant weight in a tray at 30-35° C. under a vacuum at 100-120 ton. The yield of methyl 2-methyl-6-nitrobenzoate was 292.0 g (91%), based on 300.0 g of 2-methyl-6-nitrobenzoic acid. The product was found to have a purity of >99% measured by HPLC based on area percentage, and a water content of <0.1% measured by Karl Fisher titration.

6.5.2. Preparation of Methyl 2-bromomethyl-6-nitrobenzoate

A mixture of methyl 2-methyl-6-nitrobenzoate (200.0 g, 1.02 moles, previously prepared), 1,3-dibromo-5,5-dimethylhydantoin (DBH, 162.0 g, 0.57 mole, from Aldrich Chemicals) and methyl acetate (1.20 L, from Aldrich Chemicals) was charged into a 3-L three-necked flask at about 20-25° C. under nitrogen. After the reaction mixture was refluxed for 0.5-1 hour, a solution of 2,2'-azobisisobutyronitrile (AIBN, 8.6 g, 52 mmol, from Aldrich Chemicals) in 100 mL of methyl acetate was charged over 15-30 minutes. The reaction mixture was refluxed for 6.5-8 hours until the amount of unreacted 2-methyl-6-nitrobenzoate was less than 5-10%. The reaction mixture was cooled to 15-18° C. and kept at 15-18° C. for 50-60 minutes. The solid was filtered, washed with cold (i.e., 5-10° C.) methyl acetate (2×100 mL) until there was less than 3% of methyl 2-bromomethyl-6-nitrobenzoate remained in the solid. Next, after heptane (1.00 L) was charged into the filtrate, the upper layer organic phase was washed with 2% of brine (2×500 mL) and deionizer water (1-2×500 mL) until there was less than 0.5% (area percentage at 210 nm) of unreacted 5,5-dimethylhydantoin according to measurement by HPLC. After the solution was concentrated under a reduced pressure to remove about 1.80-1.90 L of methyl acetate, methyl tert-butyl ether (MTBE, 300 mL) was charged. After the reaction mixture was refluxed at 65-70° C. for 10-15 minutes, the solution was cooled to 50-55° C. over 0.5-1 hour and seeded with 500 mg of methyl 2-bromomethyl-6-nitrobenzoate at 45-50° C. The suspension was cooled to 20-25° C. and kept at 20-25° C. for 2-3 hours. The solids were collected by filtration, washed with 5-10° C. a cold mixture of heptane and MTBE in a volume ratio of 1:2 (2×100 mL), and dried to a constant weight at 20-25° C. under a vacuum at 100-120 torr. The yield of methyl 2-bromomethyl-6-nitrobenzoate was 185.2 g (66%), based on 200.0 g input of methyl 2-methyl-6-nitrobenzoate. The product was found to have a purity of >98% measured by HPLC based on area percentage, and a water content of <0.1% measured by Karl Fisher titration.

6.5.3. Preparation of (1S)-1-(3-ethoxy-4-methoxyphenyl)-2-methanesulfonyl-ethylamine After a mixture of (1S)-1-(3-ethoxy-4-methoxyphenyl)-2-methanesulfonyl-ethylamine N-acetyl-L-Leucine salt (1.10 kg, 2.46 moles), deionizer water (4.40 L), and dichloromethane (DCM, 5.50 L) was charged into a reaction vessel, a solution of sodium hydroxide (196.0 g, 4.90 moles) in 1.00 L of deionizer water was charged into the reaction vessel over about 5 minutes at 15-25° C. The resulting mixture was stirred for at least 10 minutes at 15-25° C. and then the aqueous and organic phases were allowed to separate. The pH of the upper aqueous phase was maintained or adjusted at pH 13-14. The phases were separated and the upper aqueous phase was extracted with DCM (2×4.4 L). The pH of the aqueous phase was maintained at 13-14 throughout the extractions. The DCM extracts were combined and washed with deionizer water (3.3 L) until the pH of the aqueous phase reached 11 or less. DCM was removed under vacuum below 35° C. The water content of the residual solid should be <0.1% w/was measured by Karl Fisher titration. The residual solid was dried azeotropically with more DCM. The solid was dried to a constant weight in vacuo at 30-35° C. to give (1S)-1-(3-ethoxy-4-methoxyphenyl)-2-methanesulfonyl-ethylamine as a white powder (639.0-672.0 g, 95-100% yield).

6.5.4. Preparation of (1S)-7-nitro-2-[1-(3-ethoxy-4-methoxyphenyl)-2-(methylsulfonyl)ethyl]isoindolin-1-one (1S)-7-nitro-2-[1-(3-ethoxy-4-methoxyphenyl)-2-(methylsulfonyl)ethyl]isoindolin-1-one was prepared by the following procedure. A mixture of methyl 2-bromomethyl-6-nitrobenzoate (100.0 g, 365 mmol, prepared previously in Example 6.5.2.), (1S)-1-(3-ethoxy-4-methoxyphenyl)-2-methanesulfonylethylamine (104.7 g, 383 mmol, prepared previously in Example 6.5.3.), sodium hydrogen carbonate (67.5 g, 8.03 moles, from Aldrich Chemicals) and dimethyl formamide (500 mL) was charged into a 1-L 3-necked flask at room temperature under nitrogen. The reaction mixture was gradually heated to an internal temperature of 70-75° C. for two hours until there was less than <2% of unreacted methyl 2-bromomethyl-6-nitrobenzoate. The reaction mixture was gradually heated to an internal temperature of 95-100° C. for 18 hours. The reaction mixture was cooled to 20-25° C. and transferred to an 1-L addition funnel. After purified water (1500 mL) was charged into a 5-L 3-necked flask, the reaction mixture in the addition funnel was added into water in the 5-L 3-necked flask at room temperature over 1-2 hours maintaining an internal temperature below 30° C. The reaction mixture was stirred for 2 hours at room temperature. The solid was filtered out under vacuum, washed with water (3×300 mL) and methanol (2×400 mL), and then charged into a 2-L 3-necked flask followed by methanol (1000 mL). The mixture was refluxed for 1 hour. The mixture was cooled to room temperature. The solid was collected by filtration under vacuum, washed with 200 mL methanol (2 vol), and dried to a constant weight at 40-45° C. under a vacuum at 100-120 torr. The yield of (1S)-7-nitro-2-[1-(3-ethoxy-4-methoxyphenyl)-2-(methylsulfonyl)ethyl]isoindolin-1-one was 123.0 g (78%), based on 100.0 g input of methyl 2-bromomethyl-6-nitrobenzoate. The product was found to have a purity of >99% measured by HPLC based on area percentage, and a water content of <0.1% measured by Karl Fisher titration.

6.5.5. Alternative Preparation of (1S)-7-nitro-2-[1-(3-ethoxy-4-methoxyphenyl)-2-(methylsulfonyl)ethyl]isoindolin-1-one (1S)-7-nitro-2-[1-(3-ethoxy-4-methoxyphenyl)-2-(methylsulfonyl)ethyl] isoindolin-1-one was also prepared by the following procedure. A mixture of methyl 2-bromomethyl-6-nitrobenzoate (100.0 g, 365 mmol, prepared previously in Example 6.5.2.), (1S)-1-(3-ethoxy-4-methoxyphenyl)-2-methanesulfonyl-ethylamine (104.7 g, 383 mmol, prepared previously in Example 6.5.3.), and potassium carbonate powder (100.8 g, 730 mmol, from Aldrich Chemicals) was suspended in acetonitrile (500 mL) at room temperature. The reaction mixture was refluxed at 81-83° C. for about two hours until there was less than 2% of unreacted methyl 2-bromomethyl-6-nitrobenzoate. After the reaction mixture was cooled to 45-50° C., methanol (200 mL) was charged over 5-10 minutes. After the mixture was allowed to cool to 20-25° C. and stirred for 2 hours, deionizer water (1.40 L) was charged over 0.5-1 hour and stirred at 20-25° C. for 30 minutes and at 0-5° C. for 1-2 hours. The solid was filtered, washed with deionizer water (3×300 mL), and dried to <10% of water content as measured by Karl Fisher titration. The solid was suspended in methanol (750 mL) and refluxed for 1-1.5 hours. The suspension was cooled to 0-5° C. over 1.5-2 hours and kept at 0-5° C. for 1-1.5 hours. The solid was filtered, washed with 0-5° C. methanol (2×200 mL) and heptane (200 mL), and then dried at 40-45° C. under vacuum to a constant weight. The yield of (1S)-7-nitro-2-[1-(3-ethoxy-4-methoxyphenyl)-2-(methylsulfonyl)ethyl]isoindolin-1-one was 148.0 g (93%), based on 100.0 g input of methyl 2-bromomethyl-6-nitrobenzoate. The product was found to have a purity of >99% measured by HPLC based on area percentage, and a water content of <1.0% measured by Karl Fisher titration.

6.5.6. Preparation of Compound B

A mixture of (1S)-7-nitro-2-[1-(3-ethoxy-4-methoxyphenyl)-2-(methylsulfonyl)ethyl]isoindolin-1-one (60 g, 138 mmol, prepared previously in Example 6.5.5.), 10% Pd/C (50% wet, 2.4 g, 4 wt %, from Johnson Matthey, London, UK), ethyl acetate (780 mL) was charged into a Parr-vessel at room temperature under nitrogen. After the mixture was purged with nitrogen three times and with hydrogen three times, the reaction mixture was heated to 40° C. and then the heat was removed. The reaction mixture was stirred with hydrogen at a pressure between 40-45 psi over 4-6 hours until there was <3% of the hydroxylamine intermediate. The reaction mixture was cooled to 20-25° C. The reaction mixture was filtered through a celite bed (1 inch thickness) and then bed-washed with ethyl acetate (120 mL). The filtrate was transferred to a 3-L 3-necked flask equipped with a 50-mL addition funnel. After N,N-diisopropylethylamine (29 mL, 165 mmol) was charged into the flask, the addition funnel was charged with cyclopropylcarbonyl chloride (13.0 mL, 145 mmol, from Aldrich Chemicals). The cyclopropylcarbonyl chloride was added at room temperature over 1-2 hours at an internal temperature below 30° C. The reaction mixture was stirred for 2-4 hours at room temperature. After heptane (300 mL) was added, the reaction mixture was stirred for 4-6 hours. The solid was collected by filtration under vacuum, washed with 2N HCl (2×300 mL), water (2×300 mL) and then heptane (2×300 mL). The crude product was dried at 40-45° C. under a vacuum at 100-120 torr to a constant weight. The yield of crude Compound B was 58 g (88%), based on 60.0 g input of (1S)-7-nitro-2-[1-(3-ethoxy-4-methoxyphenyl)-2-(methylsulfonyl)ethyl]-isoindolin-1-one.

6.5.7. Recrystallization of Compound B

A mixture of crude Compound B (95.2 g, prepared previously in Example 6.5.6.) and tetrahydrofuran (THF, 1.43 L) was charged into a 3 L flask at 20-25° C. under nitrogen. The suspension was heated to 60-65° C. until dissolution was achieved. The suspension was filtered at 45-50° C. and the solid was rinsed with 95 mL of THF prewarmed at 45-55° C. After about 950-1150 mL of THF was distilled off at normal pressure over 30-60 minutes, absolute ethanol (950 mL) was charged at 55-60° C. over 5-10 minutes. About 350-400 mL of solvents was removed at normal pressure until the internal temperature rose to 72-74° C. The resulting suspension was refluxed at 72-75° C. for 30-60 minutes, cooled to 20-25° C. over 1-2 hours and kept at 20-25° C. for another 1-2 hours. The solid was collected by filtration under vacuum, washed with absolute ethanol (240-280 mL) and heptane (240-280 mL), and then dried in tray at 50-55° C. in vacuo at 130-140 torr to a constant weight. The yield of the off-white crystalline product was (88.0-91.0 g, 92-96%).

The compounds described herein may also be prepared according to the process described in U.S. Patent Publication No. 2010/0168475, the disclosure of which is hereby incorporated by reference in its entirety.

6.6. Example 6

Effects of PDE4 Inhibitors Compound A and Compound B in Combination with Cyclosporine A, Methotrexate, and Etanercept on Rheumatoid Arthritis and Psoriasis Associated Cytokine Production in Stimulated T Cells.

6.6.1. Procedure for Peripheral Blood Mononuclear Cells Multiplex Assay

Purification of Human Peripheral Blood Mononuclear Cells

Fifty milliliters (50 mL) of human buffy coat were divided into two 25 mL aliquots in two 50 mL conical tubes containing 25 mL of sterile Hank's Buffered Salt Solution (HBSS). The tubes were gently mixed by inverting several times. Fifteen milliliters (15 mL) of room temperature Ficoll-Paque Plus (Amersham Bioscience; cat#17-1440-02) were aliquoted into four 50 mL conical tubes. Then 25 mL of the buffy coat/HBSS mixture were gently and slowly layered on top of the Ficoll. The samples were centrifuged (Eppendorf Centrifuge 5810R) at 450 rpm (Rotor A-4-81) for 35 minutes. The top layer containing plasma was discarded. The interface containing mononuclear cells was transferred into two 50 mL conical tubes. Both conical tubes were filled to a total volume (50 mL) with HBSS and centrifuged at 1200 rpm for 10 minutes. The cells were washed again in HBSS and centrifuged at 1000 rpm for 10 minutes. Human red blood cell lysis buffer (5 mL) (Boston Bioproducts cat#IBB-197) was added to the cell pellets and incubated for 5 minutes at room temperature. Phosphate buffered saline (PBS; 45 mL) was added to the conical tubes and centrifuged at 1200 rpm for 10 minutes. The cell pellets were combined and resuspended in 20 mL Roswell Park Memorial Institute (RPMI) complete medium (RPMI/5% human sera/1× penicillin/streptomycin [pen/strep]/L-glutamine [L-gln]) and the cells counted.

For Staphylococcal Enterotoxin B (SEB)-Treated PBMCs

Isolated PBMCs were plated into 96-well plates and compound (starting at 1600 ng/ml and diluted 1:4) was added for 1 hour at 37° C. Staphylococcal enterotoxin B (Sigma) was then added at a final concentration of 100 ng/ml and cells were incubated for 18 hours at 37° C.

Supernatants were then harvested for luminex assay.

6.6.2. Procedure for Anti-CD3 Monoclonal Antibody-Stimulated T Cells Multiplex Assay Purification and Treatment of Human T Cells Tissue culture plates (96-well flat-bottom) were coated with anti-CD3 mAb (2.5 µg/mL) and incubated at 37° C. for 4 hours. The plates were washed 3 times with 100 µl/well of Complete Media (RPMI 1640 w/10% heat inactivated fetal bovine serum (FBS), 1% pen/strep/1% L-gln) just prior to adding T cells. Peripheral blood mononuclear cells ($5\times10^8$ cells; prepared as described above) were seeded in five 10 cm tissue culture dishes (10 mL each). The adherent monocyte portion was depleted by incubation for 30-60 minutes at 37° C. The dishes were rinsed with medium to remove all non-adherent PBMCs. The non-adherent PBMCs were counted and $2\times10^8$ cells were removed, centrifuged for 10 minutes at 1200 rpm, and the volume adjusted to 4.0 mL using Complete Media. The following antibody mixture was prepared by mixing on a shaker at room temperature (RT) for 30 minutes in a Falcon tube (5 mL):

sheep anti-mouse IgG beads (600 µl; Dynal Cat. No 110.31),
anti-CD16 (30 µl; BD Pharmingen Cat. No. 555404),
anti-CD33 (30 µl; BD Pharmingen Cat. No. 555449),
anti-CD56 (30 µl; BD Pharmingen Cat. No. 555514).

Upon completion, anti-CD19 beads (460 µl; Dynal Cat. No. 111.43) and anti-CD 14 beads (112 µl; Dynal Cat. No. 111.49) were added to the Falcon tube/antibody mixture. The mixture was washed 3 times with Complete Media using a magnet and pipette aspiration. The non-adherent PBMCs ($2\times10^8$ cells in 4.0 mL) were added and the tube was rotated at 4° C. for 30 minutes. The cells were separated from the beads using a magnet for negative selection. The T cells were then collected, counted, and resuspend in Complete Media. The T cell concentration was adjusted to $2.5\times10^5$ cells/180 µl ($1.39\times10^6$ cells/mL) and added to the plate wells (180 µl/well). Test compound (20 µl of 10× concentration) was immediately added into the wells containing the T cells. Compound A, Compound B, cyclosporine A (Sigma), methotrexate (Sigma) and Enbrel (obtained by prescription) was tested starting at 400 ng (1600 ng/ml and diluted 1:4). The drug concentrations used in the assay were determined according to the pharmacokinetic studies preformed in RA patients (Table 2) The T cells plates were incubated for 2 days at 37° C. at 5% $CO_2$. Fifty μl of supernatant from each well were then transferred into 3 new round-bottomed 96 well plates and stored at −20° C. for Luminex analysis. Duplicate wells were performed for each sample. See Fox et al., "Combined oral cyclosporin and methotrexate therapy in patients with rheumatoid arthritis elevates methotrexate levels and reduces 7-hydroxymethotrexate levels when compared with methotrexate alone." *Rheumatology* (Oxford). 2003; 42(8): 989-94.

TABLE 2

Pharmcokinetic Data for Study Drugs

| Drugs | Cmax (ng/ml) | Cmin (ng/ml) | Comment |
|---|---|---|---|
| Cyclosporin A | 800 | 250-350 | RA patients |
| Methotrexate | 300-1040 | | Depending on RA patients |
| Etanercept (Enbrel) | RA patient 6 months 25-mg biweekly: 3000 (1700 to 5600) RA patients 50-mg weekly: 2400 ± 1500 | 1200 ± 700 | Bioavailability 76% |
| Compound A | 419 | 4.9 | 20-mg; day-7 |
| Compound B | 195 | 40 | 200-mg day-7 |

RA = rheumatoid arthritis.

6.6.3. Luminex Analysis

The cytokines IFN-γ, IL-2, IL-4, IL-10, IL-13, IP-1α, MIP-1α, MIP1β and TNF-α were analyzed in a nine-plea format using neat supernatants. Data analysis was performed using Upstate Beadview software. Data was graphed as % control (DMSO) using Prism v5 (GraphPad). Potential drug combination synergy was first identified by visual inspection of the graphed data along the linear portion of the curve. Upon synergy identification, the graphed data was entered into the Compusyn Program (Combosyn, Inc.) which calculated the combination index (CI) for each data point along the concentration curve (Table 3).

TABLE 3

Meaning of Combination Index Values

| CI | Description |
|---|---|
| <1.0 | synergy |
| =1.0 | additive |
| >1.0 | non-additive |

CI = combination index;
< = less than;
> = greater than

Figure 4A:
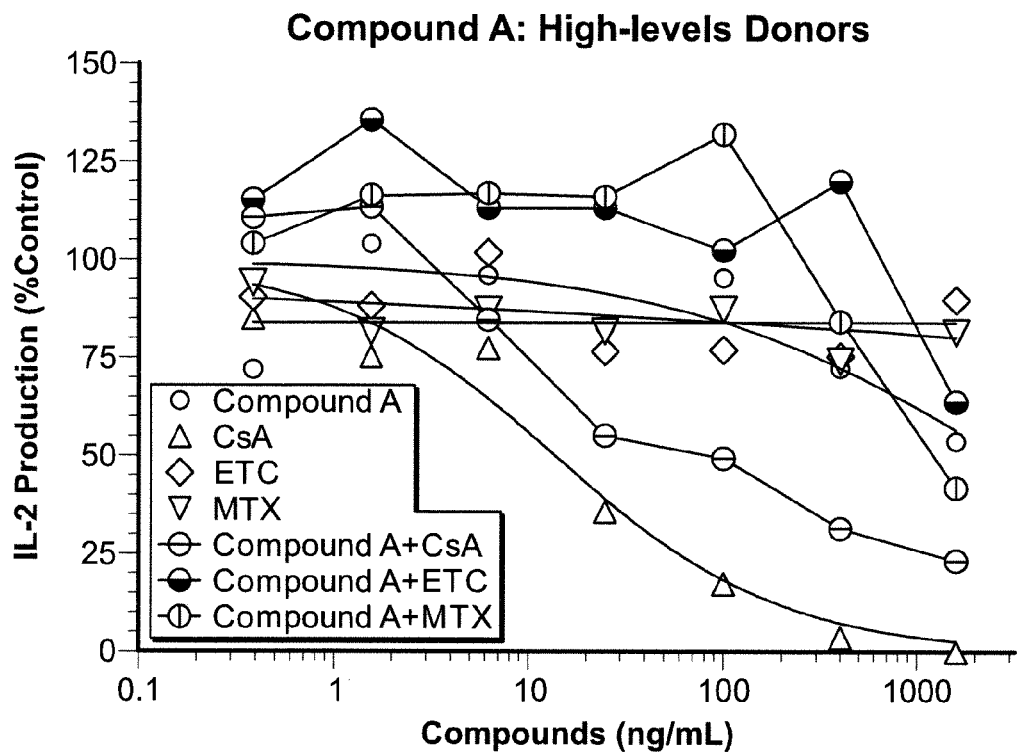
Figure 4B:
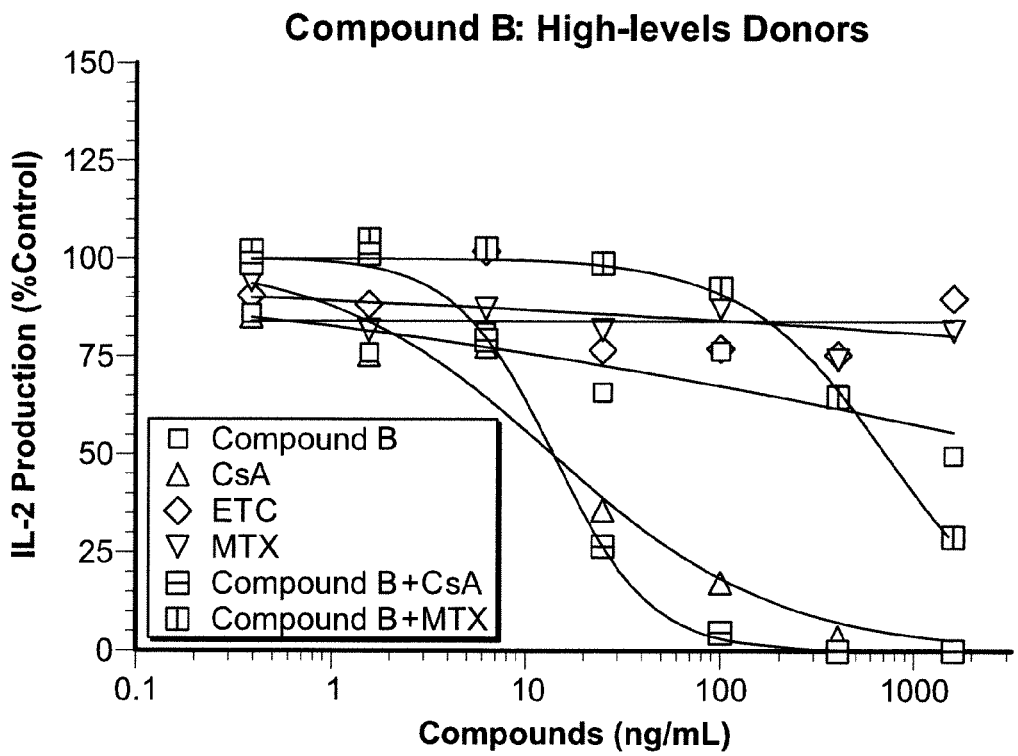
Figure 5A:
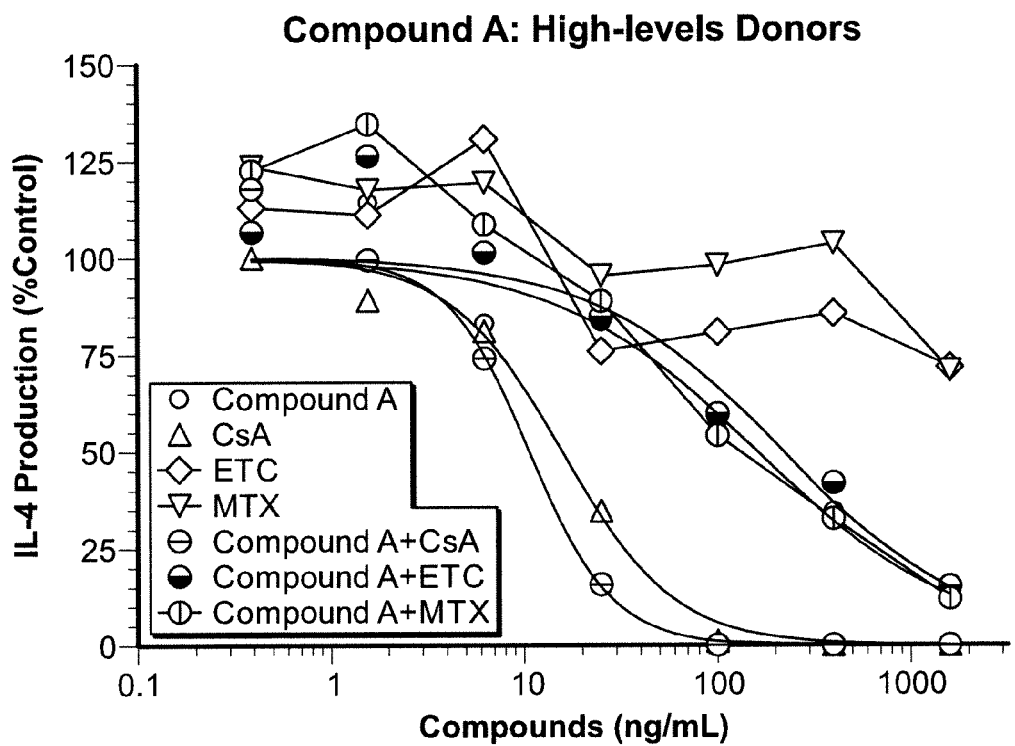
Figure 5B:
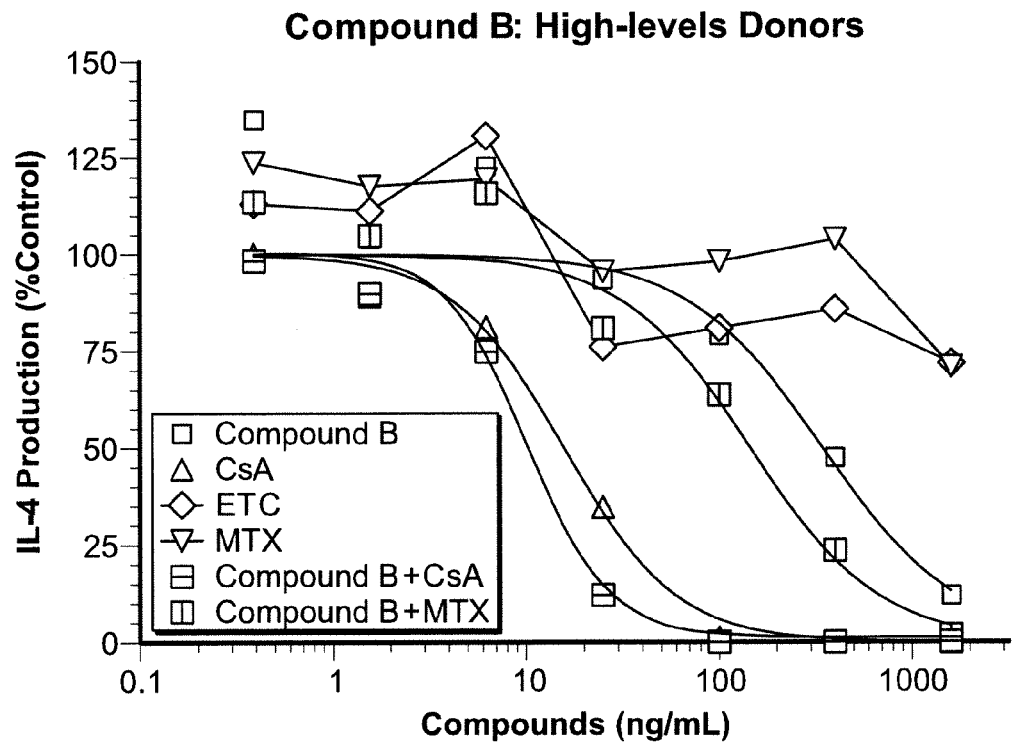

6.6.4. Phosphodiesterase 4 Inhibitor in Combination with Cyclosporine, Etanercept or Methotrexate in Anti-CD3 Monoclonal Stimulated Human T Cells: Responses from the High Cytokine Levels Donor In the anti-CD3 mAb-stimulated T cells derived from a donor with high cytokine levels, the combination effect of Compound A with either CsA or ETC synergistically inhibited IFN-γ (FIG. 3A), IL-13 (FIG. 7A), IP-10 (FIG. 8A), MIP-1α (FIG. 9A), MIP-1β FIG. 10A), and TNF-α (FIG. 11A) production at a minimum of one of the tested concentrations (Table 4). The combined inhibitory effect of Compound A and MTX for the aforementioned cytokines was non-additive with the exception of INF-γ which was not determinable (ND) (Table 4). Synergistic inhibition was also observed for IL-10 production with the Compound A and CsA or MTX combination at one of the test concentrations but was ND for the Compound A/ETC combination (FIG. 6 and Table 4). At the maximum test concentrations (1600 ng/ml), the Compound A/MTX combination synergistically inhibited IL-2 production; however, Compound A in combination with ETC or CsA was non-additive for the inhibition of IL-2 production. Notably, the Compound A/CsA combination was actually antagonistic (FIG. 4A and Table 4). The inhibition of IL-4 production was non-additive in response to the Compound A and ETC or MTX combinations but was additive for the Compound A/CsA combination (FIG. 5A and Table 4).

Figure 9B:
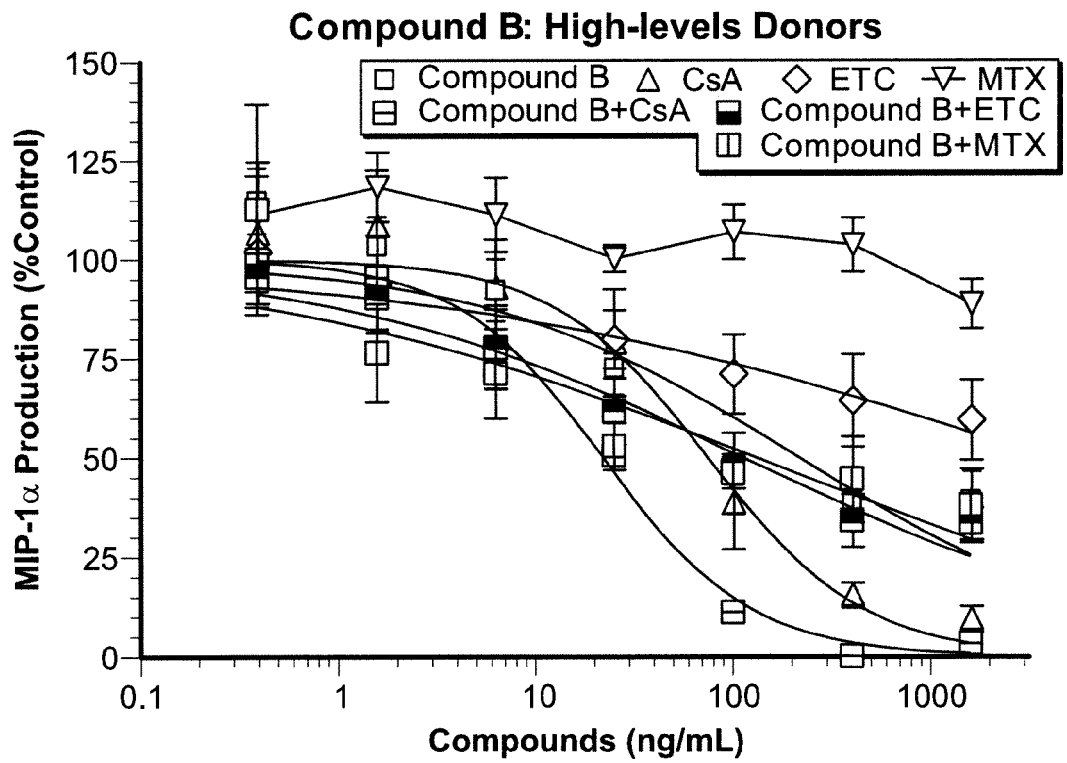

Compound B in combination with CsA, ETC or MTX in the stimulated T cells derived from donors with high cytokine levels and at a minimum of one of the tested concentrations synergistically inhibited MIP-1α (FIG. 9B) production (Table 4). The Compound B/CsA combination was also synergistic for the inhibition IFN-γ (FIG. 3B), IL-4 (FIG. 5B), IL-10 (FIG. 6B), and IL-13 (FIG. 7B), IP-10 (FIG. 8B), MIP-1β (FIG. 10B), and TNF-α (FIG. 11B) production at least at one of the test concentrations but the effect was non-additive for IL-2 production FIG. 4B) (Table 4). Additionally, the Compound B/MTX combination synergistically inhibited IL-2 (FIG. 4B), IL-4 (FIG. 5B), and MIP-1β (FIG. 10B) production (Table 4) but the effects of this combination were non-additive for the inhibition of IL-10 (FIG. 6B), IL-13 (FIG. 7B), IP-10 (FIG. 8B), and TNF-α (FIG. 11B) production but was ND for IFN-γ production (FIG. 3B) (Table 4). The Compound B/ETC was not tested for the cytokines profiled in this study with the exception of MIP-α (mentioned above; FIG. 9B) (Table 4).

TABLE 4

Summary of Effects for Phosphodiesterase 4 Inhibitors in Combination with Cyclosporine, Etanercept, or Methotrexate: T Cells from High-levels Donor

| | | Compound A | | | Compound B | | |
|---|---|---|---|---|---|---|---|
| Cytokine | CsA | ETC | MTX | CsA | ETC | MTX |
| IFN-γ | Synergy (25 ng/mL; CI = 0.31) | Synergy (25-1600 ng/mL; CI = 0.0066-0.038) | ND | Synergy (25 ng/mL; CI = 0.28) | Not tested | ND |
| IL-2 | Non-additive (antagonistic) | Non-additive | Synergy (1600 ng/mL; CI = 0.39) | Non-additive | Not tested | Synergy (1600 ng/mL; CI = 0.0013) |

TABLE 4-continued

Summary of Effects for Phosphodiesterase 4 Inhibitors in Combination with
Cyclosporine, Etanercept, or Methotrexate: T Cells from High-levels Donor

| Cytokine | Compound A | | | Compound B | | |
|---|---|---|---|---|---|---|
| | CsA | ETC | MTX | CsA | ETC | MTX |
| IL-4 | Additive (25 ng/mL: CI = 1.01) | Non-additive | Non-additive | Synergy (25 ng/mL; CI = 0.88) | Not tested | Synergy (25-400 ng/mL; CI = 0.17-0.76) |
| IL-10 | Synergy (6.25-25 ng/mL; CI = 0.27-0.43) | ND | Synergy (25-400 ng/mL; CI = 0.11-0.62) | Synergy (6.25-25 ng/mL; CI = 0.26-0.39) | Not tested | Non-additive |
| IL-13 | Synergy (25 ng/mL; CI = 0.77) | Synergy (6.25-1600 ng/mL; CI = 0.088-0.39) | Not additive | Synergy (25 ng/mL; CI = 0.85) | Not tested | Not additive |
| IP-10 | Synergy (100 ng/mL; CI = 0.095) | Synergy (25-1600 ng/mL; CI = 0.039-0.27) | Non-additive | Synergy (100 ng/mL; CI = 0.055) | Not tested | Non-additive |
| MIP-1α | Synergy (25-100 ng/mL; CI = 0.27-0.59) | Synergy (25-100 ng/mL; CI = 0.18-0.55) | Non-additive | Synergy (6.25-100 ng/ml: CI = 0.12-0.38) | Synergy (25-100 ng/mL; CI = 0.22-0.65) | Synergy (6.25-100 ng/mL; CI = 0.041-0.44) |
| MIP-1β | Synergy (100 ng/ml; CI = 0.35) | Synergy (1600 ng/mL; CI = 0.35) | Non-additive | Synergy (25-100 ng/mL; CI = 0.25-0.88) | Not tested | Synergy (1600 ng/mL; CI = 0.14) |
| TNF-α | Synergy (6.25-25 ng/mL; CI = 0.80-0.87) | Synergy (0.39-25 ng/mL; CI = 0.11-0.16) | Non-additive | Synergy (25 ng/mL; CI = 0.74) | Not tested | Non-additive |

CI = combination index;
IL = interleukin;
INF-γ = interferon-gamma;
IP-10 = interferon-inducible protein 10;
MIP-1α(β) = macrophage inflammatory protein-1 alpha (beta);
ND = not determinable;
TNF-α = tumor necrosis factor-alpha.
Non-additive: the percent of PDE4 inhibitor in combination with another agent ≤ either drug acting alone; CI > 1.
Additive: [(100 − % PDE4 inhibitor) + (100 − % combinatorial agent)] = (100 − % PDE4 inhibitor with combinatorial agent); CI = 1.0.
Synergy: [(100 − % PDE4 inhibitor) + (100 − % other agent)] < (100 − % PDE4 inhibitor with combinatorial agent); CI < 1.

6.6.5. Phosphodiesterase 4 Inhibitor in Combination with Cyclosporine, Etanercept or Methotrexate in Anti-CD3 Monoclonal Stimulated Human T Cells: Responses from the Low Cytokine Levels Donor In the anti-CD3 mAb-stimulated T cells from the low-levels donors (n=5), the combination effect of the Compound A with either CsA synergistically inhibited IFN-γ (FIG. 12A), IL-4 (FIG. 14A), IL-10 (FIG. 15A), IL-13 (FIG. 16A), IP-10 (FIG. 17A), MIP-1α (FIG. 18A), MIP-1β (FIG. 19A), and TNF-α (FIG. 20A) production at a minimum of one of the tested concentrations, and was non-additive for the inhibition of IL-2 (FIG. 13A) production (Table 5). Compound A in combination with ETC also synergistically inhibited IL-4 (FIG. 14A), IL-10 (FIG. 15A), IL-13 (FIG. 16A), IP-10 (FIG. 17A), and MIP-1α (FIG. 18A) production at minimum of one of the test concentrations and was non-additive for inhibition of IFN-γ (FIG. 12A), IL-2 (FIG. 13A), MIP-1β (FIG. 19A) and TNF-α (FIG. 20A) production (Table 5). The Compound A/MTX combination was non-additive for the inhibition of all the cytokines profiled (Table 5).

Compound B in combination with CsA, ETC or MTX in the low-levels donor stimulated T cell samples (n=5) and at a minimum of one of the tested concentrations synergistically inhibited MW-1α (FIG. 18B) (Table 5). The Compound A/CsA combination displayed inhibitory synergy at one of the test concentrations for IFN-γ (FIG. 12B), IL-2 (FIG. 13B), IP-10 (FIG. 17B), and MIP-1β (FIG. 19B) production (Table 5). A non-additive response was obtained for TNF-α (FIG. 20B) production with the Compound A/CsA combination and IL-4, IL-10, and IL-13 were not tested. Compound B in combination with ETC also demonstrated synergistic inhibitory responses at least for one of the test concentrations for IFN-γ (FIG. 12B), IL-4 (FIG. 14B), IL-10 (FIG. 15B), and IP-10 (FIG. 17B) production (Table 5), and displayed non-additive inhibitory responses for IL-2 (FIG. 13B), IL-13 (FIG. 16B), MIP-1β (FIG. 179B), and TNF-α (FIG. 20B) production (Table 5). The Compound B/MTX combination demonstrated non-additive inhibitory response for all of the cytokines profiled except MIP-1α (mentioned above; Table 5).

TABLE 5

Summary of Effects for Phosphodiesterase 4 Inhibitors in Combination with
Cyclosporine, Etanercept or Methotrexate: T Cells from Low-levels Donors

| Cytokine | Compound A | | | Compound B | | |
|---|---|---|---|---|---|---|
| | CsA | ETC | MTX | CsA | ETC | MTX |
| IFN-γ | Synergy (6.25 ng./ml; CI = 0.81) | Non-additive | Non-additive | Synergy (6.35-100 ng/mL; CI = 0.0012-0.68) | Synergy (25-100 ng/mL; CI = 0.13-.39) | Non-additive |
| IL-2 | Non-additive | Non-additive | Non-additive | Synergy (6.25-25 ng/mL; CI = 0.0015-0.060) | Non-additive | Non-additive |
| IL-4 | Synergy (6.25 ng/mL; CI = 0.069) | Synergy (100 ng/mL; CI = 0.15) | Non-additive | Not tested | Synergy (6.25-400 ng/mL; CI = 0.16-0.63) | Non-additive |
| IL-10 | Synergy (25-100 ng/mL: CI = 0.085-0.17) | Synergy (25 and 100 ng/mL; CI = 0.038-0.10) | Non-additive | Not tested | Synergy (100 ng/mL; CI = 0.14) | Non-additive |
| IL-13 | Synergy (6.25 ng/mL: CI = 0.040) | Synergy (25-100 ng/mL: CI = 0.025-0.033) | Non-additive | Not tested | Non-additive | Non-additive |
| IP-10 | Synergy (25-100 ng/mL: CI = 0.20-0.35) | Synergy (6.25-25 ng/mL; CI = 0.075-0.13) | Non-additive | Synergy (6.25 ng/mL; CI = 0.094) | Synergy (1.56-25 ng/mL; CI = 0.027-0.14) | Non-additive |
| MIP-1α | Synergy (25-100 ng/mL: CI = 0.28-0.71) | Synergy (625-100 ng/mL: CI = 0.089-0.58) | Non-additive | Synergy (25-100 ng/mL: CI = 0.27-0.65) | Synergy (6.25-100 ng/mL: CI = 0.25-0.65) | Synergy (1.5625-100 ng/mL: CI = 0.012-0.38) |
| MIP-1β | Synergy (25 ng/mL: CI = 0.40) | Non-additive | Non-additive | Synergy (25-100 ng/mL: CI = 0.27-0.37) | Non-additive | Non-additive |
| TNF-α | Synergy (25-100 ng/mL: CI = 0.4/-0.61) | Non-additive | Non-additive | Non-additive | Non-additive | Non-additive |

CI = combination index;
IL = interleukin;
INF-γ = interferon-gamma;
IP-10 = interferon-inducible protein 10;
MIP-1α(β) = macrophage inflammatory protein-1 alpha (beta);
TNF-α = tumor necrosis factor-alpha.
Non-additive: the percent of PDE4 inhibitor in combination with another agent ≤ either drug acting alone; CI > 1.
Additive: [(100 − % PDE4 inhibitor) + (100 − % combinatorial agent)] = (100 − % PDE4 inhibitor with combinatorial agent); CI = 1.0.
Synergy: [(100 − % PDE4 inhibitor) + (100 − % other agent)] < (100 − % PDE4 inhibitor with combinatorial agent); CI < 1.

Figure 25B:
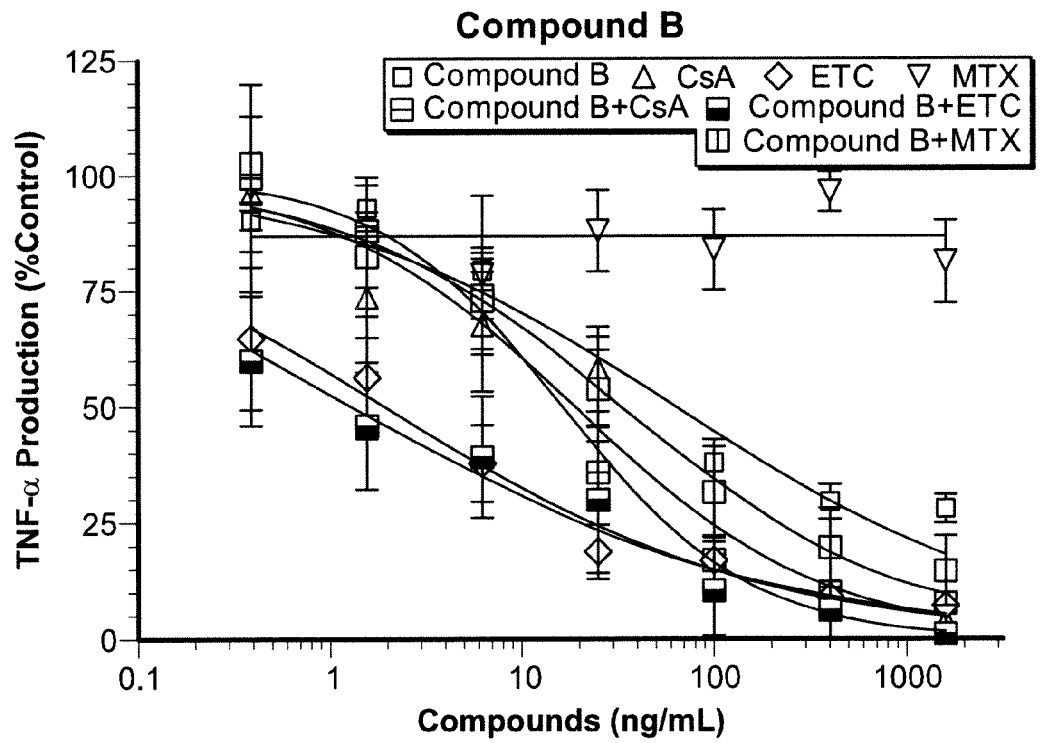

6.6.6. Phosphodiesterase 4 Inhibitor in Combination with Cyclosporine, Etanercept or Methotrexate: Response in Staphylococcal Enterotoxin B-Treated Peripheral Blood Mononuclear Cells In the SEB-treated PBMCs samples (n=6), Compound A or Compound B in combination with CsA synergistically inhibited IL-10 (FIGS. 21A and B), IP-10 (FIGS. 22A and B), MIP-1α (FIGS. 23A and B), MIP-1β (FIGS. 24A and B) and TNF-α (FIGS. 25A and B) production for at least one of the tested concentrations (Table 6). Also, Compound A or Compound B combined with ETC for at least one test concentrations synergistically inhibited IL-10 (FIGS. 21A and B), IP-10 (FIGS. 22A and B), and MIP-1α (FIGS. 23A and B) production and displayed non-additive effects for inhibition of MIP-1β (FIGS. 24A and B) and TNF-α (FIGS. 25A and B) production (Table 6). The Compound A/MTX combination showed non-additive inhibition for all of the cytokines profiled in this assay; however, the Compound B/MTX combination demonstrated non-additive inhibition for all of the profiled cytokines except TNF-α production which showed inhibitory synergy at the 400 ng/ml concentration (FIG. 25B and Table 6).

6.6.7. Compound A Inhibits T Cell Regulatory Cytokine IL-7 Gene Expression

The T cell regulatory cytokine IL-7, produced by chondrocytes and synoviocytes, plays a role in inflammatory joint diseases such as arthritis and in bone damage. Long, D. et al. *Arthritis Res Ther.*, 2008, 10(1): R23. In particular, IL-7 messenger ribonucleic acid (mRNA) and protein levels were increased in synovial fluid of spondylarthritis and rheumatoid arthritis (RA) patients. Rihl, M. et al., *Arthritis Rheum.*, 2008, 58(11): 3430-3435. In normal primary human chondrocytes stimulated with IL-1, IL-6 and IL-6 receptor (IL-6R), Compound A (0.1-10 μM) significantly inhibited IL-7 gene expression in a dose-dependent manner In this assay Compound A was a more effective inhibitor of IL-7 gene expression than methotrexate and etanercept within dose ranges that encompassed their respective maximum plasma concentrations ($C_{max}$–MTX=400 and ETC=1600 ng/ml). In stimulated primary human normal chondrocytes, Compound A inhibited expression of the synovial tissue biomarkers intercellular adhesion molecule 1 (ICAM-1) and alpha-v-beta-3 ($\alpha$v$\beta$3) integrin expression. Similarly in rheumatoid arthritis synovial fibroblasts stimulated with IL-1, IL-6 and IL-6R, Compound A (0.1-10 μM) significantly inhibited IL-7 gene expression in a dose-dependent manner, while MTX and ETC had no significant effects.

lation according to manufacturers' instructions (Qiagen RNAEasy kit). Purified RNA was reverse transcribed into cDNA with thermal cycler for real-time reverse transcriptase polymerase chain reaction (RTPCR) analysis. Interleukin-7 gene expression assays were carried out using the 7500 Real Time PCR system. A GAPDH gene expression assay control was run for each sample and was used as a normalization

TABLE 6

Summary of Effects for Phosphodiesterase 4 Inhibitors in Combination with Cyclosporine, Etanercept or Methotrexate in Staphylococcal Enterotoxin B-Treated Perpherial Blood Mononuclear Cells

| | Compound A | | | Compound B | | |
|---|---|---|---|---|---|---|
| Cytokine | CsA | ETC | MTX | CsA | ETC | MTX |
| IL-10 | Synergy (6.25-100 ng/mL; CI = 0.056-0.17) | Synergy (25-100 ng/mL; CI = 0.04-0.11) | Non additive | Synergy (25-100 ng/mL; CI = 0.010-0.040) | Synergy (100 ng/mL; CI = 0.17)) | Non additive |
| IP-10 | Synergy (25-100 ng/mL; CI = 0.31-0.47) | Synergy (6.25-25 ng/mL; CI = 0.12-0.17) | Non additive | Synergy (100 ng/mL; CI = 0.61) | Synergy (1.56-6.25 ng/mL; CI = 0.03-0.14) | Non additive |
| MIP-1$\alpha$ | Synergy (6.25-100 ng/mL; CI = 0.14-0.63) | Synergy (6.25-25 ng/mL; CI = 0.070-0.15) | Non additive | Synergy (6.25-100 ng/mL; CI = 0.15-0.33) | Synergy (25 ng/mL; CI = 0.22) | Non additive |
| MIP-1$\beta$ | Synergy (100 ng/mL; CI = 0.86) | Non additive | Non additive | Synergy (25-100 ng/mL; CI = 0.24-0.42) | Non additive | Non additive |
| TNF-$\alpha$ | Synergy (25 ng/mL; CI = 0.79) | Non additive | Non additive | Synergy (25-100 ng/mL; CI = 0.75-0.77) | Non additive | Synergy (400 ng/mL; CI = 0.24) |

CI = combination index;
IL = interleukin;
IP-10 = interferon-inducible protein 10;
MIP-1$\alpha$($\beta$) = macrophage inflammatory protein-1 alpha (beta);
TNF-$\alpha$ = tumor necrosis factor-alpha.
Non-additive: the percent of PDE4 inhibitor in combination with another agent ≤ either drug acting alone; CI > 1.
Additive: [(100 − % PDE4 inhibitor) + (100 − % combinatorial agent)] = (100 − % PDE4 inhibitor with combinatorial agent); CI = 1.0.
Synergy: [(100 − % PDE4 inhibitor) + (100 − % other agent)] < (100 − % PDE4 inhibitor with combinatorial agent); CI < 1.

6.6.8. Compound A in Combination with Etanercept, Methotrexate and Prednisone: Response in T Cell Regulatory Cytokine IL-7 Assay IL-7 Gene Expression Assay: The effect of Compound A in combination with Etanercept, methotrexate and prednisone against IL-7 production were tested in rheumatoid arthritis patient-derived synovial fibroblasts. Normal primary human chondrocytes and rheumatoid arthritis synovial fibroblasts purchased from Asterand (Detroit, Mich.) were thawed into a T-75 flask and cultured for 2-3 weeks to reach confluency. The media was 20% premium non-heat inactivated FBS-DMEM/F-12 (Invitrogen 11330-032)+1% pen/strep and 1% L-Glutamine. The cells (1.5 to 2.0×105 cells) were plated into 6-well plates containing 2 ml of complete media. Upon reaching 90% confluency (usually in 1-2 days post-plating), the cells were serum starved for 20 hours by replacing the complete media with 2 ml serum-free media. The cells were treated with the test compounds for 1 hour at 37° C. (0.25% final DMSO concentration). After drug treatment, the cells were incubated for 18 hours at 37° C. with stimulatory cytokines IL-1$\beta$ (10 ng/ml), IL-6 (10 ng/ml), and IL-6R (20 ng/ml). The cells were then washed with cold PBS. Ribonucleic acid (RNA) was isolated by adding 600 μl RLT lysis buffer (Qiagen RNAEasy kit cat#74104), passing the cells through the Qiashredder (Qiagen cat#23800) followed by RNA isocontrol. For each gene, samples within each experiment were normalized to 0.25% DMSO treatment.

Cell Surface Protein Expression Assay: Normal primary human chondrocyte were thawed into a T-75 flask and grown for 2-3 weeks to reach confluency in 20% premium non-heat inactivated FBS-DMEM/F-12 (Invitrogen 11330-032)+1% pen/strep and 1% L-Glutamine. The cells were plated (1.0× 106 cells/10 ml of complete media) in a 100×20 mm tissue culture plate. The next day, the media was replaced with 10 ml serum-free media for 20 min to serum starve the cells. Compound A (0.1-10 μM) was added for 1 hour at 37° C. (0.25% final DMSO). In addition, cytokines IL-1$\beta$ (10 ng/ml), IL-6 (10 ng/ml), and IL-6R (20 ng/ml) were added and the cells continued incubation overnight (18 hours) at 37° C. The cells were harvested by a non-enzymatic cell dissociation solution (Millipore S-004-B) then washed once in cold stain buffer (BD Pharmigen 554656) at 300×g for 5 minutes. The cells were resuspended and aliquoted into three 5 ml round bottom tubes plus two additional aliquots for control. The cells were washed again in cold stain buffer at 300×g for 5 minutes. The cells were stained with PE mouse anti-human: CD54 (ICAM-1) (BD Pharmigen 555511) and Integrin $\alpha$V$\beta$3 anti (Millipore MAB1976H). The samples were vortexed and incubated for 30 minutes at 4° C. while being protected from light. Two isotype controls, PE mouse IgG1 k (BD Pharmigen 555749) and IgG1 (Millipore CBL600P) were also tested in the untreated-DMSO sample. The samples were washed twice in stain buffer at 300×g for 5 minutes. After a final wash, 500 µl of stain buffer was added to each sample and analyzed by flow cytometry.

Normal primary human chondrocyte were thawed into a T-75 flask in 20% premium non-heat inactivated FBS-DMEM/F-12 (Invitrogen 11330-032)+1% pen/strep and 1% L-Glutamine. The cells were plated (1.0×10$_6$ cells/10 ml or 5000 cells/100 µL of complete media) in a 100×20 mm tissue culture plate or 96-well plate respectively. The next day, the media was replaced with 10 ml or 100 µl serum-free media for 20 minutes to serum starve the cells. Compound A was added for 1 hour at 37° C. (0.25% final DMSO). In addition, cytokines IL-1β (10 ng/ml), IL-6 (10 ng/ml), and IL-6R (20 ng/ml) were added and the cells continued incubation overnight (18 hours) at 37° C. Supernatants were harvested at 24 and 48 hours and frozen at −20° C. The next day, human CXCL8/IL-8 human MMP-3 and pro-MMP-13 enzyme-linked immunosorbent assay (ELISA) was performed. Results are shown in FIGS. 26-28.

Taken together, these data demonstrate that combining either of the PDE4 inhibitors Compound A or Compound B with approved rheumatoid arthritis and psoriasis treatment options CsA, ETC, or MTX, particularly CsA or ETC, have a wide range of inhibitory effects including synergy, depending on the combinatorial concentration, further to block several inflammatory and disease-related cytokines.

6.6.9. Compound A Inhibits Osteoclastogenesis and Osteoblast Production of RANKL Human bone marrow cells were treated with Compound A and with 10 nM dexamethasone and 10 nM Vitamin D to differentiate cells into osteoclasts. Fresh media and Compound A were added every 3 days. At day 7 supernatant was collected and adherent cells were isolated to obtain RNA. Day 7 cells were stained with TRAPS and the number of osteoclasts was counted.

Results: Compound A was found to inhibit osteoclast formation, which provides evidence that Compound A may counteract the bone catabolic effect of corticosteroids. This provides a potential advantage as a treatment for arthritis, including rheumatoid arthritis.

Compound A also significantly inhibits osteoclastogenesis induced by vitamin D and corticosteroid treatment of bone marrow mononuclear cells. Normal human osteoblast cells (nHOST, source: Lonza) were plated in 6 well plates and incubated overnight for cell attachment. Cells were treated for 7 days with Compound A and with 10 nM dexamethasone and 10 nM Vitamin D. Compound and media was refreshed every 3-4 days. On Day 7 supernatent was collected for RANKL and OPG by ELISA.

Results: Compound A was found to cause a significant decrease in sRANKL after treatment of normal human osteoblast cells at concentrations of 1 µM and 10 µM Compound A. An increase in OPG was also observed after treatment with Compound A. Compound A did significantly inhibit the RANKL/OPG ratio in normal human osteoblast cells.

The embodiments described above are intended merely to be exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

What is claimed is:

1. A method of treating rheumatoid arthritis, which comprises administering to a patient in need of such treatment a therapeutically effective amount of a first active agent, wherein the first active agent is a compound of formula A:

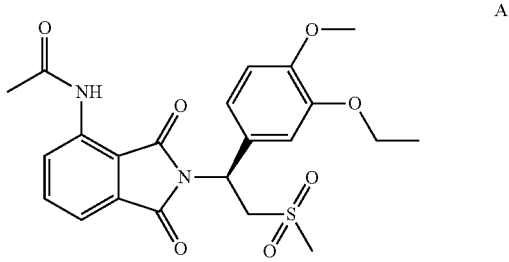 [SMILES: CCOc1cc([C@@H](CS(C)(=O)=O)N2C(=O)c3cccc(NC(C)=O)c3C2=O)ccc1OC]

or a pharmaceutically acceptable salt thereof, and a therapeutically effective amount of an additional active agent, wherein the additional active agent is cyclosporine A.

2. The method of claim 1, wherein the therapeutically effective amount of the first active agent is about 1, 5, 10, 15, 20, 25 or 30 mg per day and the therapeutically effective amount of the additional active agent is about 1, 5, or 6.25 mg per day.

3. The method of claim 1, wherein one or more of the active agents are administered orally.

4. The method of claim 3, wherein the first active agent is administered orally in a tablet or capsule form.

5. The method of claim 1, wherein one or more of the active agents are administered topically.

6. The method of claim 5, wherein the topical administration is in the form of a lotion or a liquid.

7. The method of claim 1, wherein the therapeutically effective amount of each active agent independently is from about 0.01 mg to about 100 mg per kg of a body weight of the patient per day.

8. The method of claim 1, wherein the therapeutically effective amount of each active agent independently is about 5, 10, 15, 20, 25 or 30 mg per kg of body weight of the patient per day.

9. The method of claim 1, wherein the therapeutically effective amount of each active agent independently is about 1 mg/kg to about 25 mg/kg of body weight of the patient per day.

10. A method of inhibiting a cytokine in a patient presenting with an inflammatory response associated with rheumatoid arthritis, which comprises administering to the patient a therapeutically effective amount of the compound of formula A

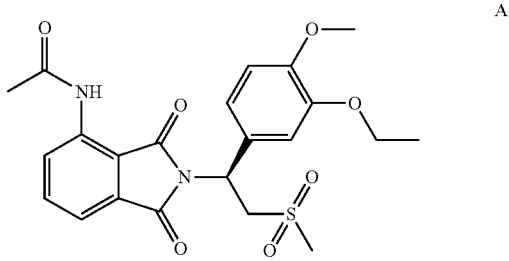 [SMILES: CCOc1cc([C@@H](CS(C)(=O)=O)N2C(=O)c3cccc(NC(C)=O)c3C2=O)ccc1OC]

or a pharmaceutically acceptable salt thereof, and a therapeutically effective amount of cyclosporine A, wherein the cytokine is IFN-γ, IL-13, IL-10, MIP-1α, MIP-1β, or TNF-α.

* * * * *